United States Patent
Wagner et al.

(10) Patent No.: US 10,219,895 B2
(45) Date of Patent: Mar. 5, 2019

(54) NANOFIBER-BASED GRAFT FOR HEART VALVE REPLACEMENT AND METHODS OF USING THE SAME

(71) Applicant: WAKE FOREST UNIVERSITY HEALTH SCIENCES, Winston-Salem, NC (US)

(72) Inventors: William D. Wagner, Clemmons, NC (US); Nicole Levi, Winston-Salem, NC (US); Rui Wang, Winston-Salem, NC (US); Louis C. Argenta, Winston-Salem, NC (US); Michael J. Morykwas, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 0 days.

(21) Appl. No.: 14/438,142

(22) PCT Filed: Oct. 25, 2013

(86) PCT No.: PCT/US2013/066747
§ 371 (c)(1),
(2) Date: Apr. 23, 2015

(87) PCT Pub. No.: WO2014/066724
PCT Pub. Date: May 1, 2014

(65) Prior Publication Data
US 2015/0272729 A1    Oct. 1, 2015

Related U.S. Application Data

(60) Provisional application No. 61/718,991, filed on Oct. 26, 2012.

(51) Int. Cl.
*A61F 2/24* (2006.01)
*A61K 9/70* (2006.01)
(Continued)

(52) U.S. Cl.
CPC .......... *A61F 2/2412* (2013.01); *A61F 2/2415* (2013.01); *A61F 2/82* (2013.01);
(Continued)

(58) Field of Classification Search
CPC .. A61L 2430/20; A61L 2400/12; A61L 27/26; A61L 27/56; A61L 27/54;
(Continued)

(56) References Cited

U.S. PATENT DOCUMENTS 4,187,852 A   2/1980 Urry
4,661,530 A   4/1987 Gogolewski
(Continued)

FOREIGN PATENT DOCUMENTS

DE   4439240   5/1996
GB   712939    8/1954
(Continued)

OTHER PUBLICATIONS

International Search Report from International Application No. PCT/US2013/066747, dated Dec. 20, 2013.
(Continued)

*Primary Examiner* — Dinah Baria
(74) *Attorney, Agent, or Firm* — Niels Haun; Dann, Dorfman, Herrell & Skillman, P.C.

(57) ABSTRACT

Nanofiber-based biomaterials containing fibroin for wound repair and tissue replacement and, more particularly, heart valve replacement.

29 Claims, 18 Drawing Sheets

(51) Int. Cl.

| | |
|---|---|
| *A61F 2/82* | (2013.01) |
| *A61L 27/26* | (2006.01) |
| *A61L 27/54* | (2006.01) |
| *A61L 27/56* | (2006.01) |
| *C08J 9/00* | (2006.01) |
| *C08L 89/00* | (2006.01) |
| *C08L 89/06* | (2006.01) |

(52) U.S. Cl.
CPC .............. *A61K 9/70* (2013.01); *A61L 27/26* (2013.01); *A61L 27/54* (2013.01); *A61L 27/56* (2013.01); *C08J 9/0061* (2013.01); *C08L 89/00* (2013.01); *C08L 89/06* (2013.01); *A61L 2300/414* (2013.01); *A61L 2400/12* (2013.01); *A61L 2430/20* (2013.01); *C08J 2389/00* (2013.01); *C08J 2389/06* (2013.01); *C08J 2467/02* (2013.01); *C08J 2489/00* (2013.01); *C08J 2489/06* (2013.01); *C08L 2201/06* (2013.01); *C08L 2203/02* (2013.01); *C08L 2203/12* (2013.01); *C08L 2205/02* (2013.01); *C08L 2205/03* (2013.01); *Y10T 428/298* (2015.01)

(58) Field of Classification Search
CPC ............ A61L 2300/414; C08J 2489/00; C08L 2203/02; C08L 2205/03; C08L 2205/02; C08L 2203/12; C08L 89/00; A61K 9/70
See application file for complete search history.

(56) References Cited

U.S. PATENT DOCUMENTS

| | | | |
|---|---|---|---|
| 4,841,962 A | 6/1989 | Berg | |
| 5,024,841 A | 6/1991 | Chu | |
| 5,490,962 A | 2/1996 | Cima | |
| 5,516,396 A | 5/1996 | Maurer | |
| 5,607,590 A | 3/1997 | Shimizu | |
| 5,736,372 A | 4/1998 | Vacanti | |
| 5,766,618 A | 6/1998 | Laurencin | |
| 6,095,148 A | 8/2000 | Shastri | |
| 6,106,913 A | 8/2000 | Scardino | |
| 6,695,823 B1 | 2/2004 | Lina | |
| 7,216,651 B2 | 5/2007 | Argenta | |
| 7,722,894 B2 | 5/2010 | Wang | |
| 8,632,523 B2 | 1/2014 | Eriksson | |
| 8,932,620 B2* | 1/2015 | Lelkes | A61K 35/12 424/423 |
| 2002/0004556 A1 | 1/2002 | Foulger | |
| 2003/0027332 A1 | 2/2003 | Lafrance | |
| 2003/0108587 A1 | 6/2003 | Orgill | |
| 2003/0109855 A1 | 6/2003 | Solem | |
| 2003/0118692 A1 | 6/2003 | Wang | |
| 2004/0210009 A1 | 10/2004 | Kobayashi | |
| 2005/0063939 A1 | 3/2005 | Ameer | |
| 2006/0263417 A1 | 11/2006 | Lelkes | |
| 2006/0293169 A1 | 12/2006 | Srinivasan | |
| 2007/0071790 A1 | 3/2007 | Ameer | |
| 2007/0155010 A1* | 7/2007 | Farnsworth | A61L 27/18 435/399 |
| 2007/0208420 A1 | 9/2007 | Ameer | |
| 2008/0009830 A1 | 1/2008 | Fujimoto | |
| 2008/0031934 A1 | 2/2008 | MacPhee | |
| 2008/0112998 A1 | 5/2008 | Wang | |
| 2008/0147156 A1 | 6/2008 | Imran | |
| 2009/0011486 A1 | 1/2009 | Bettinger | |
| 2009/0093565 A1 | 4/2009 | Yang | |
| 2009/0148945 A1 | 6/2009 | Ameer | |
| 2009/0187259 A1 | 7/2009 | Argenta | |
| 2009/0295644 A1 | 12/2009 | Curran | |
| 2009/0325859 A1 | 12/2009 | Ameer | |
| 2010/0196478 A1 | 8/2010 | Masters | |
| 2010/0221304 A1 | 9/2010 | Tan | |
| 2011/0052646 A1 | 3/2011 | Kaigler | |
| 2011/0129436 A1 | 6/2011 | Pryor | |
| 2011/0262489 A1 | 10/2011 | Zhao | |
| 2012/0016325 A1 | 1/2012 | Pinto | |
| 2012/0265297 A1 | 10/2012 | Altman | |
| 2014/0079758 A1* | 3/2014 | Hall | A61L 27/16 424/443 |
| 2014/0079759 A1* | 3/2014 | Patel | A61L 27/50 424/443 |
| 2014/0309726 A1 | 10/2014 | Wang | |

FOREIGN PATENT DOCUMENTS

| | | |
|---|---|---|
| JP | 1004629 | 1/1989 |
| JP | 2008099565 | 5/2008 |
| WO | 199000060 | 1/1990 |
| WO | 9918892 | 4/1999 |
| WO | 2000061206 | 10/2000 |
| WO | 03026489 | 4/2003 |
| WO | 2007060433 | 5/2007 |
| WO | 2012004627 | 1/2012 |
| WO | 2012078472 | 6/2012 |

OTHER PUBLICATIONS

Written Opinion from International Application No. PCT/US2013/066747, dated Dec. 20, 2013.
International Preliminary Report on Patentability from International Application No. PCT/US2013/066747, dated Apr. 28, 2015.
Barrett, DG and Yousaf, MN. Design and Applications of Biodegradable Polyester Tissue Scaffolds Based on Endogenous Monomers Found in Human Metabolism. Molecules, Oct. 12, 2009.
Dumitriu, Severian and Popa, Valentin. Polymeric Biomaterials: Structure and Function, vol. 1. Boca Raton, FL: CRC Press, Jan. 17, 2013.
International Search Report and Written Opinion from International Application No. PCT/US15/54484 dated Jan. 6, 2016.
Supplementary European Search Report for EP13849526 dated May 25, 2016.
Wang, R et al. "Evaluation of Repeated Biphasic Conducting Materials for Peripheral Nerve Repair" and "Injectable and Self-Assembling Sponge as a Protective Layer at Device-Tissue Interfaces in Wound Repair." BMES, 12th Annual Graduate Student Research Symposium. May 16, 2013.
Subramanian et al, Development of biomaterial scaffold for nerve tissue engineering: Biomaterial mediated neural regeneration, Journal of Biomedical Science, 2009, 16, pp. 1-11.
Yu et al, Promoting neuron adhesion and growth, Materials today, 2008, 11, pp. 36-43.
Widmer et al, Manufacture of porous biodegradable polymer conduits by an extrusion process for guided tissue regeneration, Biomaterials, 1998, 19, pp. 1945-1955.
Chen et al, Development of biodegradable porous scaffolds for tissue engineering, Materials Science and Engineering C, 2001, 17, pp. 63-69.
Lee et al, In vivo conjunctival reconstruction using modified PLGA grafts for decreased scar formation and contraction, Biomaterials, 2003, 24, pp. 5049-5059.
Cytometrics, from http://www.nanomedicine.com/NMI/8.5.1.htm, pp. 1-2, accessed Jul. 5, 2016.
May, The Effects of Biological Wound Dressings on the Healing Process,National Tissue Services, American Red Cross, 1991;8(3-4):243-9.
Salisbury et al., Biological Dressings and Evaporative Water Loss from Burn Wounds, Annals of Plastic Surgery vol. S No. 4 Oct. 1980, pp. 270-272.
Calvin et al., Microstructure and Mechanics of the Chorioamnion Membrane with an Emphasis on Fracture Properties, vol. 1101, Reproductive Biomechanics pp. 166-185, Apr. 2007.
Liu, Y., et al., "Engineering of bio-hybrid materials by electrospinning polymer-microbe fibers," P. Natl. Acad. Sci. USA 106(34):14201-14206 (Aug. 25, 2009).
Abdel-Fattah, W.I., et al., "Synthesis, characterization of chitosans and fabrication of sintered chitosan microsphere matrices for bone tissue engineering," Acta Biomaterialia 3:503-514 (2007).

(56) References Cited

OTHER PUBLICATIONS

Apte, S. S. (2011). "Current developments in the tissue engineering of autologous heart valves: moving towards clinical use." Future cardiology 7(1): 77-97.
Barakat, N.A.M., et al., "Polymeric nanofibers containing solid nanoparticles prepared by electrospinning and their applications," Chemical Engineering Journal 156:487-495 (2010).
Beachley, V., et al., "Polymer nanofibrous structures: Fabrication, biofunctionalization, and cell interactions," Progress in Polymer Science, 35(7):868-892 (Jul. 2010) (available online Mar. 17, 2010).
Beun, L. H., X. J. Beaudoux, et al. (2011). "Self-Assembly of Silk-Collagen-like Triblock Copolymers Resembles a Supramolecular Living Polymerization." ACS Nano 6(1): 133-140.
Billiar, K. L. and M. S. Sacks (2000). "Biaxial Mechanical Properties of the Native and Glutaraldehyde-Treated Aortic Valve Cusp: Part II—A Structural Constitutive Model." Journal of Biomechanical Engineering 122(4): 327-335.
Boissard, C.I.R., et al., "Nanohydroxyapatite/poly(ester urethane) scaffold for bone tissue engineering," Acta Biomaterialia 5:3316-3327 (Nov. 2009; available online May 12, 2009).
Boland, E.D., et al., "Electrospinning polydioxanone for biomedical applications," Acta Biomaterialia 1:115-123 (2005).
Bondar, B., S. Fuchs, et al. (2008). "Functionality of endothelial cells on silk fibroin nets: Comparative study of micro- and nanometric fibre size." Biomaterials 29(5): 561-572.
Breuer, C. K. (2004). "Application of tissue-engineering principles toward the development of a semilunar heart valve substitute." Tissue engineering 10 (11-12): 1725-1736.
Butcher, J. T., G. J. Mahler, et al. (2011). "Aortic valve disease and treatment: The need for naturally engineered solutions." Advanced Drug Delivery Reviews 63 (4-5): 242-268.
Causa, F., et al., "A multi-functional scaffold for tissue regeneration: The need to engineer a tissue analogue," Biomaterials, 28(34):5093-5099 (Dec. 2007; available online Aug. 6, 2007).
Cebotari, S. (2011). "Use of fresh decellularized allografts for pulmonary valve replacement may reduce the reoperation rate in children and young adults: early report." Circulation (New York, N.Y.) 124(11 suppl): S115-123.
Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.
Chen, R., et al., "Preparation and characterization of coaxial electrospun thermoplastic polyurethane/collagen compound nanofibers for tissue engineering applications," Colloids and Surfaces B: Biointerfaces 79(2):315-325 (Sep. 1, 2010) (available online Apr. 3, 2010).
Chen, W.-Q., H. Priewalder, et al. (2010). "Silk cocoon of Bombyx mori: Proteins and posttranslational modifications—heavy phosphorylation and evidence for lysine-mediated cross links." Proteomics 10(3): 369-379.
Chen, Y., et al., "Increased osteoblast functions in the presence of BMP-7 short peptides for nanostructured biomaterial applications," J. Biomed. Mater. Res. A 91:296-304 (2009; published online Nov. 3, 2008).
Chobanian, A. V., G. L. Bakris, et al. (2003). "Seventh Report of the Joint National Committee on Prevention, Detection, Evaluation, and Treatment of High Blood Pressure." Hypertension 42(6): 1206-1252.
Chronakis, I.S., "Novel nanocomposites and nanoceramics based on polymer nanofibers using electrospinning process—A review," Journal of Materials Processing Technology 167:283-293 (2005).
Cilurzo, F., C. G. M. Gennari, et al. (2011). "An investigation into silk fibroin conformation in composite materials intended for drug delivery." International Journal of Pharmaceutics 414(1-2): 218-224.
De Cock, L. J. (2010). "Layer-by-layer incorporation of growth factors in decellularized aortic heart valve leaflets." Biomacromolecules 11(4): 1002-1008.
De Cupere, V. M., J. Van Wetter, et al. (2003). "Nanoscale Organization of Collagen and Mixed Collagen Pluronic Adsorbed Layers." Langmuir 19(17): 6957-6967.

Deka, H., et al., "Biocompatible hyperbranched polyurethane/multi-walled carbon nanotube composites as shape memory materials," Carbon 48:2013-2022 (2010; available online Feb. 11, 2010).
Deng, C. (2011). "Application of decellularized scaffold combined with loaded nanoparticles for heart valve tissue engineering in vitro." Journal of Huazhong University of Science and Technology. Medical sciences 31(1): 88-93.
Deng, M., et al., "Biomimetic, bioactive etheric polyphosphazene-poly(lactide-co-glycolide) blends for bone tissue engineering," J. Biomed Mater Res A 92:114-125 (2010; published online Jan. 22, 2009).
Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).
Dijkman, P. E., A. Driessen-Mol, et al. (2012). "Decellularized homologous tissue-engineered heart valves as off-the-shelf alternatives to xeno- and homografts." Biomaterials 18:4545-54.
Dohmen, P. M., A. Lembcke, et al. (2011). "Ten Years of Clinical Results With a Tissue-Engineered Pulmonary Valve." The Annals of Thoracic Surgery 92(4): 1308-1314.
Dong, B., et al., "Electrospinning of collagen nanofiber scaffolds from benign solvents," Macromolecular Rapid Communications 30(7):539-542 (Feb. 5, 2009).
Douglas, T., et al., "Novel ceramic bone replacement material CeraBall® seeded with human mesenchymal stem cells," Clin. Oral Impl. Res. 21:262-267 (2010).
Edwards, M. B., E. R. Draper, et al. (2005). "Mechanical testing of human cardiac tissue: some implications for MRI safety." J Cardiovasc Magn Reson 7(5): 835-840.
Ekaputra, A.K., et al., "Composite electrospun scaffolds for engineering tubular bone grafts," Tissue Eng. Part A 15(12):3779-3788 (Dec. 8, 2009) (published online Jul. 20, 2009; online ahead of print: Jul. 24, 2009; online ahead of editing: Jun. 15, 2009).
Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).
Fujihara, K., et al., "Guided bone regeneration membrane made of polycaprolactone/calcium carbonate composite nano-fibers," Biomaterials 26:4139-4147 (2005; available online Dec. 24, 2004).
Gu, X. and K. S. Masters (2010). "Regulation of valvular interstitial cell calcification by adhesive peptide sequences." Journal of Biomedical Materials Research Part A 93A(4): 1620-1630.
Guan, J., et al., "Preparation and characterization of highly porous, biodegradable polyurethane scaffolds for soft tissue applications," Biomaterials 26:3961-3971 (2005; available online Dec. 8, 2004).
Hayashi, T. and S. Mukamel (2007). "Vibrational Exciton Couplings for the Amide I, II, III, and A Modes of Peptides." The Journal of Physical Chemistry B 111(37): 11032-11046.
Hersh, R.E., et al., "A technique for the treatment of sternal infections using the vacuum assisted closure device", Heart Surg. Forum, 4(3):211-15 (2001).
Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).
Hill, C.A., et al., "Superior sternal cleft repair using autologous rib grafts in an infant with complex congenital heart disease," Ann. Thorac. Surg., 84:673-4, (2007).
Hinton, R. B. and K. E. Yutzey (2011). "Heart Valve Structure and Function in Development and Disease." Annual Review of Physiology 73(1): 29-46.
Hong, Y., et al., "Preparation, bioactivity, and drug release of hierarchical nanoporous bioactive glass ultrathin fibers," Adv. Mater. 22:754-758 (2010).
Hong, Y., et al., "Tailoring the degradation kinetics of poly(ester carbonate urethane)urea thermoplastic elastomers for tissue engineering scaffolds," Biomaterials 31:4249-4258 (2010; available online Feb. 25, 2010).
Hopkins, R. A. (2005). "Tissue engineering of heart valves: decellularized valve scaffolds." Circulation (New York, N.Y.) 111(21): 2712-2714.

(56) References Cited

OTHER PUBLICATIONS

Horan, R. L., K. Antle, et al. (2005). "In vitro degradation of silk fibroin." Biomaterials 26(17): 3385-3393.
Hoshi, R.A., "Nanoporous biodegradable elastomers," Adv. Mater. 21:188-192 (2009).
Hu, X., D. Kaplan, et al. (2006). "Determining Beta-Sheet Crystallinity in Fibrous Proteins by Thermal Analysis and Infrared Spectroscopy." Macromolecules 39 (18): 6161-6170.
Ifkovits, J.L., et al., "Biodegradable and radically polymerized elastomers with enhanced processing capabilities," Biomed Mater. 3(3):034104 (Sep. 2008) (published Aug. 8, 2008).
Ifkovits, J.L., et al., "Biodegradable fibrous scaffolds with tunable properties formed from photo-cross-linkable poly(glycerol sebacate)," ACS Appl. Mater. Interfaces 1(9):1878-1886 (Sep. 2009; published online Sep. 11, 2009).
Jeong, C.G., et al., "Mechanical, permeability, and degradation properties of 3D designed poly(1,8 octanediol-co-citrate) scaffolds for soft tissue engineering," J. Biomed. Mater. Res. Part B: Appl. Biomater. 93(1):141-149 (Apr. 2010; published online Jan. 20, 2010).
Ji, Y., et al., "Electrospun three-dimensional hyaluronic acid nanofibrous scaffolds," Biomaterials 27:3782-3792 (2006; available online Mar. 23, 2006).
Jiang, C., X. Wang, et al. (2007). "Mechanical Properties of Robust Ultrathin Silk Fibroin Films." Advanced Functional Materials 17(13): 2229-2237.
Jordan, J. E., J. K. Williams, et al. (2012). "Bioengineered self-seeding heart valves." The Journal of thoracic and cardiovascular surgery 143(1): 201-208.
Kenar et al. (2010). Design of 3D aligned mycoardial tissue construct from biodegradable polyesters. J. Mater. Med 21:989-997.
Kidane, A. G., G. Burriesci, et al. (2009). "A novel nanocomposite polymer for development of synthetic heart valve leaflets." Acta Biomaterialia 5(7): 2409-2417.
Kidoaki, S., et al., "Mesoscopic spatial designs of nano- and microfiber meshes for tissue-engineering matrix and scaffold based on newly devised multilayering and mixing electrospinning techniques," Biomaterials 26(1):37-46 (Jan. 2005) (available online Mar. 2, 2004).
Kim, H.W., et al., "Bioactive glass nanofiber-collagen nanocomposite as a novel bone regeneration matrix," J. Biomed. Mater. Res. A 79:698-705 (2006; published online Jul. 18, 2006).
Kim, K., M. Yu, et al. (2003). "Control of degradation rate and hydrophilicity in electrospun non-woven poly(d,l-lactide) nanofiber scaffolds for biomedical applications." Biomaterials 24(27): 4977-4985.
Kim, S.S., et al., "Accelerated bonelike apatite growth on porous polymer/ceramic composite scaffolds in vitro," Tissue Eng. 12(10):2997-3006 (Oct. 2006).
Krogman, N.R., et al., "Hydrogen bonding in blends of polyesters with dipeptide-containing polyphosphazenes," J. Appl. Polym. Sci. 115:431-437 (2010; published online Sep. 1, 2009).
Krogman, N.R., et al., "The influence of side group modification in polyphosphazenes on hydrolysis and cell adhesion of blends with PLGA," Biomaterials 30:3035-3041 (2009; available online Apr. 5, 2009).
Lahiri, D., et al., "Boron nitride nanotube reinforced polylactide-polycaprolactone copolymer composite: Mechanical properties and cytocompatibility with osteoblasts and macrophages in vitro," Acta Biomaterialia 6:3524-3533 (2010; available online Mar. 10, 2010).
Lang et al. (2014) "A blood-resistant surgical glue for minimally invasive repair of vessels and heart defects," Science Translational Medicine, 6(218): 1-6.
Lee, K.-W., D. B. Stolz, et al. (2011). "Substantial expression of mature elastin in arterial constructs." Proceedings of the National Academy of Sciences 108(7): 2705-2710.
Leonelli, C., et al., "Synthesis and characterization of cerium-doped glasses and in vitro evaluation of bioactivity," Journal of Non-Crystalline Solids 316:198-216 (2003).
Li, C., et al., "Electrospun silk-BMP-2 scaffolds for bone tissue engineering," Biomaterials, 27(16):3115-3124 (Jun. 2006) (available online Feb. 3, 2006).
Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.
Li, M., et al., "Electrospun protein fibers as matrices for tissue engineering," Biomaterials 26(30):5999-6008 (Oct. 2005) (available online May 13, 2005).
Li, W.J., et al., "Fabrication and characterization of six electrospun poly(alpha-hydroxy ester)-based fibrous scaffolds for tissue engineering applications," Acta Biomater. 2(4):377-385 (Jul. 2006; published online May 6, 2006).
Liu, T., W. K. Teng, et al. (2010). "Photochemical crosslinked electrospun collagen nanofibers: Synthesis, characterization and neural stem cell interactions." Journal of Biomedical Materials Research Part A 95A(1): 276-282.
Liu, Y., et al., "Electrospinning of poly(ethylene-co-vinyl acetate)/clay nanocomposite fibers," J. Polym. Sci.: Part B: Polym. Phys. 47:2501-2508 (Dec. 2009; first published online Nov. 10, 2009).
Lombardi, S. J. and D. L. Kaplan (1990). "The Amino Acid Composition of Major Ampullate Gland Silk (Dragline) of Nephila Clavipes (Araneae, Tetragnathidae)." Journal of Arachnology 18(3): 297-306.
Lu, X.L., et al., "Shape memory property of poly(L-lactide-co-μ-caprolactone) copolymers," Materials Science and Engineering A 438-440:857-861 (2006).
Ma, Z., et al., "Potential of nanofiber matrix as tissue-engineering scaffolds," Tissue Engineering 11(1/2):101-109 (2005).
Malafaya, P. B., G. A. Silva, et al. (2007). "Natural-origin polymers as carriers and scaffolds for biomolecules and cell delivery in tissue engineering applications." Advanced Drug Delivery Reviews 59(4-5): 207-233.
Martins, A., et al., "Biodegradable nanofibers-reinforced microfibrous composite scaffolds for bone tissue engineering," Tissue Engineering: Part A, 16(12):3599-3609 (2010) (published online Sep. 21, 2010).
Mendelboum Raviv, S., K. Szekeres-Csiki, et al. (2011). "Coating conditions matter to collagen matrix formation regarding von Willebrand factor and platelet binding." Thrombosis Research 129(4):e29-35.
Min, B.M., You, Y., Kim, J.M., Lee, S.J. & Park, W.H. Formation of nanostructured poly(lactic-co-glycolic acid)/chitin matrix and its cellular response to normal human keratinocytes and fibroblasts. Carbohydrate Polymers 57, 285-292 (2004).
Minoura, N., M. Tsukada, et al. (1990). "Fine structure and oxygen permeability of silk fibroin membrane treated with methanol." Polymer 31(2): 265-269.
Mirensky, T. L. and C. K. Breuer (2008). "The Development of Tissue-Engineered Grafts for Reconstructive Cardiothoracic Surgical Applications." Pediatr Res 63 (5): 559-568.
Misra, S.K., et al., "Characterization of carbon nanotube (MWCNT) containing P(3HB)/bioactive glass composites for tissue engineering applications," Acta Biomaterialia 6:735-742 (2010; available online Oct. 1, 2009).
Mol, A. (2004). "Review article: Tissue engineering of semilunar heart valves: current status and future developments." The Journal of heart valve disease 13 (2): 272-280.
Motlagh et al. (2006) "Hemocompatibility Evaluation of Poly(glycerol-sebacate) in vitro for vascular tissue engineering", Biomaterials 27(24): 4315-4324.
Nagata, M., et al., "Synthesis, characterization, and enzymatic degradation of network aliphatic copolyesters," Journal of Polymer Science: Part A: Polymer Chemistry, 37:2005-2011 (1999).
Nair, L.S., et al., "Biodegradable polymers as biomaterials," Prog. Polym. Sci. 32:762-798 (2007; available online Jun. 11, 2007).
Nair, L.S., et al., "Nanofibers and nanoparticles for orthopaedic surgery applications," J. Bone Joint Surg. Am. 90(Supp. 1):128-131 (2008).
Nair et al. (2004). "Development of novel tissue engineering scaffolds via electrospinning." Exper. Opin. Biol. Ther. 4:659-668.
Ndreu, A., et al., "Electrospun biodegradable nanofibrous mats for tissue engineering," Nanomedicine (Lond.) 3(1):45-60 (Feb. 2008), 1 sheet abstract.

(56) References Cited

OTHER PUBLICATIONS

Newton, D., R. Mahajan, et al. (2009). "Regulation of material properties in electrospun scaffolds: Role of cross-linking and fiber tertiary structure." Acta Biomaterialia 5(1): 518-529.
Nkomo, V. T., J. M. Gardin, et al. (2006). "Burden of valvular heart diseases: a population-based study." The Lancet 368(9540): 1005-1011.
Okhawilai, M. (2010). "Preparation of Thai silk fibroin/gelatin electrospun fiber mats for controlled release applications." International journal of biological macromolecules 46(5): 544-550.
Ostergaard L, Kristiansen SB, Angleys H, et al. The role of capillary transit time heterogeneity in myocardial oxygenation and ischemic heart disease. Basic Res Cardiol May 2014;109(3):409.
Pomerantseva, I., N. Krebs, et al. (2009). "Degradation behavior of poly(glycerol sebacate)." Journal of Biomedical Materials Research Part A 91A(4): 1038-1047.
Qiu, H., et al., "A citric acid-based hydroxyapatite composite for orthopedic implants," Biomaterials 27:5845-5854 (2006) (available online Aug. 21, 2006).
Ranganathan, S.I., et al., "Shaping the micromechanical behavior of multi-phase composites for bone tissue engineering," Acta Biomaterial 6:3448-3456 (2010; available online Mar. 24, 2010).
Ren, L., et al., "Fabrication of gelatin-siloxane fibrous mats via sol-gel and electrospinning procedure and its application for bone tissue engineering," Materials Science and Engineering C 30:437-444 (2010; available online Jan. 11, 2010).
Rockwood, D. N., R. C. Preda, et al. (2011). "Materials fabrication from Bombyx mori silk fibroin." Nat. Protocols 6(10): 1612-1631.
Ruzmetov, M., J. J. Shah, et al. (2012). "Decellularized versus standard cryopreserved valve allografts for right ventricular outflow tract reconstruction: A single-institution comparison." The Journal of thoracic and cardiovascular surgery 143(3): 543-549.
Sacks, M. S., F. J. Schoen, et al. (2009). "Bioengineering Challenges for Heart Valve Tissue Engineering." Annual Review of Biomedical Engineering 11(1): 289-313.
Sant, S., C. M. Hwang, et al. (2011). "Hybrid PGS-PCL microfibrous scaffolds with improved mechanical and biological properties." Journal of Tissue Engineering and Regenerative Medicine 5(4): 283-291.
Sant, S., et al., "Fabrication and characterization of tough elastomeric fibrous scaffold applications," Conf. Proc. IEEE Eng. Med. Biol. Soc. 2010:3546-3548, and 32nd Annual International Conference of the IEEE EMBS Buenos Aires, Argentina, (Aug. 31-Sep. 4, 2010).
Sant, S. and A. Khademhosseini (2010). Fabrication and characterization of tough elastomeric fibrous scaffolds for tissue engineering applications. Engineering in Medicine and Biology Society (EMBC), 2010 Annual International Conference of the IEEE.
Sasaki, N., et al., "Stress-strain curve and Young's Modulus of a collagen molecule as determined by the x-ray diffraction technique," J. Biomechanics, 29 (5):655-658 (1996).
Schofer, M.D., et al., "Characterization of a PLLA-collagen I blend nanofiber scaffold with respect to growth and osteogenic differentiation of human mesenchymal stem cells," ScientificWorldJournal 9:118-129 (Feb. 15, 2009).
Schopka, S. (2009). "Recellularization of biological heart valves with human vascular cells: in vitro hemocompatibility assessment." Journal of biomedical materials research. Part B, Applied biomaterials 88(1): 130-138.
Schroeder, W. A., L. M. Kay, et al. (1955). "The Amino Acid Composition of Bombyx mori Silk Fibroin and of Tussah Silk Fibroin." Journal of the American Chemical Society 77(14): 3908-3913.
Sell, S. A., M. J. McClure, et al. (2009). "Electrospinning of collagen/biopolymers for regenerative medicine and cardiovascular tissue engineering." Advanced Drug Delivery Reviews 61(12): 1007-1019.
Sell, S. A., P. S. Wolfe, et al. (2010). "The Use of Natural Polymers in Tissue Engineering: A Focus on Electrospun Extracellular Matrix Analogues." Polymers 2(4): 522-553.

Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).
Shah, P.N., et al., "Electrospinning of L-tyrosine polyurethanes for potential biomedical applications," Polymer 50:2281-2289 (May 2009; available online Mar. 19, 2009).
Shekaran, A. and A. J. Garcia (2011). "Nanoscale engineering of extracellular matrix-mimetic bioadhesive surfaces and implants for tissue engineering." Biochimica et Biophysica Acta (BBA)—General Subjects 1810(3): 350-360.
Simon, P., M. T. Kasimir, et al. (2003). "Early failure of the tissue engineered porcine heart valve SYNERGRAFT® in pediatric patients." European Journal of Cardio-Thoracic Surgery 23(6): 1002-1006.
Simone, E. A., T. D. Dziubla, et al. (2009). "Filamentous Polymer Nanocarriers of Tunable Stiffness that Encapsulate the Therapeutic Enzyme Catalase." Biomacromolecules 10(6): 1324-1330.
Sjogren, J., et al., "Vacuum-assisted closure therapy in mediastinitis after heart transplantation", J. Heart Lung Transplant., 23(4):506-7 (Apr. 2004).
Smith, I.O., et al., "Nanostructured polymer scaffolds for tissue engineering and regenerative medicine," Interdisciplinary Reviews: WIREs Nanomed. Nanobiotechnol. 1 (2):226-236 (Mar./Apr. 2009) (Jan. 12, 2009).
Smith, L.A., et al., "Nano-fibrous scaffolds for tissue engineering," Colloids and Surfaces B: Biointerfaces 39(3):125-131 (Dec. 10, 2004; available online Feb. 4, 2004).
Soletti, L., et al., "A bilayered elastomeric scaffold for tissue engineering of small diameter vascular grafts," Acta Biomaterialia 6:110-122 (2010; available online Jun. 18, 2009).
Soliman, S., S. Sant, et al. (2011). "Controlling the porosity of fibrous scaffolds by modulating the fiber diameter and packing density." Journal of Biomedical Materials Research Part A 96A(3): 566-574.
Sung, H.-W., C.-N. Chen, et al. (2000). "In vitro surface characterization of a biological patch fixed with a naturally occurring crosslinking agent." Biomaterials 21(13): 1353-1362.
Tedder, M. E. (2009). "Stabilized collagen scaffolds for heart valve tissue engineering." Tissue engineering. Part A 15(6): 1257-1268.
Trowbridge, E. A., P. V. Lawford, et al. (1989). "Pericardial heterografts: a comparative study of suture pull-out and tissue strength." Journal of Biomedical Engineering 11(4): 311-314.
Um, I. C., H. Kweon, et al. (2001). "Structural characteristics and properties of the regenerated silk fibroin prepared from formic acid." International journal of biological macromolecules 29(2): 91-97.
Um, I.C., et al., "Electro-spinning and electro-blowing of hyaluronic acid," Biomacromolecules 5:1428-1436 (2004; published online May 7, 2004).
Van Susante, J.L.C., et al., "Linkage of chondroitin-sulfate to type I collagen scaffolds stimulates the bioactivity of seeded chondrocytes in vitro," Biomaterials, 22:2359-2369 (2001).
Venugopal, J., et al., "Biomimetic hydroxyapatite-containing composite nanofibrous substrates for bone tissue engineering," Phil. Trans. R. Soc. A 368:2065-2081 (2010).
Venugopal, J.R., et al., "Nanobioengineered electrospun composite nanofibers and osteoblasts for bone regeneration," Artif. Organs 32(5):388-397 (2008).
Vesely, I. and R. Noseworthy (1992). "Micromechanics of the fibrosa and the ventricularis in aortic valve leaflets." Journal of Biomechanics 25(1): 101-113.
Wan, L.-S. and Z.-K. Xu (2009). "Polymer surfaces structured with random or aligned electrospun nanofibers to promote the adhesion of blood platelets." Journal of Biomedical Materials Research Part A 89A(1): 168-175.
Wan, Y., et al., "Biphasic scaffold for annulus fibrosus tissue regeneration," Biomaterials 29:643-652 (2008; available online Nov. 13, 2007).
Wang, C., et al., "Correlation between processing parameters and microstructure of electrospun poly(D,L-lactic acid) nanofibers," Polymer 50:6100-6110 (Nov. 2009; available online Oct. 30, 2009).

(56) References Cited

OTHER PUBLICATIONS

Wang, J., et al., "Spiral-structured, nanofibrous, 3D scaffolds for bone tissue engineering," J. Biomed. Mater. Res. A 93:753-762 (2010; published online Jul. 29, 2009).
Wang, W., et al., "Biodegradable polyurethane based on random copolymer of L-lactide and μ-caprolactone and its shape-memory property," J. Appl. Polym. Sci. 104:4182-4187 (2007).
Wang, Y., et al., "In vivo degradation characteristics of poly(glycerol sebacate)," J. Biomed Mater Res A, 66(1):192-197 (Jul. 1, 2003) (published online Jun. 10, 2003).
Wang, Y., G. A. Ameer, et al. (2002). "A tough biodegradable elastomer." Nat Biotech 20(6): 602-606.
Wang et al. (2012) "Novel Nanofiber-based Graft for Heart Valve Replacement," Thesis for Master of Science, Biomedical Engineering, Wake Forest University Dec. 12, 2012.
Webb, A.R., et al., "Biodegradable polyester elastomers in tissue engineering," Expert Opin. Biol. Ther. 4(6):801-812 (2004).
Yacoub, M. H. and J. J. M. Takkenberg (2005). "Will heart valve tissue engineering change the world?" Nat Clin Pract Cardiovasc Med 2(2): 60-61.
Yacoub, M. H. and L. H. Cohn (2004). "Novel Approaches to Cardiac Valve Repair." Circulation 109(9): 1064-1072.
Yamada, K. M., D. W. Kennedy, et al. (1980). "Characterization of fibronectin interactions with glycosaminoglycans and identification of active proteolytic fragments." Journal of Biological Chemistry 255(13): 6055-6063.
Yang, J., et al., "Synthesis and evaluation of poly(diol citrate) biodegradable elastomers," Biomaterials 27:1889-1898 (2006; available online Nov. 15, 2005).
Yang, X., et al., "Acceleration of osteogenic differentiation of preosteoblastic cells by chitosan containing nanofibrous scaffolds," Biomacromolecules 10 (10):2772-2778 (Sep. 10, 2009).
Yang, X., et al., "Multifunctional nanofibrous scaffold for tissue engineering," Journal of Experimental Nanoscience 3(4):329-345 (2008).
Yang et al., "Electrospinning of nano/micro scale poly(L-lactic acid) aligned fibers and their potential in neural tissue engineering," Biomaterials 260:2603-2610 (2005).
Yi, F., et al., "Poly(glycerol sebacate) nanofiber scaffolds by core/shell electrospinning," Macromol. Biosci. 8:803-806 (2008).
Yi, F. and D. A. LaVan (2008). "Poly(glycerol sebacate) Nanofiber Scaffolds by Core/Shell Electrospinning." Macromolecular Bioscience 8(9): 803-806.
Yoganathan, A. P., Z. He, et al. (2004). "Fluid Mechanics of Heart Valves." Annual Review of Biomedical Engineering 6(1): 331-362.
Yoshimoto, H., et al., "A biodegradable nanofiber scaffold by electrospinning and its potential for bone tissue engineering," Biomaterials 24(12):2077-2082 (May 2003).
Zhang, Y., et al., "Electrospun biomimetic nanocomposite nanofibers of hydroxyapatite/chitosan for bone tissue engineering," Biomaterials 29:4314-4322 (2008; available online Aug. 20, 2008).
Zhong, S.P., et al., "Development of a novel collagen-GAG nanofibrous scaffold via electrospinning," Materials Science and Engineering: C, 27(2):262-266 (Mar. 2007) (available online Jun. 8, 2006).
Zhou, C.-Z., et al. (2001) "Silk Fibroin: Structural implications of a remarkable amino acid sequence." Proteins: Structure, Function, and Bioinformatics 44(2): p. 119-122.
Zhou, J., C. Cao, et al. (2010). "In vitro and in vivo degradation behavior of aqueous-derived electrospun silk fibroin scaffolds." Polymer Degradation and Stability 95(9): 1679-1685.
Zhu, J., A. Negri, et al. (2010). "Closed headpiece of integrin alphaIIbbeta3 and its complex with an alphaIIbbeta3-specific antagonist that does not induce opening." Blood(Aug. 2, 2010): 2010 Dec. 2012;2116(2023):5050-2019.
Zoccola, M., A. Aluigi, et al. (2008). "Study on Cast Membranes and Electrospun Nanofibers Made from Keratin/Fibroin Blends." Biomacromolecules 9(10): 2819-2825.
Zong, X., S. Ran, et al. (2003). "Structure and Morphology Changes during in Vitro Degradation of Electrospun Poly(glycolide-co-lactide) Nanofiber Membrane." Biomacromolecules 4(2): 416-423.
Zou, L., S. Cao, et al. (2012). "Fibronectin induces endothelial cell migration through beta1-integrin and Src dependent phosphorylation of fibroblast growth factor receptor-1 at tyrosines 653/654 and 766." Journal of Biological Chemistry.
Extended European Search Report from European Patent Application No. 13775894.2, dated Nov. 27, 2015.
International Preliminary Report on Patentability from International Application No. PCT/US2013/032520 dated Oct. 14, 2014.
International Search Report from International Application No. PCT/US2013/032520 dated Aug. 2, 2013.
Written Opinion from International Application No. PCT/US2013/032520 dated Aug. 2, 2013.
Evans GRD. Peripheral nerve injury: A review and approach to tissue engineered constructs. Anatomical Record 2001; 263(4):396-404.
Meek MF, Coert JH. US Food and Drug Administration/Conformit Europe-approved absorbable nerve conduits for clinical repair of peripheral and cranial nerves. Ann Plast Surg Jan. 2008;60(1):110-116.
Sondell M, Lundborg G, Kanje M. Regeneration of the rat sciatic nerve into allografts made acellular through chemical extraction. Brain Res Jun. 8, 1998;795 (1-2):44-54.
Merle M, Dellon AL, Campbell JN, Chang PS. Complications from silicon-polymer intubulation of nerves. Mircrosurgery 1989; 10(2):130-133.
Meek MF, Coert JH. Clinical use of nerve conduits in peripheral-nerve repair: review of the literature. J Reconstr Microsurg Feb. 2002;18(2):97-109.
FitzGerald MJT. Neuroanatomy: Basic and Clinical. Philadelphia: W.B. Saunders Company, Ltd., 1996.
Young PA, Young PH. Basic Clinical Neuroanatomy. Philedelphia: Lippincott Williams, and Wilkins, 1997.
MacKinnon SE, Dellon AL. Surgery of the Peripheral Nerve. Thieme Medical Publishers New York, 1988.
Medscape: Diseases of the Peripheral Nervous System. Web MD Inc., ACP Medicine, 2004.
Stoll G, Muller HW. Nerve injury, axonal degeneration and neural regeneration: basic insights. Brain Pathol Apr. 1999;9(2):313-325.
Gordon T. The role of neurotrophic factors in nerve regeneration. Neurosurg Focus 2009;26(2):E3.
Wood MD, Moore AM, Hunter DA, Tuffaha S, Borschel GH, Mackinnon SE, et al. Affinity-based release of glial-derived neurotrophic factor from fibrin matrices enhances sciatic nerve regeneration. Acta Biomater May 2009;5(4):959-968.
Hayashi A, Moradzadeh A, Tong A, Wei C, Tuffaha SH, Hunter DA, et al. Treatment modality affects allograft-derived Schwann cell phenotype and myelinating capacity. Exp Neurol Aug. 2008;212(2):324-336.
Lee AC, Yu VM, Lowe JB, 3rd, Brenner MJ, Hunter DA, Mackinnon SE, et al. Controlled release of nerve growth factor enhances sciatic nerve regeneration. Exp Neurol Nov. 2003;184(1):295-303.
Deister C, Schmidt CE. Optimizing neurotrophic factor combinations for neurite outgrowth. J Neural Eng Jun. 2006;3(2):172-179.
Ahmed I, Liu HY, Mamiya PC, Ponery AS, Babu AN, Weik T, et al. Three-dimensional nanofibrillar surfaces covalently modified with tenascin-C-derived peptides enhance neuronal growth in vitro. J Biomed Mater Res A Mar. 15, 2006;76(4):851-860.
Zhang L, Ma Z, Smith GM, Wen X, Pressman Y, Wood PM, et al. GDNF-enhanced axonal regeneration and myelination following spinal cord injury is mediated by primary effects on neurons. Glia Jan. 23, 2009.
Zhang X, MacDiarmid AG, Manohar SK. Chemical synthesis of PEDOT nanofibers. Chem Commun (Camb) Nov. 14, 2005(42):5328-5330.
Kim YT, Haftel VK, Kumar S. Bellamkonda RV. The role of aligned polymer fiber-based constructs in the bridging of long peripheral nerve gaps. Biomaterials Jul. 2008;29(21):3117-3127.
Wen X, Tresco PA. Effect of filament diameter and extracellular matrix molecule precoating on neurite outgrowth and Schwann cell behavior on multifilament entubulation bridging device in vitro. J Biomed Mater Res A Mar. 1, 2006;76(3):626-637.

(56) References Cited

OTHER PUBLICATIONS

Corey JM, Lin DY, Mycek KB, Chen Q, Samuel S, Feldman EL, et al. Aligned electrospun nanofibers specify the direction of dorsal root ganglia neurite growth. J Biomed Mater Res A Dec. 1, 2007;83(3):636-645.
Fan YW, Cui FZ, Chen LN, Zhai Y, Xu QY, Lee IS. Adhesion of neural cell son silicon wafer with nano-topographic surface. Applied Surface Science 2002;187(3-4):313-318.
Schmalenberg KE, Uhrich KE. Micropatterned polymer substrates control alignment of proliferating Schwann cells to direct neuronal regeneration. Biomaterials Apr. 2005;26(12):1423-1430.
Bruder JM, Lee AP, Hoffman-Kim D. Biomimetic materials replicating Schwann cell topography enhance neuronal adhesion and neurite alignment in vitro. J Biomater Sci Polym Ed 2007;18(8):967-982.
Borschel GH, Kia KF, Kuzon WM, Jr., Dennis RG. Mechanical properties of acellular peripheral nerve. J Surg Res Oct. 2003;114(2):133-139.
Rydevik BL, Kwan MK, Myers RR, Brown RA, Triggs KJ, Woo SLY, et al. An Invitro Mechanical and Histological Study of Acute Stretching on Rabbit Tibial Nerve. Journal of Orthopaedic Research 1990;8(5):694-701.
Guan J, Stankus JJ, Wagner WR. Biodegradable elastomeric scaffolds with basic fibroblast growth factor release. Journal of Controlled Release 2007;120(1-2):70-78.
Guan YQ, Tao HM, Li YC, Wang WW, Li ZB, Peng CL. Preparation and activity of a nanometer anti-microbial polyurethane. Journal of Wuhan University of Technology—Materials Science Edition 2009;24(4):540-545.
Wang S, Wan AC, Xu X, Gao S, Mao HQ, Leong KW, et al. A new nerve guide conduit material composed of a biodegradable poly(phosphoester). Biomaterials May 2001;22(10):1157-1169.
Wang W, Itoh S, Matsuda A, Ichinose S, Shinomiya K, Hata Y, et al. Influences of mechanical properties and permeability on chitosan nano/microfiber mesh tubes as a scaffold for nerve regeneration. J Biomed Mater Res A Feb. 2008;84(2):557-566.
Ciardelli G, Rechichi A, Cerrai P, Tricoli M, Barbani N, Giusti P. Segmented polyurethanes for medical applications: Synthesis, characterization and in vitro enzymatic degradation studies. Macromolecular Symposia 2004;218:261-271.
Evans AJ, Thompson BC, Wallace GG, Millard R, O\Leary SJ, Clark GM, et al. Promoting neurite outgrowth from spiral ganglion neuron explants using polypyrrole/BDNF-coated electrodes. J Biomed Mater Res A Oct. 2009;91(1):241-250.
Cho Y, Shi R, Ivanisevic A, Ben Borgens R. A mesoporous silica nanosphere-based drug delivery system using an electrically conducting polymer. Nanotechnology Jul. 8, 2009;20(27):275102.
Guimard NK, Gomez N, Schmidt CE. Conducting polymers in biomedical engineering. Progress in Polymer Science 2007;32:876-921.
Thompson BC, Richardson RT, Moulton SE, Evans AJ, O\Leary S, Clark GM, et al. Conducting polymers, dual neurotrophins and pulsed electrical stimulation—Dramatic effects on neurite outgrowth. J Control Release Sep. 27, 2009.
Cullen DK, A RP, Doorish JF, Smith DH, Pfister BJ. Developing a tissue-engineered neural-electrical relay using encapsulated neuronal constructs on conducting polymer fibers. J Neural Eng Dec. 2008;5(40):374-384.
Cui X, Lee VA, Raphael Y, Wiler JA, Hetke JF, Anderson DJ, et al. Surface modification of neural recording electrodes with conducting polymer/biomolecule blends. J Biomed Mater Res Aug. 2001;56(2):261-272.
Murphy CJ, Jana NR. Controlling the aspect ratio of inorganic nanorods and nanowires. Adv Mater Jan. 2002;14(1):80-82.
Li J, Ma PC, Chow WS, To CK, Tang BZ, Kim JK. Correlations between percolation threshold, dispersion state, and aspect ratio of carbon nanotubes. Advanced Functional Materials 2007;17(16):3207-3215.

Bauhofer W, Kovacs JZ. A review and analysis of electrical percolation in carbon nanotube polymer composites. Composites Science and Technology 2009;69(10):1486-1498.
Hernandez JJ, Garcia-Gutierrez MC, Nogales A, Rueda DR, Kwiatkowska M, Szymczyk A, et al. Influence of preparation procedure on the conductivity and transparency of SWCNT-polymer nanocomposites. Composites Science and Technology 2009;69(11-12):1867-1872.
Caswell KK, Bender CM, Murphy CJ. Seedless, surfactantless wet chemical synthesis of silver nanowires. Nano Lett May 2003;3(5):667-669.
Gole A, Murphy CJ. Seed-mediated synthesis of gold nanorods: Role of the size and nature of the seed. Chem Mat Sep. 2004;16(19):3633-3640.
De S, Higgins TM, Lyons PE, Doherty EM, Nirmalraj PN, Blau WJ, et al. Silver Nanowire Networks as Flexible, Transparent, Conducting Films: Extremely High DC to Optical Conductivity Ratios. ACS Nano Jul. 2009;3(7)1767-1774.
Kostarelos K. The long and short of carbon nanotube toxicity. Nature Biotechnology 2008;26(7):774-776.
Lam CW, James JT, McCluskey R, Arepalli S, Hunter RL. A review of carbon nanotube toxicity and assessment of potential occupational and environmental health risks. Critical Reviews in Toxicology 2006;36(3):189-217.
Zhang XP, Sun BQ, Friend RH, Guo HC, Nau D, Giessen H. Metallic photonic crystals based on solution-processible gold nanoparticles. Nano Lett Apr. 2006;6(4):651-655.
Kalbacova M, Kalbac M, Dunsch L, Kataura H, Hempel U. The study of the interaction of human mesenchymal stem cells and monocytes/macrophages with single-walled carbon nanotube films. Phys Status Solidi B—Basic Solid State Phys Nov. 2006;243(13):3514-3518.
Kalbacova M, Kalbac M, Dunsch L, Kromka A, Vanecek M, Rezek B, et al. The effect of SWCNT and nano-diamond films on human osteoblast cells. Phys Status Solidi B—Basic Solid State Phys 2007;244(11):4356-4359.
Hu H, Ni YC, Montana V, Haddon RC, Parpura V. Chemically functionalized carbon nanotubes as substrates for neuronal growth. Nano Lett 2004;4(3):507-511.
Wang LM, Li YF, Zhou LJ, Liu Y, Meng L, Zhang K, et al. Characterization of gold nanorods in vivo by integrated analytical techniques: their uptake, retention, and chemical forms. Anal Bioanal Chem Feb;396(3):1105-1114.
Chen X, Schluesener HJ. Nanosilver: A nanoproduct in medical application. Toxicol Lett Jan. 2008;176(1):1-12.
Carlson C, Hussain SM, Schrand AM, Braydich-Stolle LK, Hess KL, Jones RL, et al. Unique Cellular Interaction of Silver Nanoparticles: Size-Dependent Generation of Reactive Oxygen Species. J Phys Chem B 2008;112(43):13608-13619.
AshaRani PV, Hande MP, Valiyaveettil S. Anti-proliferative activity of silver nanoparticles. BMC Cell Biol Sep. 2009;10:14.
Alkilany AM, Nagaria PK, Hexel CR, Shaw TJ, Murphy CJ, Wyatt MD. Cellular Uptake and Cytotoxicity of Gold Nanorods: Molecular Origin of Cytotoxicity and Surface Effects. Small Mar. 2009;5(6):701-708.
Bashar SA. Study of Indium Tin Oxide (ITO) for Novel Optoelectronic Devices. King\s College London: University of London; 1998.
Mitsumoto H, Tsuzaka K. Neurotrophic factors and neuromuscular disease: I. General comments, the neurotrophin family, and neuropoietic cytokines. Muscle Nerve Aug. 1999;22(8):983-999.
Jones DM, Tucker BA, Rahimtula M, Mearow KM. The synergistic effects of NGF and IGF-1 on neurite growth in adult sensory neurons: convergence on the PI 3-kinase signaling pathway. J Neurochem Sep. 2003;86(5):1116-1128.
Sakiyama-Elbert SE, Hubbell JA. Controlled release of nerve growth factor from a heparin-containing fibrin-based cell ingrowth matrix. J Control Release Oct. 3, 2000;69(1)149-158.
Webber CA, Xu Y, Vanneste KJ, Martinez JA, Verge VM, Zochodne DW. Guiding adult Mammalian sensory axons during regeneration. J Neuropathol Exp Neurol Mar. 2008;67(3):212-222.
Xu X, Yee WC, Hwang PY, Yu H, Wan AC, Gao, et al. Peripheral nerve regeneration with sustained release of poly(phosphoester)

(56) References Cited

OTHER PUBLICATIONS microencapsulated nerve growth factor within nerve guide conduits. Biomaterials Jun. 2003;24(13):2405-2412.

Boyd JG, Gordon T. A dose-dependent facilitation and inhibition of peripheral nerve regeneration by brain-derived neurotrophic factor. Eur J Neurosci Feb. 2002;15(4):613-626.

Batchelor PE, Porritt MJ, Martinello P, Parish CL, Liberatore GT, Donnan GA, et al. Macrophages and Microglia Produce Local Trophic Gradients That Stimulate Axonal Sprouting Toward but Not beyond the Wound Edge. Mol Cell Neurosci Nov. 2002;21(3):436-453.

Batchelor PE, Wills TE, Hewa AP, Porritt MJ, Howells DW. Stimulation of axonal sprouting by trophic factors immobilized within the wound core. Brain Res May 13, 2008;1209:49-56.

Barras FM, Pasche P, Bouche N, Aebischer P, Zurn AD. Glial cell line-derived neurotrophic factor released by synthetic guidance channels promotes facial nerve regeneration in the rat. J Neurosci Res Dec. 15, 2002;70(6):746-755.

Ohta M, Suzuki Y, Chou H, Ishikawa N, Suzuki S, Tanihara M, et al. Novel heparin/alginate gel combines with basic fibroblast growth factor promotes nerve regeneration in rat sciatic nerve. J Biomed Mater Res A Dec. 15, 2004;71(4):661-668.

Winseck AK, Caldero J, Ciutat D, Prevette D, Scott SA, Wang G, et al. In vivo analysis of Schwann cell programmed cell death in the embryonic chick: regulation by axons and glial growth factor. J Neurosci Jun. 1, 2002;22(11):4509-4521.

Bryan DJ, Holway AH, Wang KK, Silva AE, Trantolo DJ, Wise D, et al. Influence of glial growth factor and Schwann cells in a bioresorbable guidance channel on peripheral nerve regeneration. Tissue Eng Apr. 2000;6(2):129-138.

Zurn AD, Winkel L, Menoud A, Djabali K, Aebischer P. Combined effects of GDNF, BDNF, and CNTF on motoneuron differentiation in vitro. J Neurosci Res Apr. 15, 1996;44(2)133-141.

Bailey SB, Eicheler ME, Villadiego A, Rich KM. The influence of fibronectin and laminin during Schwann cell migration and peripheral nerve regeneration through silicon chambers. J Neurocytol Mar. 1993;22(3):176-184.

Woolley AL, Hollowell JP, Rich KM. First place Resident Basic Science Award 1990. Fibronectin-laminin combination enhances peripheral nerve regeneration across long haps. Otolaryngol Head Neck Surg Oct. 1990;103(4):509-518.

Dertinger SK, Jiang X, Li Z , Murthy VN, Whitesides GM. Gradients of substrate-bound laminin orient axonal specification of neurons. Proc Natl Acad Sci U S A Oct. 1, 2002;99(20):12542-12547.

Li GN, Liu J, Hoffman-Kim D. Multi-molecular gradients of permissive and inhibitory cues direct neurite outgrowth. Ann Biomed Eng Jun. 2008;36(6):889-904.

Sta Iglesia DD, Cragoe EJ, Jr., Vanable JW, Jr. Electric field strength and epithelization in the newt (*Notophthalmus viridescens*). J Exp Zool Jan. 1, 1996;274(1):56-62.

Sta Iglesia DD, Vanalbe JW, Jr. Endogenous lateral electric fields around bovine corneal lesions are necessary for and can enhance normal rates of wound healing. Wound Repair Regen Nov.-Dec. 1998;6(6):531-542.

Song B, Zhao M, Forrester J, McCaig C. Nerve regeneration and wound healing are stimulated and directed by an endogenous electrical field in vivo. Journal of Cell Science 2004;117(20):4681-4690.

Chiang M, Robinson KR, Vanable JW, Jr. Electrical fields in the vicinity of epithelial wounds in the isolated bovine eye. Exp Eye Res Jun. 1992;54(6):999-1003.

Huang J, Hu X, Lu L, Ye Z, Zhang Q, Luo Z. Electrical regulation of Schwann cells using conductive polypyrrole/chitosan polymers. J Biomed Mater Res A Jun. 17, 2009.

Supronowicz PR, Ajayan PM, Ullmann KR, Arulanandam BP, Metzger DW, Bizios R. Novel current-conducting composite substrates for exposing osteoblasts to alternating current stimulation. J Biomed Mater Res Mar. 5, 2002;59(30):499-506.

Borgens RB, Vanable JW, Jr. Jaffe LF. Bioelectricity and regeneration: large currents leave the stumps of regenerating newt limbs. Proc Natl Acad Sci U S A Oct. 1977;74(10):4528-4532.

Al-Majed AA, Neumann CM, Brushart TM, Gordon T. Brief electrical stimulation promotes the speed and accuracy of motor axonal regeneration. J Neurosci Apr. 1, 2000;20(7):2602-2608.

Marsh G, Beams HW. In Vitro Contorl of Growing Chick Nerve Fibers by Applied Electric Currents. Journal of Cellular and Comparative Physiology 1946;27:139-157.

Macias MY, Battocletti JH, Sutton CH, Pintar FA, Maiman DJ. Directed and enhanced neurite growth with pulsed magnetic field stimulation. Bioelectromagnetics May 2000;21(4):272-286.

Zhao M, Dick A, Forrester JV, McCaig CD. Electric field-directed cell motility involves up-regulated expression and asymmetric redistribution of the epidermal growth factor receptors and is enhanced by fibronectin and laminin. Molecular Biology of the Cell 1999;10(4):1259-1276.

Rajnicek AM, Robinson KR, McCaig CD. The direction of neurite growth in a weak DC electric field depends on the substratum: Contributions of adhesivity and net surface charge. Dev Biol Nov. 1998;203(2):412-423.

McCaig CD, Sangster L, Stewart R. Neurotrophins enhance electric field-directed growth cone guidance and directed nerve branching. Dev Dyn Mar. 2000;217(3):299-308.

Evans PJ, Bain JR, Mackinnon SE, Makino AP, Hunter DA. Selective reinnervation: a comparison of recovery following microsuture and conduit nerve repair. Brain Res Sep. 20, 1991;559(2):315-321.

Wang S, Cai Q, Hou J, Bei J, Zhang T, Yang J, et al. Acceleration effect of basic fibroblast growth factor on the regeneration of peripheral nerve through a 15-mm gap. J Biomed Mater Res A Sep. 1, 2003;66(3):522-531.

Vleggeert-Lankamp CL. The role of evaluation methods in the assessment of peripheral nerve regeneration through synthetic conduits: a systematic review. Laboratory investigation. J Neurosurg Dec. 2007; 107(6):1168-1189.

Chamberlain LJ, Yannas IV, Hsu HP, Strichartz GR, Sepctor M. Near-terminus axonal structure and function following rat sciatic nerve regeneration through a collagen-GAG matrix in a ten-millimeter gap. J Neurosci Res Jun. 1, 2000;610(5):666-677.

Fine EG, Decosterd I, Papaloizos M, Zurn AD, Aebischer P. GDNF and NGF released by synthetic guidance channels support sciatic nerve regeneration across a long gap. Eur J Neurosci Feb. 2002;15(4):589-601.

Udina E, Furey M, Busch S, Silver J, Gordon T, Fouad K. Electrical stimulation of intact peripheral sensory axons in rats promotes outgrowth of their central projections. Exp Neurol Mar. 2008;210(1):238-247.

Al-Majed AA, Brushart TM, Gordon T. Electrical accelerates and increases expression of BDNF and trkB Mrna in regenerating rat femoral motoneurons. Eur J Neurosci Dec. 2000;12(12):4381-4390.

Al-Majed AA, Tam SL, Gordon T. Electrical stimulation accelerates and enhances expression of regeneration-associated genes in regenerating rat femoral motoneurons. Cell Mol Neurobiol Jun. 2004;24(3):379-402.

Zhang J, Lineaweaver WC, Oswald T, Chen Z, Zhang F. Ciliary neurotrophic factor for acceleration of peripheral nerve regeneration: an experimental study. J Reconstr Microsurg May 2004;20(4):323-327.

Varejao AS, Melo-Pinto P, Meek MF, Filipe VM, Bulas-Cruz J. Methods for the experimental functional assessment of rat sciatic nerve regeneration. Neurol Res Mar. 2004;26(2):186-194.

Varejao AS, Cabrita AM, Geuna S, Melo-Pinto P, Filipe VM, Gramsbergen A, et al. Toe out angle: a functional index for the evaluation of sciatic nerve recovery in the rat model. Exp Neurol Oct. 2003;183(20):695-699.

Song YX, Muramatsu K, Kurokawa Y, Kuriyama R, Sakamoto S, Kaneko K, et al. Functional recovery of rat hind-limb allografts. J Reconstr Microsurg Oct. 2005;21(7):471-476.

Bain JR, Mackinnon SE, Hunter DA. Functional evaluation of complete sciatic, peroneal, and posterior tibial nerve lesions in the rat. Plast Reconstr Surg Jan. 1989;83(1):129-138.

(56) References Cited

OTHER PUBLICATIONS

Luis AL, Rodrigues JM, Lobato JV, Lopes MA, Amado S, Veloso AP, et al. Evaluation of two biodegradable nerve guides for the reconstruction of the rat sciatic nerve. Biomed Mater Eng 2007;17(1):39-52.

Gonzalez-Billault C, Jimenez-Mateos EM, Caceres A, Diaz-Nido J, Wandosell F, Avila J. Microtube-associated protein 1B function during normal development, regeneration, and pathological conditions in the nervous system. J Neurobiol Jan. 2004;58(1):48-59.

Pigino G, Paglini G, Ulloa L, Avila J, Caceres A. Analysis of the expression, distribution and function of cyclin dependent kinase 5 (cdk5) in developing cerebellar macroneurons. J Cell Sci Jan. 1997;110 (Pt 2):257-270.

Franzen R, Tanner SL, Dashiell SM, Rottkamp CA, Hammer JA, Quarles RH. Microtubule-associated protein 1B: a neuronal binding partner for myelin-associated glycoprotein. J Cell Biol Dec. 10, 2001;155(6):893-898.

Riederer BM, Moya F, Calvert R. Phosphorylated MAP1b, alias MAP5 and MAP1x, is involved in axonal growth and neuronal mitosis. Neuroreport Jun. 1993;4(6):771-774.

Bouquet C, Ravaille-Veron M, Propst F, Nothias F. MAP1B coordinates microtubule and actin filament remodeling in adult mouse Schwann cell tips and DRG neuron growth cones. Mol Cell Neurosci Oct. 2007;36(2):235-247.

Garcia-Perez J, Avila J, Diaz-Nido J. Implication of cyclin-dependent kinases and glycogen synthase kinase 2 in the phosphorylation of microtubule-associated protein 1B in developing neuronal cells. J Neurosci Res May 15, 1998;52(4):445-452.

Goold RG, Gordon-Weeks PR. The MAP kinase pathway is upstream of the activation of GSK3beta that enables it to phosphorylate MAP1B and contributes to the stimulation of axon growth. Mol Cell Neurosci Mar. 2005;28(3):524-534.

Goold RG, Gordon-Weeks PR. Glycogen synthase kinase 3beta and the regulation of axon growth. Biochem Soc Trans Nov. 2004;32(Pt 5):809-811.

Goold RG, Gordon-Weeks PR. NGF activates the phosphorylation of MAP1B by GSK3beta through the TrkA receptor and not the p75(NTR) receptor. J Neurochem Nov. 2003;87(4):935-946.

Cheng C, Webber CA, Wang J, Xu Y, Martinez JA, Liu WQ, et al. Activated RHOA and peripheral axon regeneration. Exp Neurol Aug. 2008;212(2):358-369.

Gallo G. RhoA-kinase coordinates F-actin organization and myosin II activity during semaphoring-3A-induced axon retraction. J Cell Sci Aug. 15, 2006;119(Pt 16):3413-3423.

Loudon RP, Silver LD, Yee HF, Jr., Gallo G. RhoA-kinase and myosin II are required for the maintenance of growth cone polarity and guidance by nerve growth factor. J Neurobiol Jul. 2006;66(8):847-867.

Melendez-Vasquez CV, Einheber S, Salzer JL. Rho kinase regulates Schwann cell myelination and formation of associated axonal domains. J Neurosci Apr. 21, 2004;24(16):3953-3963.

Sherman DL, Brophy PJ. Mechanisms of axon ensheathment and myelin growth. Nat Rev Neurosci Sep. 2005;6(9):683-690.

Sharma N, Marzo SJ, Jones KJ, Foecking EM. Electrical stimulation and testosterone differentially enhance expression of regeneration-associated genes. Exp Neurol May 7, 2009.

Tsujino H, Kondo E, Fukuoka T, Dai Y, Tokunaga A, Miki K, et al. Activating transcription factor 3 (ATF3) induction by axotomy in sensory and motoneurons: A novel neuronal marker of nerve injury. Mol Cell Neurosci Feb. 2000;15(2):170-182.

Geremia NM, Gordon T, Brushart TM, Al-Majed AA, Verge VM. Electrical stimulation promotes sensory neuron regeneration and growth-associated gene expression. Exp Neurol Jun. 2007;205(2):347-359.

McIntyre CC, Richardson AG, Grill WM. Modeling the excitability of mammalian nerve fibers: influence of afterpotentials on the recovery cycle. J Neurophysiol Feb. 2002;87(2):995-1006.

Shanthaveerappa TR, Bourne GH. Histological and histochemical studies of the choroid of the eye and its relations to the pia-arachnoid mater of the central nervous system and perineural epithelium of the peripheral nervous system. Acta Anat (Basel) 1965;61(3):379-398.

Jana NR, Gearheart L, Murphy CJ. Wet chemical synthesis of high aspect ratio cylindrical gold nanorods. J Phys Chem B May 2001;105(19):4065-4067.

Johnson EO, Soucacos PN. Nerve repair: experimental and clinical evaluation of biodegradable artificial nerve guides. Injury Sep. 2008;39 Suppl 3:S30-36.

Hudson TW, Evans GR, Schmidt CE. Engineering strategies for peripheral nerve repair. Orthop Clin North Am Jul. 2000;31(3):485-498.

Wang S, Yaszemski MJ, Knight AM, Gruetzmacher JA, Currier BL, Yaszemski MJ. Synthesis and characterizations of biodegradable and crosslinkable poly(epsilon-caprolactone fumarate), poly(ethylene glycol fumarate), and their amphiphilic copolymer. Biomaterials Feb. 2006;27(6):832-841.

Wang S, Yaszemski MJ, Knight AM, Gruetzmacher JA, Windebank AJ, Lu L. Photo-crosslinked poly(epsilon-caprolactone fumarate) networks for guided peripheral nerve regeneration: material properties and preliminary biological evaluations. Acta Biomater Jun. 2009;5(5):1531-1542.

Hadlock T, Sundback C, Hunter D, Cheney M, Vacanti JP. A polymer foam conduit seeded with Schwann cells promotes guided peripheral nerve regeneration. Tissue Engineering 2000;6(20)119-127.

Chang CJ, Hsu SH, Yen HJ, Chang H, Hsu SK. Effects of unidirectional permeability in asymmetric poly(DL-lactic acid-co-glycolic acid) conduits on peripheral nerve regeneration: An in vitro and in vivo study. J Biomed Mater Res Part B Oct. 2007;83B(1):206-215.

Hollowell JP, Villadiego A, Rich KM. Sciatic nerve regeneration across gaps within silicone chambers: long-term effects of NGF and consideration of axonal branching. Exp Neurol Oct. 1990;110(1):45-51.

Lietz M, Dreesmann L, Hoss M, Oberhoffner S, Schlosshauer B. Neuro tissue engineering of glial nerve guides and the impact of different cell types. Biomaterials Mar. 2006;27(8):1425-1436.

Song J, Cheng Q, Kopta S, Stevens RC. Modulating artificial membrane morphology: pH-induced chromatic transition and nanostructural transformation of a bolaamphiphilic conjugated polymer from blue helical ribbons to red nanofibers. J Am Chem Soc Apr. 11, 2001;123(14):3205-3213.

Kehoe S, Zhang XF, Boyd D. FDA approved guidance conduits and wraps for peripheral nerve injury: A review of materials and efficacy. Injury-Int J Care Inj May;43(5):553-572.

Pomerantseva I, Krebs N, Hart A, Neville CM, Huang AY, Sundback CA. Degradation behavior of poly(glycerol sebacate). J Biomed Mater Res Part A Dec. 2009;91A(4):1038-1047.

Wang YD, Ameer GA, Sheppard BJ, Langer R. A tough biodegradable elastomer. Nature Biotechnology Jun. 2002;20(6):602-606.

Nijst CLE, Bruggeman JP, Karp JM, Ferreira L, Zumbuehl A, Bettinger CJ, et al. Synthesis and characterization of photocurable elastomers from poly(glycerol-co-sebacate). Biomacromolecules Oct. 2007;8(10):3067-3073.

Gerecht S, Townsend SA, Pressler H, Zhu H, Nijst CLE, Bruggeman JP, et al. A porous photocurable elastomer for cell encapsulation and culture. Biomaterials Nov. 2007;28(32):4826-4835.

Svennersten K, Bolin MH, Jager EWH, Berggren M, Richter-Dahlfors A. Electrochemical modulation of epithelia formation using conducting polymers. Biomaterials Nov. 2009;30(31):6257-6264.

Luo XL, Weaver CL, Zhou DD, Greenberg R, Cui XYT. Highly stable carbon nanotube doped poly(3,4-ethylenedioxythiophene) for chronic neural stimulation. Biomaterials Aug;32(24):5551-5557.

Abidian MR, Martin DC. Experimental and theoretical characterization of implantable neural microelectrodes modified with conducting polymer nanotubes. Biomaterials Mar. 2008;29(9):1273-1283.

Edwards SL, Church JS, Werkmeister JA, Ramshaw JAM. Tubular micro-scale multiwalled carbon nanotube-based scaffolds for tissue engineering. Biomaterials Mar. 2009;30(9):1725-1731.

(56) References Cited

OTHER PUBLICATIONS

Shi GX, Rouabhia M, Wang ZX, Dao LH, Zhang Z. A novel electrically conductive and biodegradable composite made of polypyrrole nanoparticles and polylactide. Biomaterials Jun. 2004;25(13):2477-2488.
George PM, Lyckman AW, LaVan DA, Hegde A, Leung Y, Avasare R, et al. Fabrication and biocompatibility of polypyrrole implants suitable for neural prosthetics. Biomaterials Jun. 2005;26(17):3511-3519.
Ifkovits JL, Devlin JJ, Eng G, Martens TP, Vunjak-Novakovic G, Burdick JA. Biodegradable Fibrous Scaffolds with Tunable Properties Formed from Photo-Cross-Linkable Poly(glycerol sebacate). ACS Appl Mater Interfaces Sep. 2009;1(9):1878-1886.
Liu QY, Tian M, Ding T, Shi R, Feng YX, Zhang LQ, et al. Preparation and characterization of a thermoplastic poly(glycerol sebacate) elastomer by two-step method. J Appl Polym Sci Feb. 2007;103(3):1412-1419.
Evans GR. Challenges to nerve regeneration. Semin Surg Oncol Oct.-Nov. 2000;19(3):312-318.
Chamberlain LJ, Yannas IV, Hsu HP, Strichartz GR, Spector M. Near-terminus axonal structure and function following rat sciatic nerve regeneration through a collagen-GAG matrix in a ten-millimeter gap. J Neurosci Res Jun. 1, 2000;60(5):666-677.
Zhang DH, Kandadai MA, Cech J, Roth S, Curran SA. Poly(L-lactide) (PLLA)/multiwalled carbon nanotube (MWCNT) composite: Characterization and biocompatibility evaluation. J Phys Chem B 2006;110(26):12910-12915.
Schense JC, Bloch J, Aebischer P, Hubbell JA. Enzymatic incorporation of bioactive peptides into fibrin matrices enhances neurite extension. Nature Biotechnology Apr. 2000;18(4):415-419.
Chen YS, Hsieh CL, Tsai CC, Chen TH, Cheng WC, Hu CL, et al. Peripheral nerve regeneration using silicone rubber chambers filled with collagen, laminin and fibronectin. Biomaterials Aug. 2000;21(15):1541-1547.
Evans GRD, Brandt K, Katz S, Chauvin P, Otto L, Bogle M, et al. Bioactive poly(L-lactic acid) conduits seeded with Schwann cells for peripheral nerve regeneration. Biomaterials Feb. 2002;23(3):841-848.
Goldner JS, Bruder JM, Li G, Gazzola D, Hoffman-Kim D. Neurite bridging across micropatterned grooves. Biomaterials Jan. 2006;27(3):460-472.
Abrams GA, Goodman SL, Nealey PF, Franco M, Murphy CJ. Nanoscale topography of the basement membrane underlying the corneal epithelium of the rhesus macaque. Cell Tissue Res Jan. 2000;299(1):39-46.
Miller C, Jeftinija S, Mallapragada S. Micropatterned Schwann cell-seeded biodegradable polymer substrates significantly enhance neurite alignment and outgrowth. Tissue Engineering Dec. 2001;7(6):705-715.
Zhao M, AgiusFernandez A, Forrester JV, McCaig CD. Orientation and directed migration of cultured corneal epithelial cells in small electric fields are serum dependent. Journal of Cell Science Jun. 1996;109:1405-1414.
Zhao M, McCaig CD, AgiusFernandez A, Forrester JV, ArakiSasaki K. Human corneal epithelial cells reorient and migrate cathodally in a small applied electric field. Current Eye Research 1997;16(10):973-984.
Baron-Van Evercooren A, Kleinman HK, Ohno S, Marangos P, Schwartz JP, Dubois-Dalcq ME. Nerve growth factor laminin and fibronective promote neurite growth in human fetal sensory ganglia cultures. Journal of Neuroscience Research 1982;8(2-3):179-194.
Cheng H, Hoffer B, Stromberg I, Russell D, Olson L. The effect of glial-cell line-derived neurotrophic factor in fibrin glue on developing dopamine neurons. Exp Brain Res May 1995;104(2):199-206.
Edelman ER, Mathiowitz E, Langer R, Klagsbrun M. Controlled and modulated release of basic fibroblast growth factor. Biomaterials Sep. 1991;12(7):619-626.
Phillips,J.B., Bunting, S.C.J., Hall,S.M. & Brown, R.A. Neural tissue engineering: A self-organizing collagen guidance conduit. Tissue Engineering 11, 1611-1617 (2005).
Jubran,M. & Widenfalk, J. Repair of peripheral nerve transections with fibrin sealant containing neurotrophic factors. Experimental Neurology 181, 204-212 (2003).
Foley,J.D., Grunwald, E.W., Nealey, P.F. & Murphy, C.J. Cooperative modulation of neuritogenesis by PC12 cells by topography and nerve growth factor. Biomaterials 26, 3639-3644 (2005).
Yusuka Katayama et al. Coil-Reinforced hydrogel tubes promote nerve regeneration equivalent to that of nerve autografts. Biomaterials 27, 503-518 (2006).
Yuan, Y., Zhang, P., Yang, Y., Wang, X. & Gu, X. The interaction of Schwann cells with chitosan membranes and fibers in vitro. Biomaterials 25, 4273-4278 (2004).
Evans, G.R.D. et al. In vivo evaluation of poly(-lactic acid) porous conduits for peripheral nerve regeneration. Biomaterials 20, 1109-1115 (1999).
Lietz, M. et al. Physical and biological performance of a novel block copolymer nerve guide. Biotechnology and Bioengineering 93, 99-109 (2006).
Keilhoff,G., Stang, F., Wolf, G. & Fansa, H. Bio-compatibility of type I/III collagen matrix for peripheral nerve reconstruction. Biomaterials 24, 2779-2787 (2003).
Jain, A., Kim, Y.T., Mckeon, R.J. & Bellamkonda, R.V. In situ gelling hydrogels for conformal repair of spinal cord defects, and local delivery of BDNF after spinal cord injury. Biomaterials 27, 497-504 (2006).
Li, M., Guo, Y., Wei, Y., MacDiarmid, A.G. & Lelkes, P.I. Electrospinning polyaniline-contained gelatin nanofibers for tissue engineering applications. Biomaterials 27, 2705-2715 (2006).
Novikova,L.N. et al. Alginate hydrogel and matrigel as potential cell carriers for neurotransplantation. Journal of Biomedical Materials Research Part A 77A, 242-252 (2006).
Al Majed, A.A., Tam, S.L. & Gordon, T. Electrical stimulation accelerates and enhances expression of regeneration-associated genes in regenerating rat femoral motoneurons. Cellular and Molecular Neurobiology 24, 379-402 (2004).
Brushart, T.M., Jari, R., Verge, V., Rohde, C. & Gordon, T. Electrical stimulation restores the specificity of sensory axon regeneration. Experimental Neurology 194, 221-229 (2005).
Ming, G.l., Henley, J., Tessier-Lavigne, M., Song, H.J. & Poo, M.m. Electrical Activity Modulates Growth Cone Guidance by Diffusible Factors. Neuron 29, 441-452 (2001).
Terell Rivers, Terry Hudson & Christine Schmidt. Synthesis of a Novel, Biodegradable Electrically Conducting Polymer for Biomedical Applications. Advanced Functional Materials 12, 33-37 (2002).
Kotwal, A. & Schmidt, C.E. Electrical stimulation alters protein adsorption and nerve cell interactions with electrically conducting biomaterials. Biomaterials 22, 1055-1064 (2001).
Yang, L., Feng, J.K. & Ren, A.M. Structural, electronic and optical properties of a series of oligofluorene-thiophene oligomers and polymers. Journal of Molecular Structure—Theochem 758, 29-39 (2006).
Suzuki, M., Fukuyama, M., Hori, Y. & Hotta, S. Electroluminescent features of oligothiophenes dispersed as a dopant in host matrices. Journal of Applied Physics 91, 5706-5711 (2002).
Xu, H. et al. High-performance field-effect transistors based on Langmuir-Blodgett films of cyclo[8]pyrrole. Langmuir 21, 5391-5395 (2005).
Jin, Z., Pramoda, K.P., Xu, G. & Goh, S.H. Dynamic mechanical behavior of meltprocessed multi-walled carbon nanotubelpoly(methyl methacrylate) composites. Chemical Physics Letters 337, 43-47 (2001).
Webster, T.J., Waid, M.C., McKenzie, J.L., Price, R.L. & Ejiofor, J.U. Nanobiotechnology: carbon nanofibres as improved neural and orthopaedic implants. Nanotechnology 15, 48-54 (2004).
Wei, G. et al. One-step synthesis of silver nanoparticles, nanorods, and nanowires on the surface of DNA network. Journal of Physical Chemistry B 109, 8738-8743 (2005).

(56) References Cited

OTHER PUBLICATIONS

Murphy, C.J., Gole, A.M., Hunyadi, S.E. & Orendorff, C.J. One-dimensional colloidal gold and silver nanostructures. Inorganic Chemistry 45,7544-7554 (2006).
Orendorff, C.J., Gearheart, L., Jana, N.R. & Murphy, C.J. Aspect ratio dependence on surface enhanced Raman scattering using silver and gold nanorod substrates. Physical Chemistry Chemical Physics 8, 165-170 (2006).
Elias, K.L., Price, R.L. & Webster, T.J. Enhanced functions of osteoblasts on nanometer diameter carbon fibers. Biomaterials 23, 3279-3287 (2002).
Hu, H. et al. Polyethyleneimine functionalized single-walled carbon nanotubes as a substrate for neuronal growth. Journal of Physical Chemistry B 109, 4285-4289 (2005).
Mattson, M.P., Haddon, R.C. & Rao, A.M. Molecular functionalization of carbon nanotubes and use as substrates for neuronal growth. Journal of Molecular Neuroscience 14, 175-182 (2000).
Ni, Y.C. et al. Chemically functionalized water soluble single-walled carbon nanotubes modulate neurite outgrowth. Journal of Nanoscience and Nanotechnology 5, 1707-1712 (2005).
Lansdown, A.B.G. Critical observations on the neurotoxicity of silver. Critical Reviews in Toxicology 37, 237-250 (2007).
Schmidt, C.E. Ann Rev Biomed Engr 5:293-347 (2003).
Rosenbalm, T., Levi-Polyachenko, N., and Wagner, W.D. Development of repeated biphasic conducting materials for peripheral nerve repair. Gordon Conference on Biochemistry, The Complex Membrane of the Electric Field, University of New England, Biddeford, ME (Jul. 11-16, 2010).
Oh, et al. High molecular weight soluble polypyrrole. Synthetic Metals 125: 267-272 (2002).
Taunk, M. et al. Hopping and tunneling transport over a wide temperature range in chemically synthesized doped and undoped polypyrrole. Solid State Communications 150: 1766-1769 (2010).
Yen, S-J et al. Preparation and characterization of polypyrrole/magnetite nanocomposites synthesized by in situ chemical oxidative polymerization. Journal of Polymer Sciences B: Polymer Physics 46: 1291-1300 (2008).
Lu, X. et al. Preparation and characterization of conducting polycaprolactone/chitosan/polypyrrole composites. Composites: Part A. 41: 1516-1523 (2010).
Oh, S.H. et al. Peripheral nerve regeneration within an asymmetrically porous PLGA/Pluronic F127 nerve guide conduit. Biomaterials 29: 1601-1609 (2008).
Oh, E.J. et al. Synthesis and characterization of high molecular weight, highly soluble polypyrrole in organic solvents. Synthetic Metals 119: 109-110 (2001).
Shi, G. et al. A novel electrically conductive and biodegradable composite made of polypyrrole nanoparticles and polylactide. Biomaterials 25: 2477-2488 (2004).
Thomas, C.A. et al. Poly(3,4-alkylenedioxypyrrole)s as highly stable aqueous-compatible conducting polymers with biomedical implications. Adv. Mater 12: 222 (2000).
Wan, Y. et al. Porous-conductive chitosan scaffolds for tissue engineering II. in vitro and in vivo degradation. Journal of Materials Science: Materials in Medicine 16: 1017-1028 (2005).
Wan, Y. et al. Porous-Conductive Scaffolds for Tissue Engineering, 1: Preparation and Characterization. Macromol. Biosci. 4: 882-890 (2004).
Wang, Z. et al. In vivo evaluation of a novel electrically conductive polypyrrole/poly(D,L-lactide) composite and polypyrrole-coated poly(D,L-lactide-co-glycolide) membranes. J. Biomed Mater Res 70A: 28-38 (2004).
Yan, F. et al. Preparation of electrically conducting polypyrrole in oil/water microemulsion. J Appl Polym Sci 77: 135-140 (2000).

Stryker. Stryker Neuromatrix. 2009; Available from: http://www.stryker.com/en-us/products/Trauma/PeripheralNerveRepair/NeuroMatrix/index.htm.
Integra. NeuraGen Nerve Guide. 2009; Available from: http://www.integra-ls.com/products/?product=88.
Stryker. Stryker Neuroflex. 2009; Available from: http://www.stryker.com/en-us/products/Trauma/PeripheralNerveRepair/Neuroflex/index.htm.
Polyganics. Neurolac. 2009; Available from: http://www.polyganics.nl/index.php?id=19.
Synovis Micro Companies Alliance I. GEM Neurotube. 2009; Available from: http://www.synovismicro.com/gem_neurotube.php.
Integra. NeuraWrap Nerve Protector. 2009; Available from: http://www.integra-ls.com/products/?product=198.
SaluMedica. SaluBridge Physician Information. 2009; Available from: http://www.salumedica.com/salubridgeinfodoc.htm.
McDonald, D.S. & Zochodne, D.W. An injectable nerve regeneration chamber for studies of unstable soluble growth factors. Journal of Neuroscience Methods 122, 171-178 (2003).
Banani Kundu et al., Thromboelastometric and platelet responses to silk biomaterials, Scientific Reports, pp. 1-9, May 2014.
R. W. Farndale et al., The role of collagen in thrombosis and hemostasis, Journal of Thrombosis and Haemostasis, 2: 561-573.
Nei Wu, Ph.D. et al., Artificial Niche Combining Elastomeric Substrate and Platelets Guides Vascular Differentiation of Bone Marrow Mononuclear Cells, Tissue Engineering: Part A vol. 17, Nos. 15 and 16, 2011.
Tao Xua, et al., Viability and electrophysiology of neural cell structures generated by the inkjet printing method, Biomaterials 27 (2006) 3580-3588, Jan. 2006.
Scott J.Hollister, Porous scaffold design for tissue engineering, Nature Materials vol. 4 Jul. 2005.
Journal of pressure ulcer, 2012, vol. 14, No. 1, p. 43-48.
Dong, et al.; Performance of an in situ formed bioactive hydrogel dressing from a PEG-based hyperbranched multifunctional copolymer; Acta Biomaterialia; 10 (2014) 2076 2085.
Moues et al.,; The role of topical negative pressure in wound repair: Expression of biochemical markers in wound fluid during wound healing; Wound Repair and Regeneration; pp. 448-494.
Seol et al.; Biocompatibility and preclinical feasibility tests of a temperature-sensitive hydrogel for the purpose of surgical wound pain control and cartilage; repair Journal of Biomedical Materials Research B: Applied Biomaterials | Nov. 2013 vol. 101B, Issue 8; pp. 1508-1515.
Casper el al. "Coating Electrospun Collagen and Gelatin Fibers with Perlecan Domain I for Increased Growth Factor Binding" Biomacromolecules, vol. 8 Issue 4 (Feb. 28, 2007): pp. 1116-1123.
Zhang et al. "In vitro evaluation of electrospun silk fibroin scaffolds for vascular cell growth" Biomalerials, vol. 29 Issue 14 (Feb. 14, 2008): pp. 2217-2227.
Yu et al. "The effect of strornal cell-derived factor-1a/heparin coating of biodegradable vascular grafts on the recruitment of both endothelial and smooth muscle progenitor cells for accelerated regeneration" Biomaterials, vol. 33 Issue 32 (Aug. 11, 2012): pp. 8062-8074.
Lee et al. "Nanofiber alignment and direction of mechanical strain affect the ECM production of human ACL fibroblast" Biomaterials, vol. 26 Issue 11 (Jun. 11, 2004): pp. 1261-1270.
Yeo et al. "Collagen-Based Biomimetic Nanofibrous Scaffolds: Preparation and Characterization of Collagen/Silk Fibroin Bicomponent Nanofibrous Structures" Biomacromolecules, vol. 9 Issue 4 (Mar. 8, 2008): pp. 1106-1116.
Zhou et al. "Electrospinning of silk fibroin and collagen for vascular tissue engineering" International Journal of Biological Macromolecules, vol. 47 Issue 4 (Aug. 3, 2010): pp. 514-519.

* cited by examiner

NEW SHEET

NANOFIBER-BASED GRAFT FOR HEART VALVE REPLACEMENT AND METHODS OF USING THE SAME

REFERENCE TO RELATED APPLICATIONS

This application is a 371 application of International Application No. PCT/US2013/066747, filed Oct. 25, 2013, which claims the benefit of U.S. Provisional Application No. 61/718,991, filed Oct. 26, 2012, the entirety of which are incorporated by reference herein.

FIELD OF THE INVENTION

The present invention relates generally to electrospun nanofiber-based biomaterials useful for wound repair and tissue replacement and, more particularly, but not exclusively to electrospun composite materials comprising fibroin for tissue engineering applications, particularly heart valve replacement.

BACKGROUND OF THE INVENTION

Severe valvular heart disease (VHD) affects 1 out of 40 adults in the United States, and is responsible for approximately 28,000 deaths per year. Aortic valves consist of 3 film-like cusps with an average thickness of 300-700 µm. The main composition of the valvular extracellular material (ECM) is type I collagen and elastin in a 4:1 dry weight ratio which orchestrate the passive opening and closing of the aortic leaflets to direct blood flow. Dysfunctional heart valves are life-threatening as the diseased valvular tissues are unable to perform the normal physiological requirements. Among all VHD, aortic valve disease has a mortality rate of about 65%. The treatment usually necessitates surgical replacement by mechanical or tissue bioprosthetic valves. Commonly used mechanical heart valves have adequate durability but are often thrombogenic and require life-long anti-coagulant therapy. Bioprosthetic collagen-based tissue valves from porcine valves or bovine pericardium mimic the anatomy of native valves, however, early valve degeneration, and 50% postoperative failure occur within 12-15 years. Therefore, a nonthrombogenic and durable alternative is desperately needed in the field.

Successful heart valve grafts should be both durable and functional. Basic anatomical and physiological requirements need to be considered to fabricate structurally similar and mechanically robust synthetic heart valve grafts. Approaches to overcome the pathological failure modes should be taken into consideration in order to select graft composites that are biocompatible, slowly degradable and durable, capable of promoting adequate cell growth and tissue remodelling, while being non-thrombogenic.

SUMMARY OF THE INVENTION

The present invention provides a nonthrombogenic and durable alternative biomaterial for tissue replacement. In the present invention, collagen protein is blended with mechanically robust fibroin and a hemocompatible synthetic elastomeric polymer or elastomer to produce a multi-functional electrospun nanofibrous material suitable for tissue replacement and specifically, although not exclusively, heart valve replacement.

In a first aspect, the present invention encompasses a nonthrombogenic composition comprising collagen, fibroin, and a hemocompatible synthetic elastomer. In one embodiment, the collagen is type I collagen. In another embodiment, the fibroin is silk fibroin. In a further embodiment, the hemocompatible synthetic elastomer is a poly glycerol derivative ester comprising a polycarboxylic acid. In a most preferred embodiment, the poly glycerol derivative is poly (glycerol sebacate) (PGS).

In an additional aspect, the present invention encompasses an article of manufacture comprising collagen, fibroin, and a hemocompatible synthetic elastomer in fiber form.

In another aspect, the present invention encompasses a porous electrospun graft material which is readily configured to function as a tissue replacement. The graft comprises a collagen, a fibroin, and a hemocompatible synthetic elastomer. In one embodiment, the tissue to be replaced is heart tissue. In another embodiment, the graft is molded in the shape of a heart valve.

In yet another aspect, the present invention encompasses a graft for heart valve replacement, comprising a porous electrospun mat, the electrospun mat comprising poly glycerol polymer, fibroin and a polyglycerol derivative ester comprising a poly carboxylic acid.

In an additional aspect, the present invention encompasses a method of preparing a graft for heart valve replacement, where the method comprises the steps of: (a) preparing an electrospinning solution of collagen, fibroin and a hemocompatible synthetic elastomer; (b) electrospinning the electrospinning solution into an interconnected nanofiber matrix; and (c) collecting the interconnected nanofiber matrix to produce the graft for heart valve replacement.

The present invention provides electrospun grafts having superior mechanical properties, low degradation, and reduced thrombogenic potential compared to primarily collagen-based materials.

BRIEF DESCRIPTION OF THE DRAWINGS

The foregoing summary and the following detailed description of the exemplary embodiments of the present invention may be further understood when read in conjunction with the appended drawings, in which:

FIG. 10A and FIG. 10D: collagen gel, FIG. 10B and FIG. 10E collagen mat, FIG. 10C and FIG. 10F: PFC mat after 15 minutes of incubation with PRP. The images demonstrate the presence of a single layer of platelets on the PFC mat and minor platelet activation in comparison to activated platelets on the collagen mat and collagen gel (Magnification: 1500× for FIG. 10A, FIG. 10B, and FIG. 10C, scale bar: 10 µm; 5000× for FIG. 10D, FIG. 10E, and FIG. 10F, scale bar: 1 µm).

DETAILED DESCRIPTION OF THE INVENTION

Figure 1:
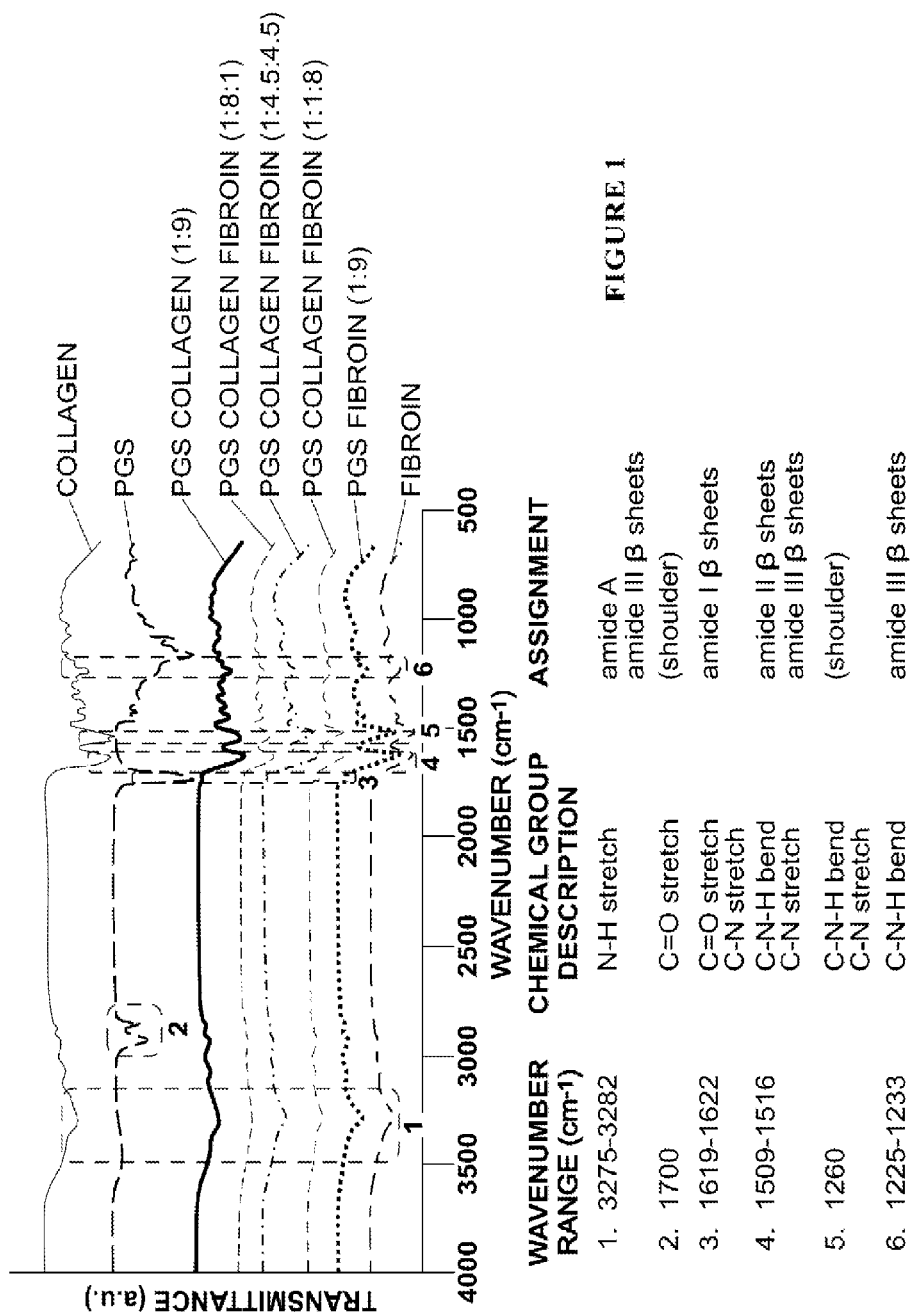
FIG. 1 depicts a FTIR spectra of collagen, PGS, fibroin and composites thereof.

Creating a functional heart valve graft that lasts a lifetime is one of the main objectives of cardiovascular tissue engineering. While conventional collagen-based heart valves have been used for many years, they eventually fail because of inadequate cell infiltration and insufficient replacement of graft material by tissue remodelling. To overcome graft failure due to inadequate tissue remodelling and growth, an improved graft material was created by incorporating collagen protein with mechanically robust silk fibroin, and a hemocompatible synthetic elastomer. Preferably, the hemocompatible synthetic elastomer is a polyglycerol derivative ester comprising a polycarboxylic acid. Most preferably, the polyglycerol derivative ester is poly (glycerol sebacate) (PGS). In one embodiment of the present invention demonstrates that electrospun grafts created from composites of collagen, particularly type I collagen, silk fibroin, and PGS are stable, less thrombogenic and easier to fabricate than the conventionally used collagen-based grafts for aortic heart valve replacement. Specifically, the goal of the present invention was to fabricate a graft material that mimics the composition, structure and mechanical properties of native tissue and to promote the formation of an intact nonthrombogenic endothelial cell layer. More specifically, the graft material mimics the composition, structure and mechanical properties of native heart valve tissue. In the present invention, an improved heart valve material composed of a collagen, a fibroin, and a hemocompatible synthetic elastomer (e.g., PGS) was developed comprising properties similar to those reported for native heart valves. Indeed, the homogeneity of blended composites is demonstrated using Fourier transform spectroscopy. Tensile stress, strain, and elastic modulus of the electrospun mats were measured by an Instron mechanical tester.

Functional tests of PFC mats demonstrate a slow degradation rate as compared to other collagen-based grafts. Cells adhere to and proliferate on PFC mats. Endothelial cells are observed to form tight junctions on the material. Several studies with isolated platelets demonstrate that PFC mats are less thrombogenic in comparison to collagen hydrogels and structurally similar to electrospun collagen mats. In summary, the present invention demonstrates that PFC mats provide strong, slowly degradable, and nonthrombogenic grafts that promote cell adhesion and growth. Accordingly, the PFC mats of the instant invention may be used as functional and durable heart valve replacement materials.

The focus of the present invention is to create a resorbable heart valve graft material which imitates the native aortic valve tissue based on protein compositions, elastic modulus, stress, and strain. The graft materials were tested for degradation, endothelium formation and platelet adhesion. Ultimately, after implantation in the body, the graft is expected to facilitate cell proliferation and ECM remodelling in order to generate a healthy heart valve capable of growing and lasting a life-time.

The standard criteria for creating heart valve grafts are to mimic the compositional and structural characteristics of native heart valve tissue. These can be summarized as a favorable surface for cell attachment, high porosity and interconnected network for nutrient transport and cell signalling, and mechanical strength for performing valvular function under physiological stress. Moreover, a consideration of cell proliferation, cell-cell/ECM interactions, and cell function such as the production of non-thrombogenic glycocalyx is essential.

Traditional tissue valve grafts demonstrate limited cell growth and ECM remodelling (Sacks, Schoen et al. 2009). Therefore, creating heart valve grafts which incorporate active cell binding sites, slow degradability, and maintenance of structural and mechanical integrity during the healing process are desperately needed.

There are well-established reasons for these needs: first, native host cells have to adhere and proliferate in order to deposit proteins such as collagen and elastin which eventually remodel the surrounding environment to form their own ECM. Then, slow degradation and material durability allows tissue remodelling to take place before the graft deteriorates. A balance between the losses of mechanical integrity associated with material degradation and the gains of mechanical strength by ECM deposition from cells is essential for a practical, synthetic graft material.

Advances in synthetic polymers and natural proteins provide new avenues to tailor biomaterials for accommodating the functionality of specific tissue types. Selection in both composites and structures should be taken into consideration based on anatomical specifications and physiological functions of a healthy heart valve. Moreover, selected materials must be durable and able to withstand hemodynamic stress.

Implanted biomaterials contribute to the maintenance and restoration of normal physiological function upon slow degradation while tissue remodelling and ingrowth takes place. A balance between the losses of mechanical integrity associated with material degradation and the gains of mechanical strength through deposition of ECM by cells can be achieved by appropriate material selection and fabrication.

In order to create a heart valve graft that meets the aforementioned criteria, a strategy of incorporating natural proteins with an elastomer was implemented. Collagen, fibroin and PGS possess key characteristics useful in constructing a graft material for potential use as a tissue replacement.

Type I Collagen. Specifically, among the natural proteins, collagen is the most abundant load-bearing component of aortic valve cusp, while elastin imparts flexibility to soft tissue. The fundamental unit of the fibrillar collagen is the triple helix. The triple helix is made up of 3 polypeptide chains that each are 1000 amino acid long with glycine-X-Y (Gly-X-Y) repeats (Alberts, Johnson et al. 2002; Malafaya, Silva et al. 2007). The amino acid sequences, such as RGD (Arg-Gly-Asp), DGEA (Asp-Gly-Glu-Ala) or GFOGER (Gly-Phe-Hyp-Gly-Glu-Arg) in type I collagen motifs specially binds to $\alpha 2\beta 1$ integrin to regulate cell adhesion (Gu and Masters 2010; Shekaran and Garcia 2011). As the major structural protein, type I collagen absorbs most of the stress during the closing of the aortic valve in diastole when the ventricle is filled with blood.

Poly (glycerol sebacate) (PGS). The polymer poly (glycerol-sebacate) (PGS) mimics the mechanical behavior of the ECM protein, elastin (Pomerantseva, Krebs et al. 2009). It has low elastic modulus and large elongation capacity that is similar to elastin in valvular ECM (Alberts, Johnson et al. 2002; Sant and Khademhosseini 2010). Most importantly PGS has been reported to promote synthesis of mature and organized elastin, as well as having a superior hemocompatibility over other synthetic polymers such as poly (1-lactide-co-glycolide) (PLGA) (Motlagh, Yang et al. 2006; Lee, Stolz et al. 2011). PGS was also reported to be biocompatible in vivo and in vitro. Endothelial cells and fibroblasts were viable when cultured with PGS (Wang, Ameer et al. 2002; Yi and LaVan 2008). Minimal inflammatory response and no fibrous collagen capsules were observed for PGS (Wang, Ameer et al. 2002). The elastic property and biocompatibility of PGS make it a potent biomaterial for cardiovascular tissue grafts.

Silk Fibroin. To improve the strength of graft material and incorporate slow degradability, silk fibroin was selected (Horan, Antle et al. 2005). The adjacent -(Ala-Gly)- repeated sequence forms polypeptide chains with molecular weights of 390 kDa (heavy chain) and 25 kDa (light chain). Serving as the structural and major protein in the silk, fibroin protein polypeptide chains have interchain hydrogen bonds that contribute to the special highly crystalline β-sheet conformation. Interchain hydrogen bonds in silk fibroin protein assemble the polypeptide chains into the highly crystalline β-sheet conformation which imparts a slow degradation rate. Degradation is defined as the breakdown of the materials and leads to changes in physical properties. The degradation rate of silk fibroin is controllable and may be modified to last from hours to years (Rockwood, Preda et al. 2011). By incorporating these properties of silk fibroin, the resulting graft material provides sufficient mechanical support and performs the physiological function of valve tissue. Extracellular matrix remodelling takes up to 20-weeks. The slow degradation rate allows maintenance of a durable functional graft before cell infiltration and growth can take place (Horan, Antle et al. 2005). This is particularly important for heart valve grafts due to their special requirements in functionality and durability.

Fibroin possesses greater tensile property than collagen but possesses little elasticity. Collagen has a multitude of cell binding motifs. PGS, for its part, provides elasticity. It was originally believed that the designed material would have better mechanical properties than reported biomaterials, decellularized valves, or decellularized heart muscle that have been used for valve replacement. The invention described herein was developed to improve the tensile and durability properties of biomaterials.

With regard to cell adhesion, it was theorized that there would be less cell adhesion due to replacement of collagen mass with fibroin based on the dilution of key cell binding peptides on the collagen molecule. In addition the presence of PGS in the formula should have provided hydrophobicity to the composite. Initially, lower cell binding in the PFC composite compared with similarly manufactured Type I collagen was expected. However, it was unexpectedly discovered that superior binding of cells to the PFC composite was realized.

Based on the greater binding and proliferation of cells, it was also expected that there would be a similar or significantly greater adhesion of platelets to the PFC compound to collagen. However, quite surprisingly, the opposite effect was observed, i.e., reduced numbers of platelets adherent to PFC compared to physically similar collagen nanofibers.

Describing the present invention in further detail, in certain embodiments, materials fabricated with varying weight ratios of collagen, fibroin, and PGS had elastic moduli between 2.3-5.0 Mpa; tensile stress ranging from 0.6 to 1.5 Mpa; and strain values between approximately 20%-70%, which were similar to reports for native heart valves. In a particular embodiment, the porous electrospun graft material configured to replace biological tissue of the instant invention comprises a collagen, a fibroin, and a hemocompatible synthetic elastomer, wherein the graft has a strain value of about 0.2 to 0.7 mm/mm or about 0.4 to 0.5 mm/mm. Mechanical and suture retention tests (a highest 0.32N pull-out force at the single-loop suture site) indicated electrospun mats with 4.5:4.5:1 collagen, fibroin, and PGS weight ratio (PFC fiber mats) were most similar to native heart valves. Over a 30 week period in vitro degradation of PFC mats was only 0.01% per week with no significant change in fiber diameter. Endothelial cells adhered to and proliferated on PFC mats, and formed tight cell-cell junctions. Platelets adhesion studies surprisingly showed 2.2-2.9 fold less platelet adhesion compared to collagen hydrogels and electrospun collagen mats, respectively.

Electrospinning Fabrication.

Electrospinning is a fabrication technique that is applied to rapidly create an ECM analogous graft. Moreover, electrospinning fabrication is able to provide nanofiber porous networks in the form of an ultra thin sheet for the application of making heart valve grafts. In other embodiments, a mold may be used to create electrospun grafts or other electrospun structures of different shapes in order to, for example, mimic different valve structures, prepare stents, or fabricate other biologically relevant structures.

Indeed, in addition to the composition, the structure of the material is another important design consideration. Large surface area and sufficient porosity allow cell adhesion, nutrient transport, and signal transmission to enhance cell response for tissue remodelling. Production of fibers having pre-determined diameters and alignments can be achieved by controlling electrospinning parameters such as solution viscosity, voltage, environmental humidity, and collector orientation (Sell, Wolfe et al. 2010). Polymer composites are dissolved in appropriate solvent such as 1,1,1,3,3,3-hexafluoro-2-propanol (HFP) to form the electrospinning solution. The electrospinning solution usually is loaded into a syringe that is placed on a pump to inject the solution at a constant rate. A high voltage power source is connected to a conductive syringe tip. A conductive collector is grounded on the opposite side to the syringe to create an electric field. Polymer solution at the syringe tip forms a small droplet called a Taylor cone. When the electrostatic force overcomes the surface tension of the polymer solution, jets of polymer solution travel toward the collector and form an interconnected fiber matrix. In practicing the present invention, collagen, fibroin and polyglycerol polymer are electrospun into an interconnected nanofiber matrix graft material.

Silk Fibroin Extraction.

Silk fibroin protein was extracted according to the published procedure with modifications (Rockwood et al. 2011). Raw silk was boiled in 2 L of 0.02 M $Na_2CO_3$ at 100° C. for 30 minutes, rinsed twice with $DDH_2O$, squeezed, and air dried. Fibroin was then dissolved in 5.0M $CaCl_2$, and centrifuged at 2000 g to remove precipitate and floating contaminants. The fibroin solution was dialyzed and lyophilized to obtain powder for electrospinning. The identity and purity of fibroin was confirmed by amino acid assay analysis (Lombardi et al. 1990; Schroeder et al. 1955; Zhou et al. 2001). The amino acid composition of extracted fibroin was identified as conforming to reported values (Schroeder et al. 1955). Major amino acids glycine, alanine, and serine comprised 82% of the total amino acids in contrast to sericin that has 11% glycine, 70% alanine, and 33% serine (Swiss-Prot accession number: PO7856).

The molecular weight of fibroin was determined using sodium dodecyl sulphate-polyacrylamide gel electrophoresis (SDS-PAGE) followed by staining with Coomassie blue (Horan et al. 2005). The heavy (390 kDa) and light (25 kDa) chains of fibroin were observed, while a 119 kDa band indicative of serine was absent.

Synthesis of PGS Prepolymer.

PGS prepolymer can be synthesized from glycerol and sebacic acid which have been approved by FDA for medical applications (Wang, Ameer et al. 2002). The synthesis procedure followed the reported standard method with modification (Wang, Ameer et al. 2002; Pomerantseva, Krebs et al. 2009). Briefly, sebacic acid was heated at 180° C. on an oil bath with nitrogen flow across the reaction flask for 10-20 minutes until all melted. An equimolar amount of warmed glycerol (60° C.) was added. Then the pressure was decreased by attaching to a vacuum (General Medical, Richmond, Va.) and the temperature was kept at 150° C. for 4 hours to obtain PGS prepolymer in the form of a viscous amber color solution.

Because the PGS prepolymer was in a viscous aqueous form, it usually requires thermal curing at 120° C. for 48 hours to form the solidified PGS elastomer (Yi and LaVan 2008). In the present invention, PGS prepolymer was used in making the polymer and protein solution blends for electrospinning.

Production and Characterization of the Electrospun Mats.

Solutions for production of nanofiber mats were prepared using type I collagen (Collagen type I from calf skin was purchased commercially (Elastin Products Corp, MO)), silk fibroin, and PGS, synthesized as described above, at different weight ratios of 9:0:1, 8:1:1, 4.5:4.5:1, 1:1:8, and 0:9:1, which were dissolved in HFP respectively. The syringe loaded with the solution was fixed on a Baxter infusion pump (Model AS50) to eject the polymer solution at a rate of 3 ml/hour. A 35 kilovolt high voltage (Gamma High Voltage Research, Ormond Beach, Fla.) was applied, and a distance of 20 cm was provided between the metal collector plate (12 cm by 12 cm) and syringe tip. The electrospun mats were then placed in a 120° C. oven for 48 hours to thermally crosslink PGS (Yi and LaVan 2008). Proteins were chemically crosslinked with glutaraldehyde vapor for 24 hours (Sung et al. 2000).

Morphology of Electrospun Mats.

Images of the electrospun mats were obtained using scanning electron microscopy (JEOL JSM-6330F) and used to measure fiber diameters. Using NIH Image J software, sixteen random measurements of fiber diameters from each mat were obtained.

Characterization of Chemical Functional Groups and Physical Properties of Electrospun Mat.

Chemical functional groups were detected using a Perkin-Elmer FT-IR spectrophotometer to identify the polymer and protein structures. The thermal transition temperatures were detected following differential scanning calorimetry (DSC) (TA instruments, New Castle, Del.). Thermal transition curves of electrospun mats at various composite ratios were obtained from −60° C. to 300° C. at an increment rate of 20° C./min. All mats were randomly sampled in triplicate.

Thermal Transition Analysis.

The transition in physical state due to temperature change is important to implantable grafts. It is necessary to obtain a comprehensive thermal transition profile of electrospun mats with temperatures ranging from below storage temperature to above autoclave temperature. Phase changes of the materials are associated with exothermic (release heat) and endothermic (absorb heat) reactions. These thermodynamic changes can be detected by differential scanning calorimetry (DSC). Samples were prepared using a 3 mm biopsy punch and placed inside of standard Tzero aluminum pan/lid pairs (TA instruments, New Castle, Del.). An empty pan of the same materials was used as a reference. In each group, three samples were prepared and tested. The aluminum pan/lid pairs were weighed before and after loading the samples to calculate the sample weight. Thermal stabilization with no endo/exothermic events was achieved before the sample reached −60° C. (Simone, Dziubla et al. 2009). To obtain the complete profile of thermal transitions of the various composite ratios of electrospun mats, the DSC was run with the following steps: (1) Equilibrate to −70° C. Ramp 20° C./min to 300° C. (heat); (2) Mark end of cycle 0; (3) Ramp 20° C./min to −70° C. (cool); (4) Mark end of cycle 1; (5) Ramp 20° C./min to 20° C. (heat); (6) Mark end of cycle 2.

The obtained thermal transitions depicted by heat flow over temperature were individually plotted and analyzed. By analyzing the thermal transition curves measured by DSC, changes in protein conformations and assemblies of the peptide chains can be studied. The glass transition may be seen as a step endotherm illustrating the state transition of the material from crystalline to amorphous phase. The melting point seen at the peak of a large endotherm depicted the material transition from solid to fluidic state of the material.

For collagen, temperature induced denaturation disrupts the hydrogen bonding between the polypeptide chains, and disassembles the helical structures to form a random coil. For highly crystalline fibroin, the temperature induced phase transformation is important to understand the protein conformation. These changes can be reflected by endotherms in the thermal transition curve.

Porosity Measurements.

Following hydration in 5 ml DDH$_2$O on a mechanical shaker for 30 min at 22° C., mat samples were blotted dry and the weights were measured again (Kim et al. 2003). The density of type I collagen (1.40 g/cm$^3$), silk fibroin (1.31 g/cm$^3$), and PGS (1.13 g/cm$^3$) and the weight ratios were used to calculate the densities of the composites (Pomerantseva 2009; De Cupere et al. 2003; Minoura et al. 1990). The volume of each electrospun mat sample was obtained by dividing the weight by the density of the mat, and then the porosity was calculated using the following equation $$\varepsilon = \frac{V_{liq}}{V_{liq} + V_{MAT}}.$$

Where $V_{liq}$ is the volume of the intruded water and $V_{MAT}$ is the volume of the electrospun mat (Kim et al. 2003).

Mechanical Tensile Testing.

The standard dumbell stamp (ASTM D638-IV cutting die, Pioneer-Dietecs Corporation, Norwood, Mass.) was used to prepare samples of each electrospun composite. An Instron 5500R mechanical tester (Instron Corporation, Norwood, Mass.) with a 500 N load cell and BlueHill software was used to perform uniaxial tensile tests of the mats after hydration in 100 ml DDH$_2$O for 10 minutes at an elongation rate of 10 mm/min Three measurements from each type of electrospun mat were used to calculate elastic modulus, stress, and strain values.

Modified Suture Retention Testing.

A suture retention test performed in the manufacture of heart valve is capable of modification from a published protocol (Trowbridge et al. 1989). Five samples of each mat measuring 2 cm in length and 0.5 cm in width were prepared. The monofilament prolene suture (3-0 monofilament; Ethicon, Somerville, N.J.) was placed 0.5 cm from the edge to form a single loop. Samples were loaded onto the BOSE-Electroforce mechanical tester, and stretched at a rate of 10 mm/min until the suture completely ripped the material.

Material Degradation.

To assess degradation, 5 random samples of PFC mats (at 4.5:4.5:1 weight ratio of collagen:fibroin:PGS) were incubated at 37° C. in 10 ml phosphate buffered saline (PBS) containing 0.1% sodium azide. Samples from 3 batches were tested in separate experiments. The weights of samples were measured every week over a 30 week period. The percentages of weight loss was calculated as the ratio of mass change after degradation to the original mass of the scaffold according to the formula Weight loss (%)=W1/Wi×100%. (Wi:=initial weight of the electrospun fiber mats and W1=weight loss of the same fiber mats after exposure in degradation solution). At each time point, one sample was lyophilized and processed for SEM and used to evaluate fiber morphology.

Cell Adhesion and Proliferation.

Heart valve grafts are directly in contact with blood. Whole blood is composed of red blood cells, white blood cells, platelets, and plasma proteins. In the body, platelets adhere to sites of vascular lesions and participate in one of the initial events of thrombosis (blood clot). A monolayer of endothelial cells which lines both surfaces of valvular tissue provides further mechanical strength to valvular ECM and a protective layer to prevent thrombosis. The endothelial cells prevent platelets from coming into contact with subendothelial collagen which leads to platelet activation and thrombosis (Zhu, Negri et al. 2010). Therefore, a graft material that promotes the formation of an endothelial cell monolayer on the graft in a continuous manner is important for ensuring the functionality and hemocompatibility of the implant.

Hemocompatibility.

The interaction of platelets with the electrospun mats of the present invention were observed. This is because platelet activation plays an important role in thrombosis which will directly affect the hemocompatibility and success of a heart valve graft. An amino acid sequence -Arg-Gly-Asp (RGD) on proteins such as collagen can activate platelet aggregation by inducing high binding affinity of the platelets. The mechanism proceeds through binding of the glycoprotein GPIb and GPIIb/IIIa receptor on the platelet surface to the proteolytic factor von Willebrand factor, which recognizes and binds to the binding domains in thrombogenic materials, such as collagen. Such signalling will changes the conformation of integrin on the platelet surface and leads to thrombus formation (Zhu, Negri et al. 2010; Mendelboum Raviv, Szekeres-Csiki et al. 2011). To test the hemocompatibility of graft materials embodying the invention, platelet activation was studied by the number of adhered platelets and their morphologies on various substrates.

Cell Culture Study.

To test cell-material interaction, PFC mats were sterilized with ethanol followed by ultra-violet (UV) exposure to each side for 1 hour. In order to mimic in the in vivo condition where plasma proteins coated implanted material, fibronectin (Sigma, St Louis, Mo.) was used at a concentration of 100 μg/ml to coat mats and culture dishes. HUVECs (ATCC: CRL-1730) were seeded on the substrates in a 16 well culture plate at a cell density of 50,000 cells/well. On day 3 and day 7, rhodamine-phalloidin and sytox green dyes (Invitrogen, Eugene, Oreg.) were used, respectively, to visualize F-actin and nuclei using a Zeiss confocal microscope. Image J software (NIH) was used to count the cell numbers from representative confocal imaging micrographs.

Platelet-Material Interaction.

Human whole blood was drawn into a 2.7 ml BD Vancutainer® Coagulation Tube (BD, Franklin Lakes, N.J.) and centrifuged at 800 rpm for 15 min at 25° C. with Harrier 18/80 centrifuge (Sanyo Gallenkamp, Loughborough, UK) to obtain Platelet rich plasma (PRP). In a first experiment, PFC mats, type I collagen mats or hydrogels of rat tail type I collagen (BD Biosciences, Bedford, Mass.) hydrogels were placed in culture dishes and used as substrates for platelet adhesion. PRP is diluted with PBS to $2.16 \times 10^8$ platelets/ml, and 100 μl was applied to the center of the substrates. After 15 minutes materials are washed two times with PBS followed by fixation in 2.5% glutaraldehyde. F-actin, the contractile protein expressed in platelets, was stained with rhodamine-phalloidin to identify platelet interactions with materials. The amount of adherent platelets on various substrates was observed using confocal microscopy and the morphology of platelets were observed using SEM. Platelet adhesion was quantified using a cell counter and Image J software. In a second experiment, HUVECs were cultured on different materials for 24 hours prior to the addition of platelets. The same protocol was used for platelet addition and evaluation of platelet adhesion. Three pictures were taken from randomly selected different areas on the substrates. The numbers of platelets were counted and compared among groups.

Statistical Analysis.

Data is presented as mean±standard error of the mean (SEM) unless otherwise noted. Statistical significance was determined using one-way analysis of variance (ANOVA) following post hoc test for multiple groups when appropriate. A value of $p<0.05$ was considered statistically significant. StatView 5.0 (SAS Institute, Cary, N.C.) was used to perform the statistical analyses.

Mechanical and physical tests on the PFC mats embodying the present invention demonstrate that the material has superior strength and flexibility compared to primarily collagen rich biomaterials. The β sheet structure of fibroin normally results in a stiff but brittle material. However, blending silk fibroin with collagen and PGS created a novel and surprisingly tough material with elastic properties. A composition of 90% fibrous protein and 10% elastic protein was initially considered optimum based on the composition of native heart valve. While 10% PGS was thought to be sufficient to substitute for elastin based on natural valve composition, collagen and fibroin optimization was necessary. Results showed electrospun mats at 4.5:4.5:1 weight ratio of collagen, fibroin, and PGS was optimum based on comparisons made with native heart valve. In the suture retention tests, PFC mats showed satisfactory suture retention force as compared to fresh porcine heart valve, indicating that PFC mats could be used effectively as surgical implants.

Creating valvular grafts capable of retaining mechanical integrity by resisting cell-mediated mechanical buckling and microstructure failure is a major challenge (Cebotari 2011; Dijkman et al. 2012). One approach involves having cells seeded first on synthetic grafts in order to deposit ECM composites. Prior to the use of these ECM "conditioned" grafts, cells were removed to prevent further contraction (Dijkman et al. 2012). The present invention utilized a different strategy, which is fundamentally to improve the strength of the graft material by appropriate selection of components so as to prevent cell-mediated buckling. This was accomplished by incorporating silk fibroin with helical collagen and the elastomer PGS to obtain both strength and flexibility (Beun et al. 2011; Billiar et al. 2000). The brittleness of silk fibroin was modified by incorporating collagen and the elastic PGS. An interconnected, porous meshwork was fabricated using electrospinning. Silk fibroin protein has unique anti-parallel β sheet structure making the composite stiff (Jiang et al. 2007). The FTIR suggested amides slightly shifted from higher wavenumbers to lower wavenumbers as the collagen content decreased and fibroin content increased in the composites. These shifts corresponded to changes in a random coil structure that was present in collagen and the β sheet structure that was characteristic for fibroin as the composite ratio changed (Hu et al. 2006; Zoccola et al. 2008).

PFC mats showed minimal weight loss during a 30 week degradation study and the ultrastructure of the nanofibers showed little if any changes. Notably, the structural integrity was superior to the reported degradation of fully crosslinked collagen or polylactic acid electrospun constructs (Horan et al. 2005; Zong et al. 2003; Liu et al. 2010; Kim et al. 2003). The results of the studies on PFC mats indicate that silk fibroin degrades slower than most of other collagen-containing scaffolds, such as poly caprolactone-collagen scaffolds which completely degraded in 4 weeks (Zhou et al. 2010; Tedder 2009). These studies suggest that PFC mats should be stable at 37° C. following implantation in patients. Indeed, the PFC mats demonstrated an unexpectedly slower rate of degradation as compared to collagen alone.

Cell attachment and growth is considered to be the first step for achieving sufficient tissue remodelling and maturation of implanted heart valves in vivo (Butcher et al. 2011). In the present invention HUVEC cells attached and proliferated on PFC mats and produced a monolayer with tight junctions. A high level of cell adhesion and the potential for tight cell-cell interactions translates into improved mechanical strength of the graft material (Edwards et al. 2005).

While not wishing to be restricted to any specific theory of operation, it is believed that 1) individual collagen, fibroin, and PGS components in the fibrous mats provide binding sites and microenvironment cues for guiding cell adhesion and proliferation (Gu et al. 2010; Shekaran and Garcia 2011; Zou et al. 2012); and 2) in contrast to other materials, the PFC mats of the present invention are effective in producing a better quality glycocalyx.

The special structural features of PFC mats could potentially contribute to long term viability of valvular cells. The interconnected nanofiber network had a thickness of 100-300 μm and could efficiently support nutrient, oxygen transport and soluble cell signal transmission. The electrospun fibers of PFC mats mimicked the highly porous matrix structure of valvular ECM which is essential in providing a large surface area for cell attachment and growth.

To improve the functionality of PFC mats, electronegative carbohydrates such as glycosaminoglycans, growth factors or specific cell signalling molecules can be further incorporated to provide mechanical and chemical cues to cells in biomaterials (Jordan et al. 2012; DeCock 2010; Yamada et al. 1980; Deng 2011). These further functionalized materials may contribute to a higher level of mature valvular tissue formation by attracting and integrating larger amount and more viable native valvular or progenitor cells.

Published studies have shown elevated thrombogenic risks associated with decellularized collagen-based grafts (Schopka 2009). The present invention demonstrates that the PFC mats are more hemocompatible than structurally similar collagen materials of the prior art. Because the PFC mats are directly synthesized and fabricated from proteins and synthetic polymer, they offer an unlimited off-the-shelf alternative supply, and minimal concerns with respect to disease transmission risk, as compared to processed bovine or porcine grafts. The electrospinning fabrication techniques can be used to rapidly produce PFC mats compared to other heart valve graft processing procedures (Sacks et al. 2009). As a feasible fabrication technique, electrospinning on molds could be used to recreate the native geometry of certain tissues, such as heart valve tissue. Other uses might include fabrication onto stents for use as a new generation of transcatheter heart valve for use in minimally invasive cardiothoracic surgery (Dijkman et al. 2012).

The present invention demonstrates the formulation of a new composite of natural and synthetic material that can be used for tissue replacement, particularly heart valve replacement. In the present invention, composites of collagen, fibroin and PGS were successfully created and fabricated using electrospinning. These compositions provide the unique property of viscoelasticity combined with tensile strength. Accordingly, the compositions of the present invention are useful in a variety of wound care dressings and skin covers, in addition to their use as graft materials for tissue replacement.

The preferred electrospun material is a PFC mat with collagen:fibroin:PGS at 4.5:4.5:1 weight ratio. The compositional and structural similarities of PFC mats to native valvular tissues potentially offer cellular binding sites and microenvironment cues for cell adhesion and growth. The interconnected fibrous structure and high porosity of PFC mats provides a large surface area and internal space for tissue maturation to occur. Mechanical testing demonstrated the PFC mats had comparable mechanical strength to fresh heart valve tissue, and therefore could withstand physiological blood pressures. Functionality tests showed minimal weight loss and sustained nanofiber structural integrity over a 9-week study of degradation. Organized endothelial monolayers with tight cell-cell functions formed on PFC mats. Reduced platelet adhesion and aggregate size suggests PFC mats are less thrombogenic compared to collagen nanofiber mats and collagen gels.

In summary, the novel PFC mats created in the present invention may be used as durable, biocompatible, and non-thrombogenic grafts. The fabrication process can be further implemented to mimic the geometry of native heart valve in order to enhance the in vivo functionality and performance of the PFC mats.

The following examples describe the invention in further detail. These examples are provided for illustrative purposes only, and should in no way be considered as limiting the invention.

Example 1

Composite Characterization

The blending of materials in composite nanofibers is initially demonstrated. For the extracted fibroin, FTIR spectroscopy indicated amide I, II, III groups were in the β sheet conformation based on wavenumbers corresponding to the carbonyl stretchs 1619-1622 $cm^{-1}$, 1509-1516 $cm^{-1}$, and 1225-1233 $cm^{-1}$ respectively [23-24]. The wavenumber ranging from 3275-3282 $cm^{-1}$ was indicative of the —N—H stretching vibration shown as a broad peak for amide A. An absorption peak of 1700 $cm^{-1}$ was assigned to be the C=O stretch in amide I β sheets, and 1225-1233 $cm^{-1}$ referred to the C—N stretch and C—N—H bend in amide III β sheets structure (Hu et al. 2006; Hayashi et al. 2007). Two strong peaks were shown at the regions of 1619-1622 $cm^{-1}$ for C=O stretch of amide I and 1509-1516 $cm^{-1}$ for the C—N stretch and C—N—H bend for amide II (Horan et al. 2005). (FIG. 1). Type I collagen had a characteristic broad peak at the absorption of 3275 $cm^{-1}$ which was indicative for the —O—H stretch and N—H stretch in this region (FIG. 1—region 1). PGS polymer had a distinct FTIR spectrum which showed a broad —OH stretch at 3458 $cm^{-1}$. This characteristic was reported to indicate the hydrogen bonded hydroxyl groups in PGS (Wang et al. 2002). Sharp transmittance peaks at 2928 $cm^{-1}$ and 2855 cm-1 (FIG. 1—region 2) were shown to represent the sp3 C—H stretch (asymmetry and symmetry). Moreover, the intense ester C=O stretch at the absorption of 1734 $cm^{-1}$ (FIG. 1—region 3) was another unique feature for PGS which was not presented in either collagen or fibroin. Amide III was at the absorption range of 1228-1237 $cm^{-1}$ (FIG. 1—region 6). Amide I, II were present at the absorption range of 1622-1630 $cm^{-1}$ (FIG. 1—region 4) and 1546-1515 $cm^{-1}$ (FIG. 1—region 5) respectively. In summary, all composites were demonstrated to be blends of strategy materials based on identification of expected absorption wavenumbers (FIG. 1).

Example 2

Fiber Morphology

Figure 2:
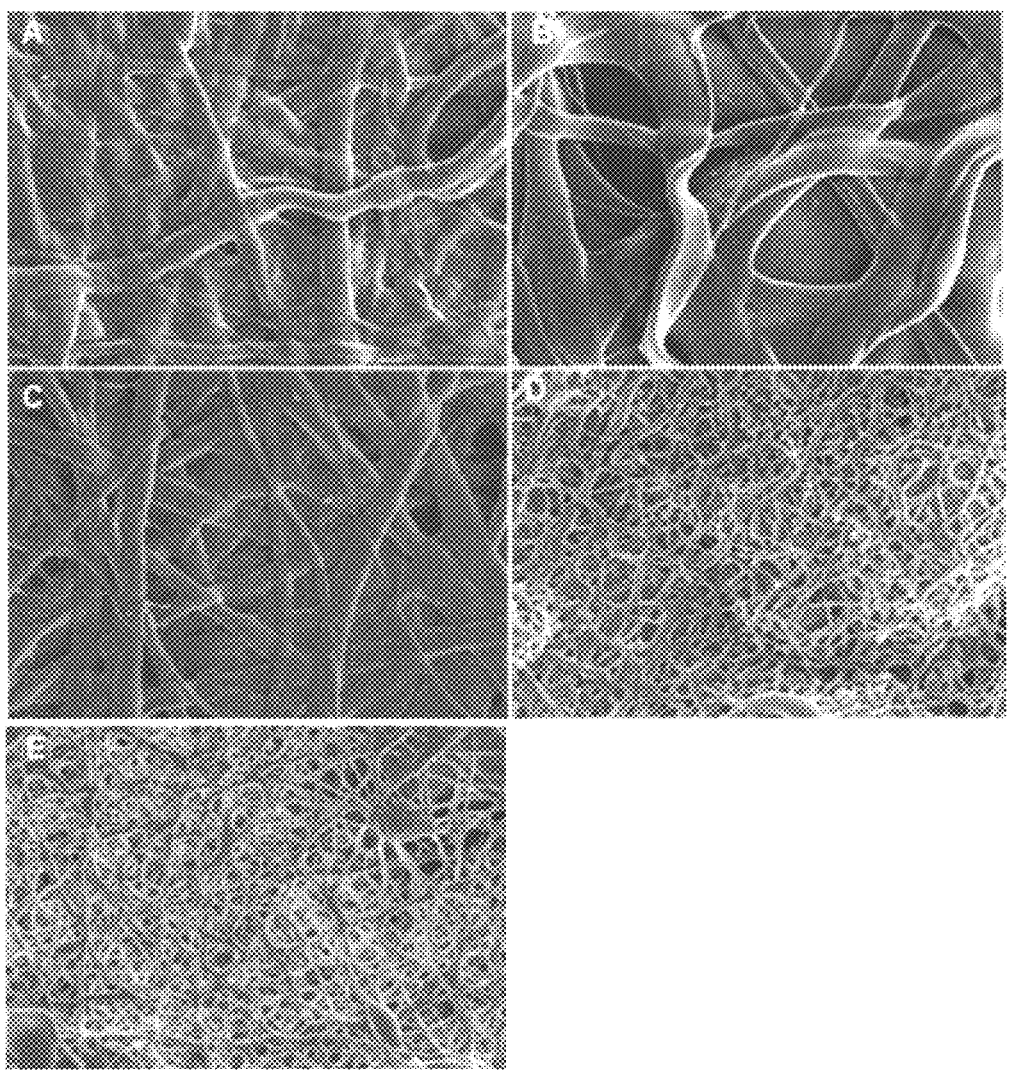
FIG. 2 depicts scanning electron microscopic images illustrating the morphologies of certain electrospun fibers. The diameters of the random arrays of electrospun cross-linked fibers after crosslinking, and treatment with glycine and water are shown. (A) Collagen: PGS (9:1); (B) collagen:fibroin:PGS (8:1:1); (C) collagen:fibroin:PGS (4.5:4.5:1); (D) collagen:fibroin:PGS (1:8:1); (E) fibroin: PGS (9:1). With higher silk fibroin protein content, smaller fiber diameters were observed (Magnification 2300×).

Fiber diameters ranged from 694 to 4577 nm (Table 1). In general, thinner and more rounded fibers were observed for the electrospun mats with higher fibroin content (90% and 80%) as compared to the thicker and more flat fiber of electrospun mats with high proportions of collagen (90%, 80%, and 45%). The interconnected fiber network structures of electrospun mats at various collagen, fibroin and PGS weight ratios were compared after crosslinking using scanning electron microscopy (SEM) (FIG. 2).

TABLE 1

Fiber Diameters in Mats of Different Compositions

| Sample Type | Fiber Diameters (nm) |
| --- | --- |
| Collagen:PGS (9:1) | 2067 ± 168 |
| Collagen:Fibroin:PGS (8:1:1) | 4577 ± 697 |
| Collagen:Fibroin:PGS (4.5:4.5:1) | 2952 ± 240 |
| Collagen:Fibroin:PGS (1:8:1) | 784 ± 77 |
| Fibroin:PGS (9:1) | 694 ± 43 |

All values represent means ± SEM;
The fiber diameters were measured from 16 randomly selected fibers of two representative SEM pictures. The measurements are presented as mean ± standard error of the mean.

Example 3

Thermal Transition Analysis of Electrospun Mats

Figure 3:
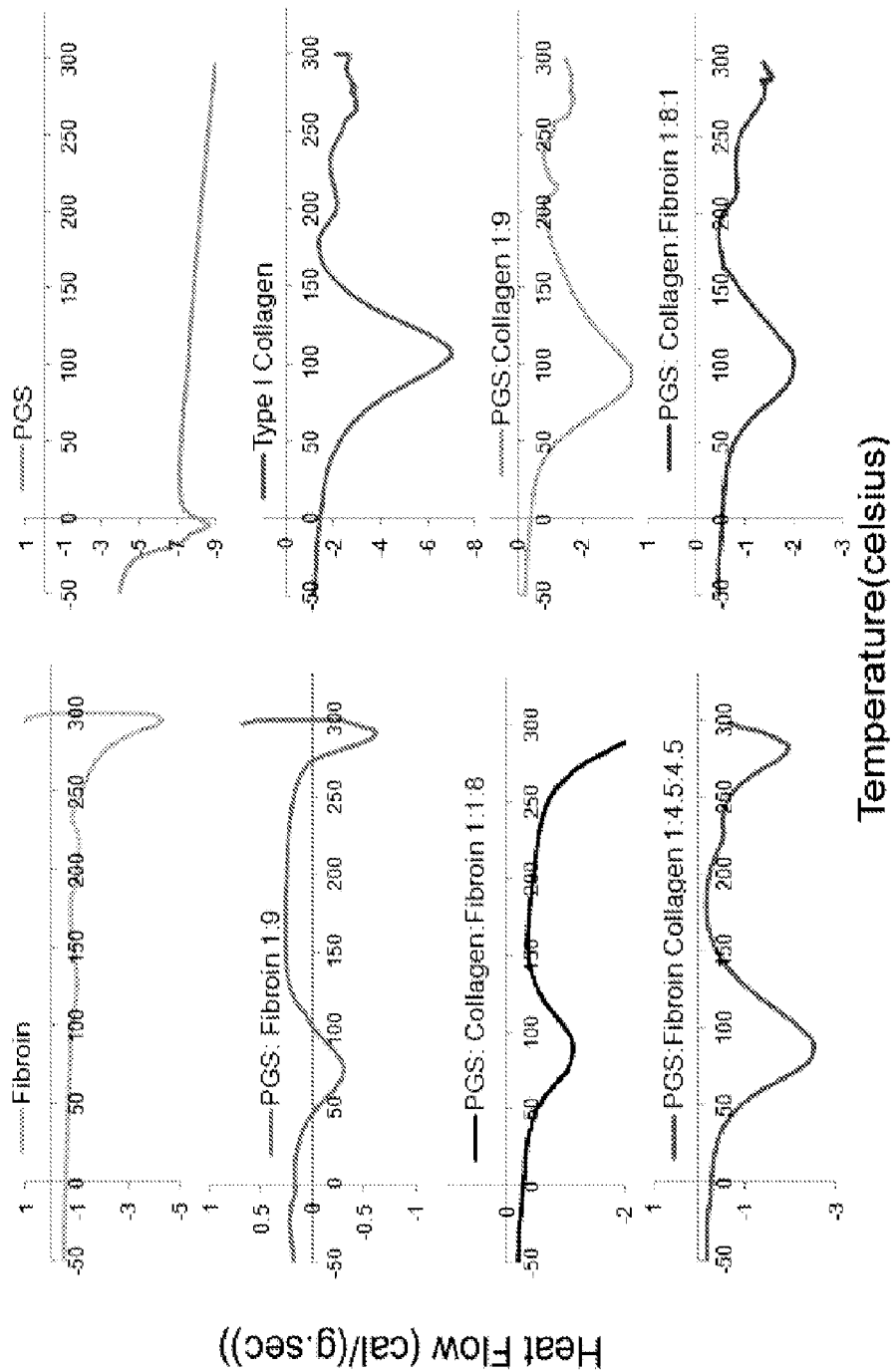
FIG. 3 depicts differential scanning calorimetry (DSC) scans of electrospun mats prepared from collagen, PGS, fibroin and composites thereof.

Results of DSC scan were analyzed to determine thermal transition temperatures of electrospun mats (FIG. 3). By incorporating an increasing amount of fibroin, a shift of thermal transition temperature to higher range was observed.

The electrospun composite materials exhibit much higher thermal transition temperatures as compared to PGS alone. Results suggest the electrospun mats made from collagen, silk fibroin, and PGS composites were thermally stable for in vivo application.

Example 4

Porosity Measurements

Porosity of the electrospun mats is important for nutrient and oxygen transport as well as cell adhesion and proliferation. Triplicate samples of all mats were weighted to determine dry weight. The porosity of the electrospun mats ranged from 67% to 80% (n=3) which is a sufficiently large surface and internal area for cell adhesion, migration and nutrients transport.

Example 5

Mechanical Tensile Testing

An essential feature of heart valve materials is the tensile and elastic properties. The elastic moduli of the electrospun mats (Table 2) ranged from 2.25 Mpa (Collagen: PGS=9:1) to 4.97 Mpa (Fibroin: PGS=9:1). The highest elastic modulus was observed for composites containing 45 or 80% fibroin. Electrospun mats with collagen alone had a similar elastic modulus of 3.67 Mpa compared to collagen-based porcine valvular grafts: (3.68 MPa fresh valves and 3.95 MPa) glutaraldehyde fixed valves (Vesely et al. 1992). Incorporation of PGS created graft materials with customized elastic propertied with strain ranged from 30-70%. All mats produced had stress values between 0.69 Mpa and 1.45. These values were 100-fold greater than stress exerted by blood pressure under normal or hypertensive states. Therefore, the electrospun mats have sufficient mechanical properties to withstanding blood pressure effects. Among all electrospun materials, the composites at 4.5:4.5:1 of collagen, fibroin and PGS weight ratio had the best overall mechanical strength and elasticity.

retention force of fresh porcine heart valve (0.64N) as compared to other electrospun composites.

Based on the mechanical and physical properties, the electrospun mats containing collagen-fibroin-PGS (4.5:4.5:1 weight ratio) (PFC mats) were most similar to the mechanical properties of fresh aortic valve. The PFC mats were studied further to evaluate the degradation and cellular compatibility using endothelial cells and blood platelets. Thrombogenicity studies included cell growth on the material, formation of a tight monolayer, while thrombogenicity was assessed using by cell compatibility test the interaction of platelets.

Example 7

Figure 5:
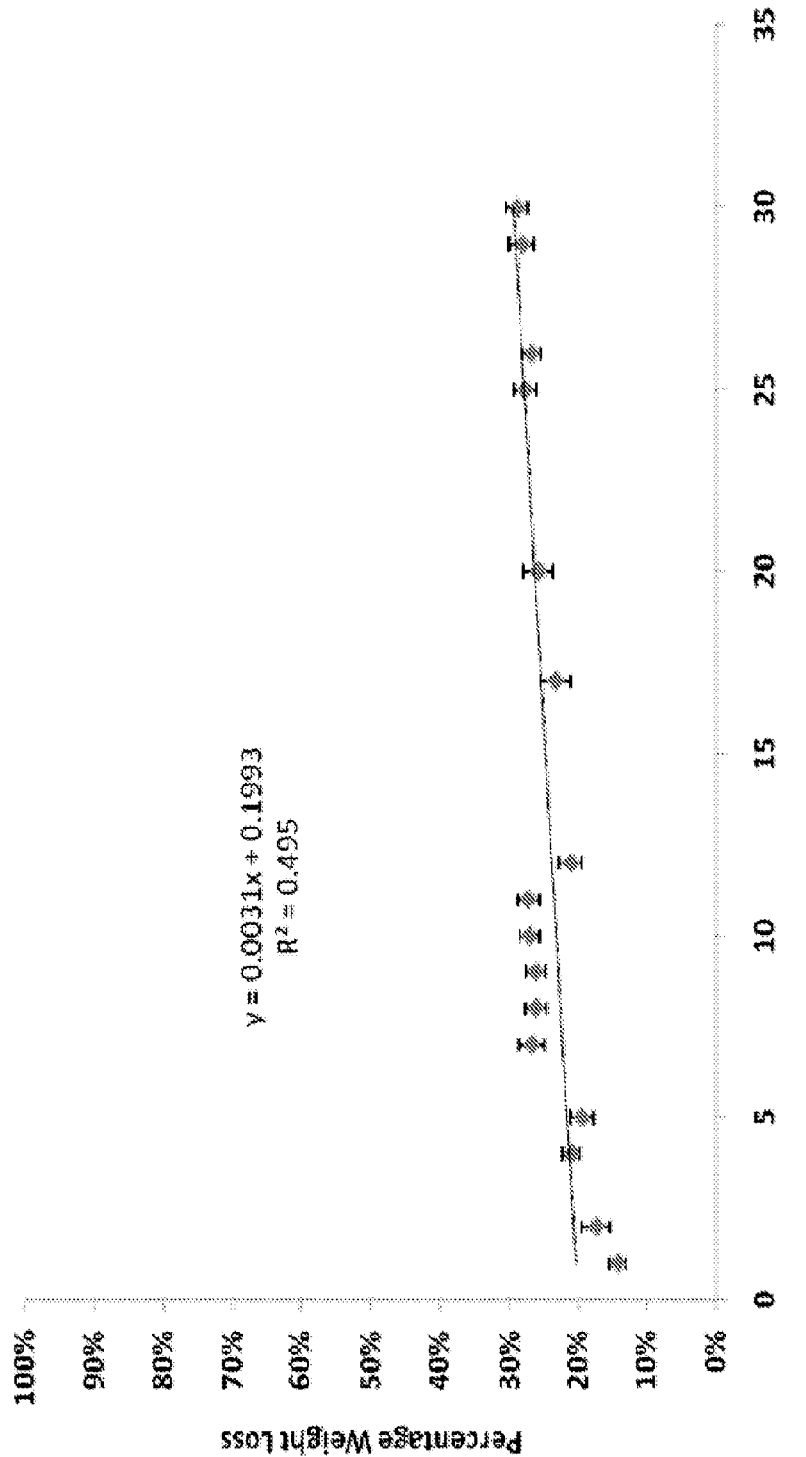
FIG. 5 illustrates degradation of a PGS-fibroin-collagen (PFC) mat during a 30 week period. Data points are presented as mean±SEM (n=4).

Degradation of PFC Mats. Degradation of PFC mats was found to be only a 0.3% weight loss per week over a 30 week incubation period (FIG. 5). With the unaided eye, PFC mats were observed to remain intact during the entire degradation time period. SEM was used to examine the fine structure of nanofibers. A consistent morphology of the fibers was observed within the fiber meshwork and was unchanged during the course of study. Fiber diameter measurements on mats indicated no significant differences over the course of the experiment.

Example 8

Cell Adhesion and Proliferation Study—Cell Compatibility Test

Figure 6:
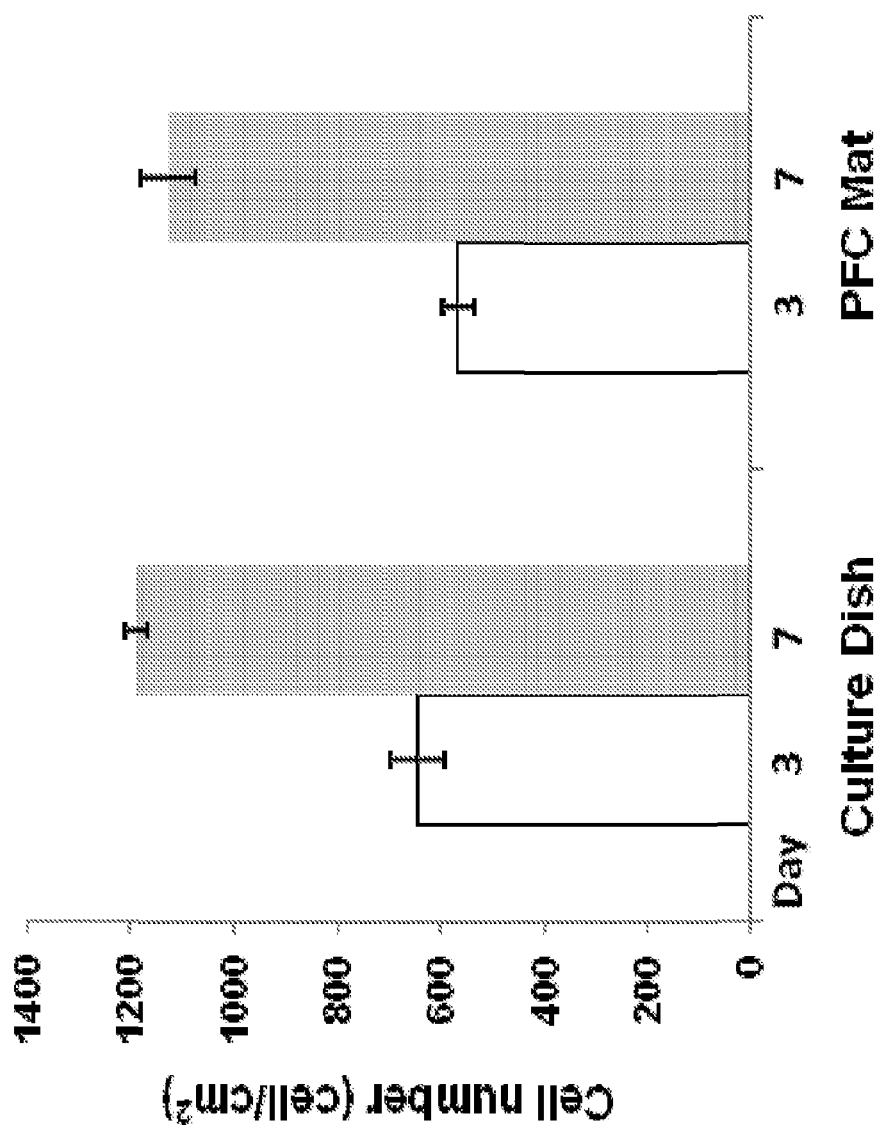
FIG. 6 illustrates cell numbers for HUVEC cultured 3 or 7 days on culture dishes and PFC mats. Bars represent the mean±SEM for each observation from representative photomicrographs (n=4). An increase number of HUVECs was observed from day 3 to day 7. For cells on both substrates, cell numbers increased significantly from day 3 to day 7 (p<0.05).

Biocompatibility and the formation of a monolayer of endothelial cells on blood contacting biomaterials is a necessary component to provide a functional and non-thrombogenics surface. When HUVEC's were cultured on PFC mats, cell numbers increased significantly (p<0.05) from day 3 to day 7 (FIG. 6) Morphologically, HUVECs on culture dishes appeared evenly spread without significant cell-cell interactions, whereas on PFC mats, an organized uniform cell sheet was formed (FIG. 7). The intense staining

TABLE 2

Uniaxial Tensile Testing of Electrospun Mats

| Sample Type | Elastic Modulus (Mpa) | Stress (Mpa) | Strain (mm/mm) |
|---|---|---|---|
| Collagen | $3.67 \pm 0.12^{a}$ | $0.69 \pm 0.06^{a, d}$ | $0.23 \pm 0.03^{a, d}$ |
| Collagen:PGS (9:1) | $2.25 \pm 0.16^{b}$ | $1.30 \pm 0.09^{b, c}$ | $0.62 \pm 0.02^{b}$ |
| Collagen:Fibroin:PGS (8:1:1) | $2.76 \pm 0.20^{b}$ | $1.10 \pm 0.09^{b}$ | $0.44 \pm 0.03^{b, c}$ |
| Collagen:Fibroin:PGS (4.5:4.5:1) | $4.11 \pm 0.13^{a, c}$ | $1.45 \pm 0.05^{c}$ | $0.41 \pm 0.01^{a, b, c}$ |
| Collagen:Fibroin:PGS (1:8:1) | N/A: too brittle to be determined | | |
| Fibroin:PGS (9:1) | $4.97 \pm 0.27^{d}$ | $0.82 \pm 0.09^{d}$ | $0.33 \pm 0.12^{a, c}$ |

All values represent means ± SEM
The tensile stress, strain and elastic modulus of electrospun mats at different composite ratios were measured. Data are presented as mean ± Standard error of the mean (n = 3). Numbers designated with the same letter are not significantly different, whereas numbers with different letters are significantly different (p < 0.05).

Example 6

Modified Suture Retention Strength Testing

Figure 4:
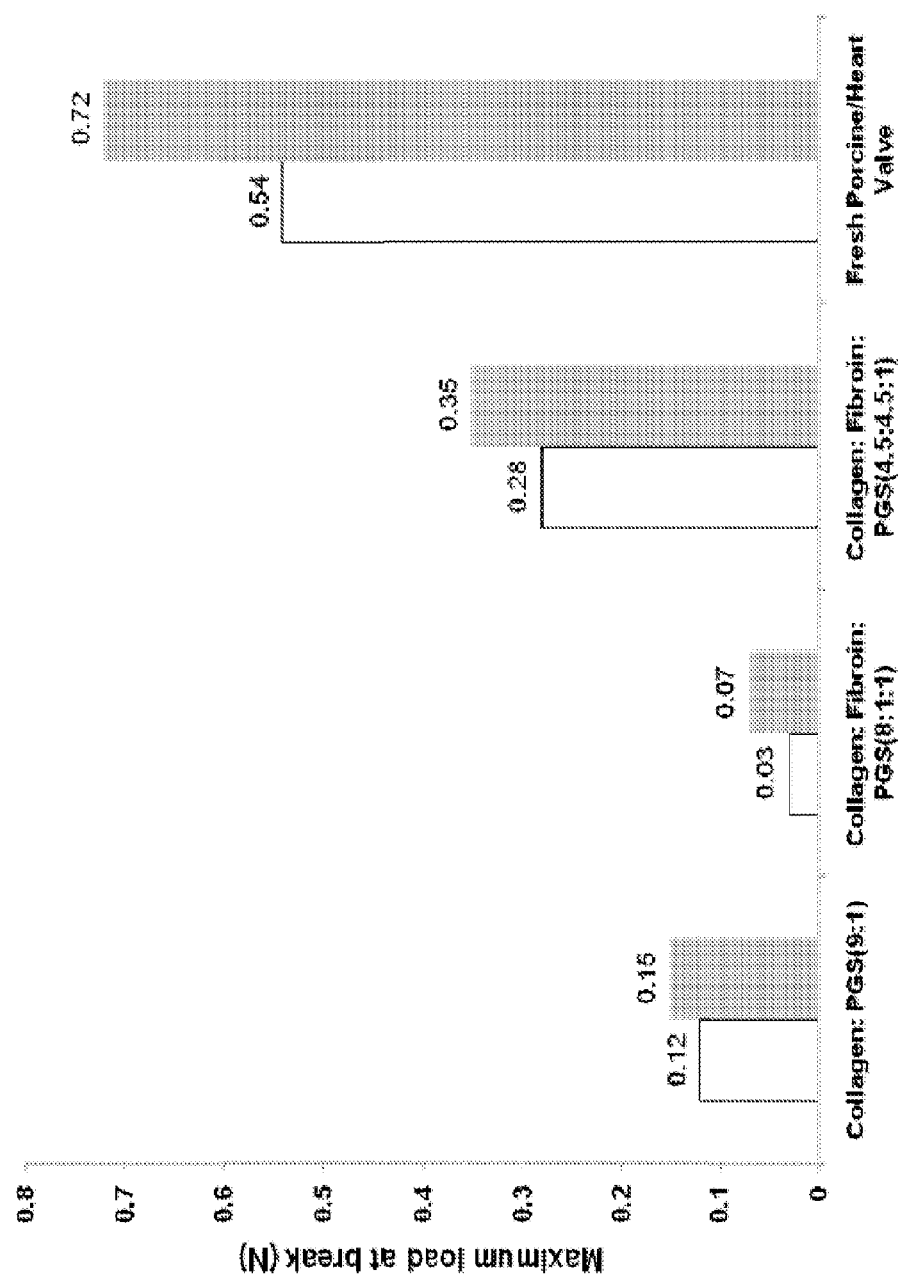
FIG. 4 illustrates the forces required to tear sutures made from electrospun mats and porcine heart valves. Duplicate samples were tested for each material. Collagen: Fibroin: PGS (4.5:4.5:1) showed the highest suture pull-out strength with a maximum average load of 0.32 N as compared to the maximum average load of 0.64 N for fresh porcine heart valve.
Figure 7A:
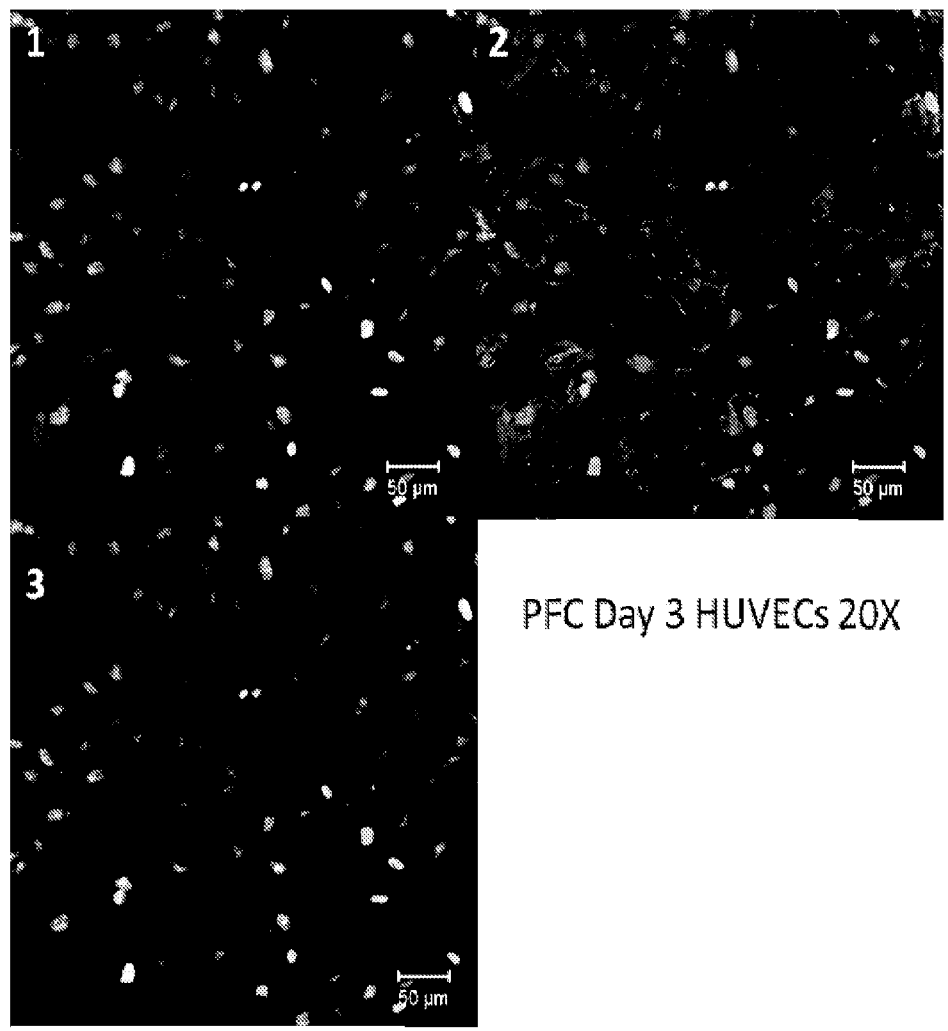
FIG. 7 displays a number of confocal microscopic images illustrating HUVEC morphology and proliferation on A: PFC mat at day 3 (images 1 and 2 represent the combined confocal image, 3 represents only the cell nuclei), B: PFC mat at day 7 (images 1 and 2 represent the combined confocal image, 3 represents only the cell nuclei), C: collagen mat at day 3 (images 1 and 2 represent the combined confocal image, 3 represent only the cell nuclei), D: collagen mat at day 7 (images 1 and 2 represents the combined confocal image, 3 represent only the cell nuclei) (cells were seeded at 50,000 per dish on a 48-well plate, representative photomicrographs depict increased cell numbers from day 3 to day 7 on both substrates, cells were stained for F-actin protein using rhodamine-phalloidin and for nuclei using sytox green (Magnification 20×; Scale bar: 50 µm)); and E: High magnification confocal image of HUVEC cultured on PFC mat for 7 days (images 1 and 2 represent the combined confocal image, 3 represents only the cell nuclei), in the magnified region the cuboidal shape of endothelial cells is illustrated (Cells were stained for F-actin protein using rhodamine-phalloidin and for nuclei using sytox green (magnification 40×; scale bar: 50 µm)).
Figure 7B:
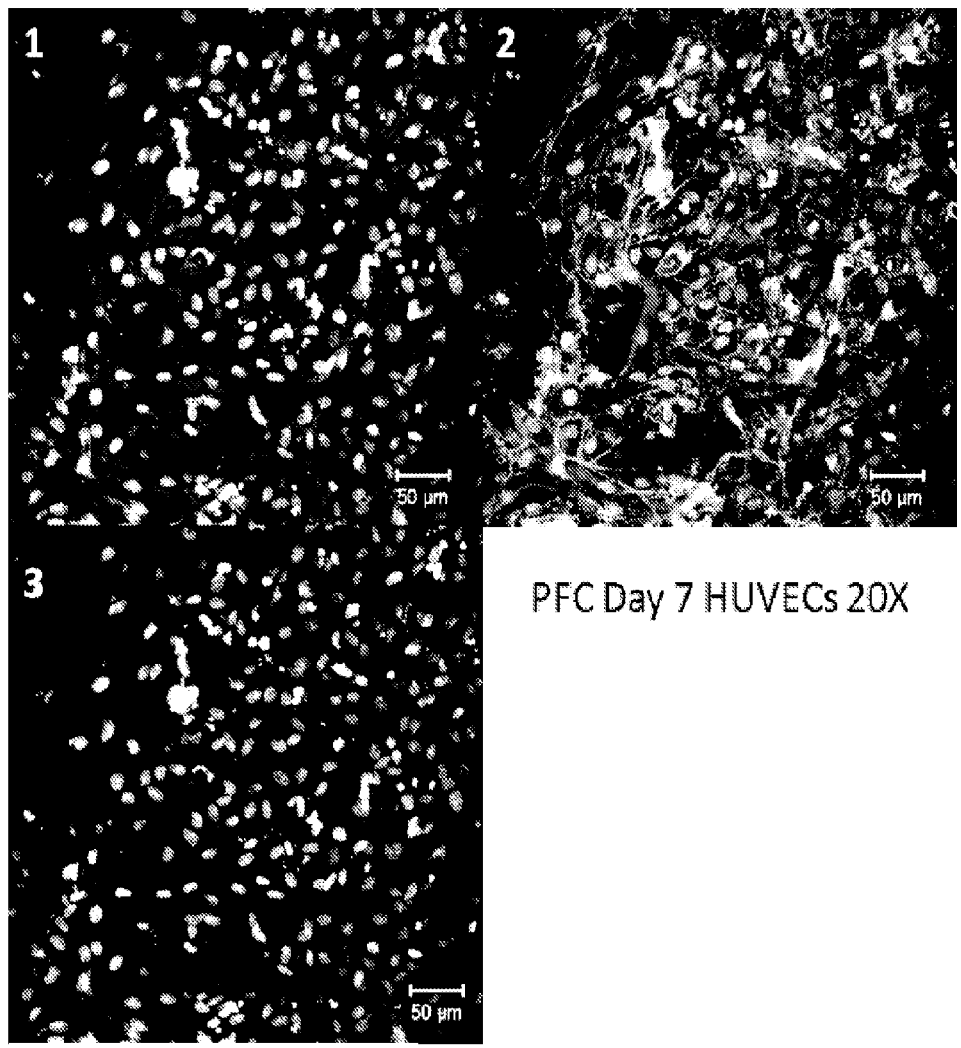

The suture retention test was used to assess the maximum force required to disrupt sutures from materials (FIG. 4). Collagen, fibroin, and PGS electrospun mats at 4.5:4.5:1 weight ratio required the greatest suture retention force with a maximum load of 0.32N, which is closest to the suture pattern of F-actin at the cell borders for cells cultured on PFC mats suggested the formation of tight junctions (FIGS. 7A and 7B).

Figure 7C:
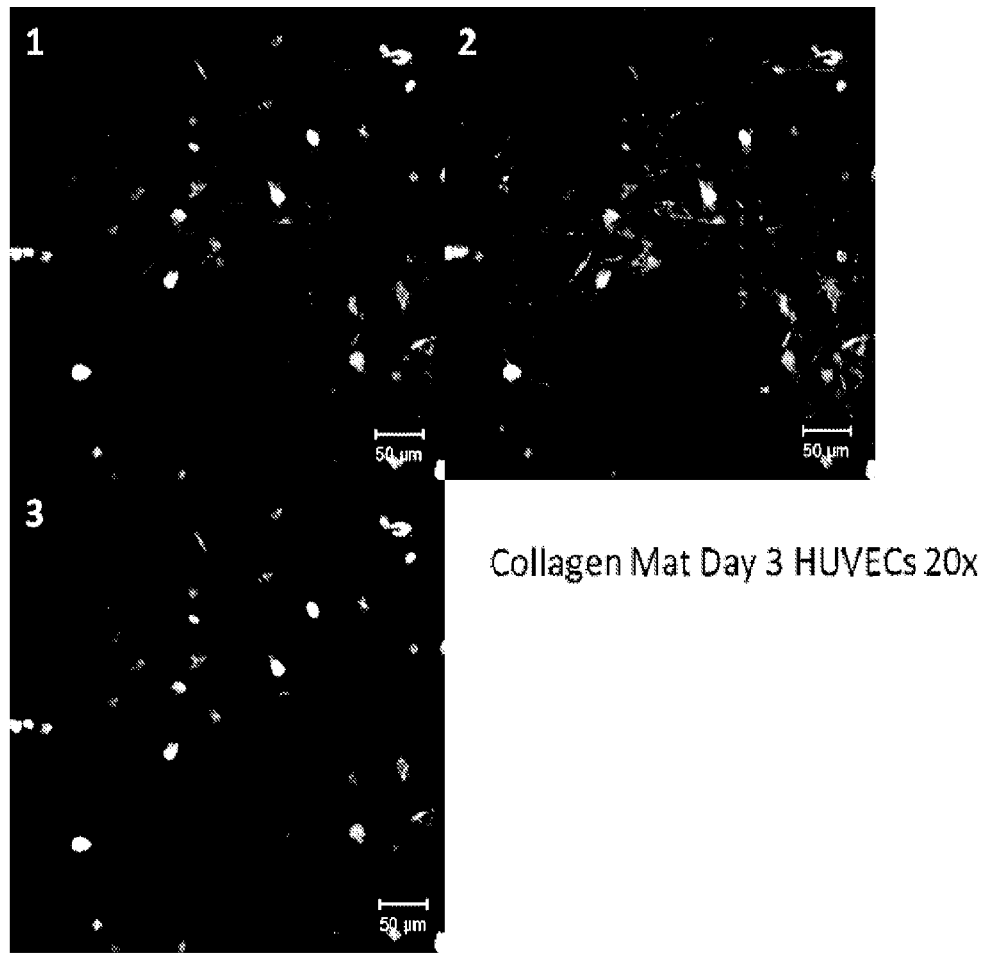
Figure 7D:
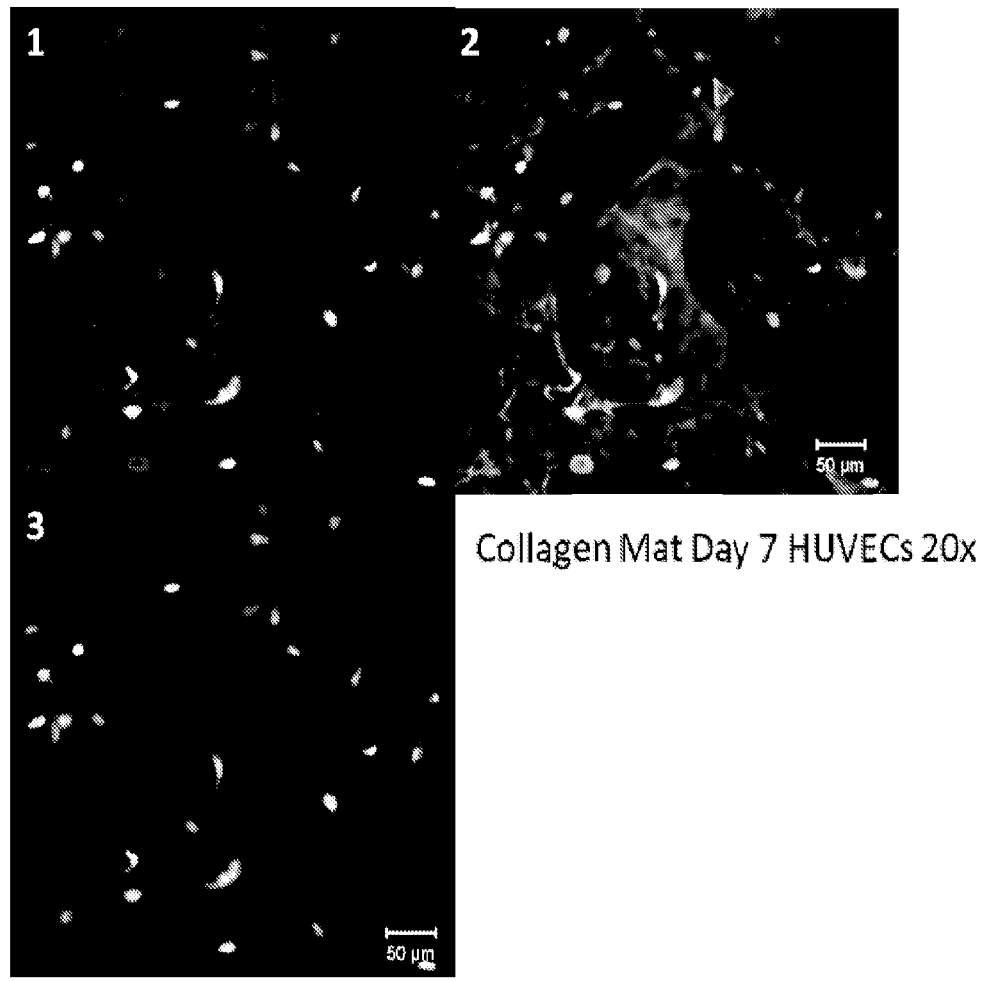

In contrast, when HUVEC's were cultured on collagen mats, seeded with the same number of cells as the PFC mats, the endothelial cells were not observed to form tight junctions (FIGS. 7C and 7D).

Figure 7E:
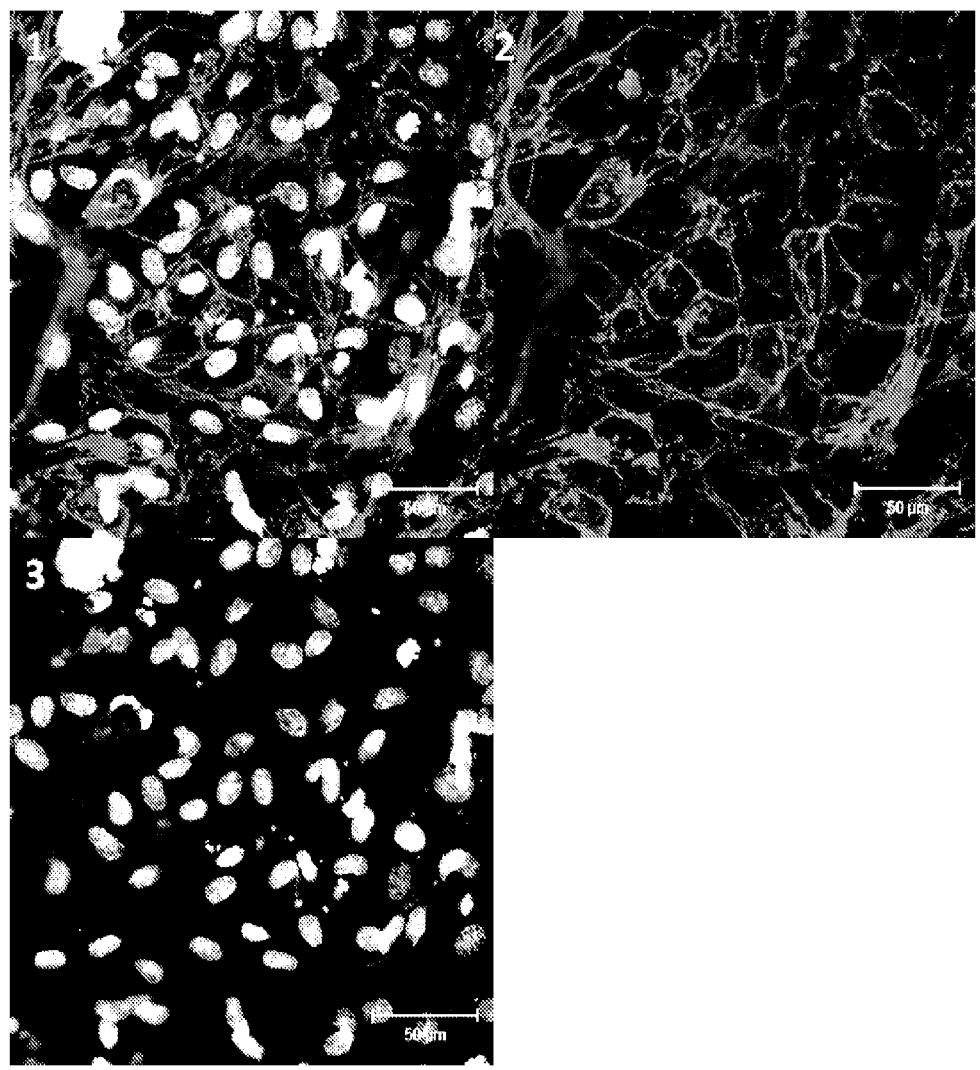

Upon examining the cells at a higher magnification, areas demonstrating tight cell-cell interactions were observed for cells cultured on PFC mats (FIG. 7E). As reported, F-actin indirectly binds to the endothelial tight junction protein such as VE-cadherin along the cell-cell junction. The intense staining pattern of F-actin at the cell borders suggests the formation of tight junctions.

Example 9

Figure 8:
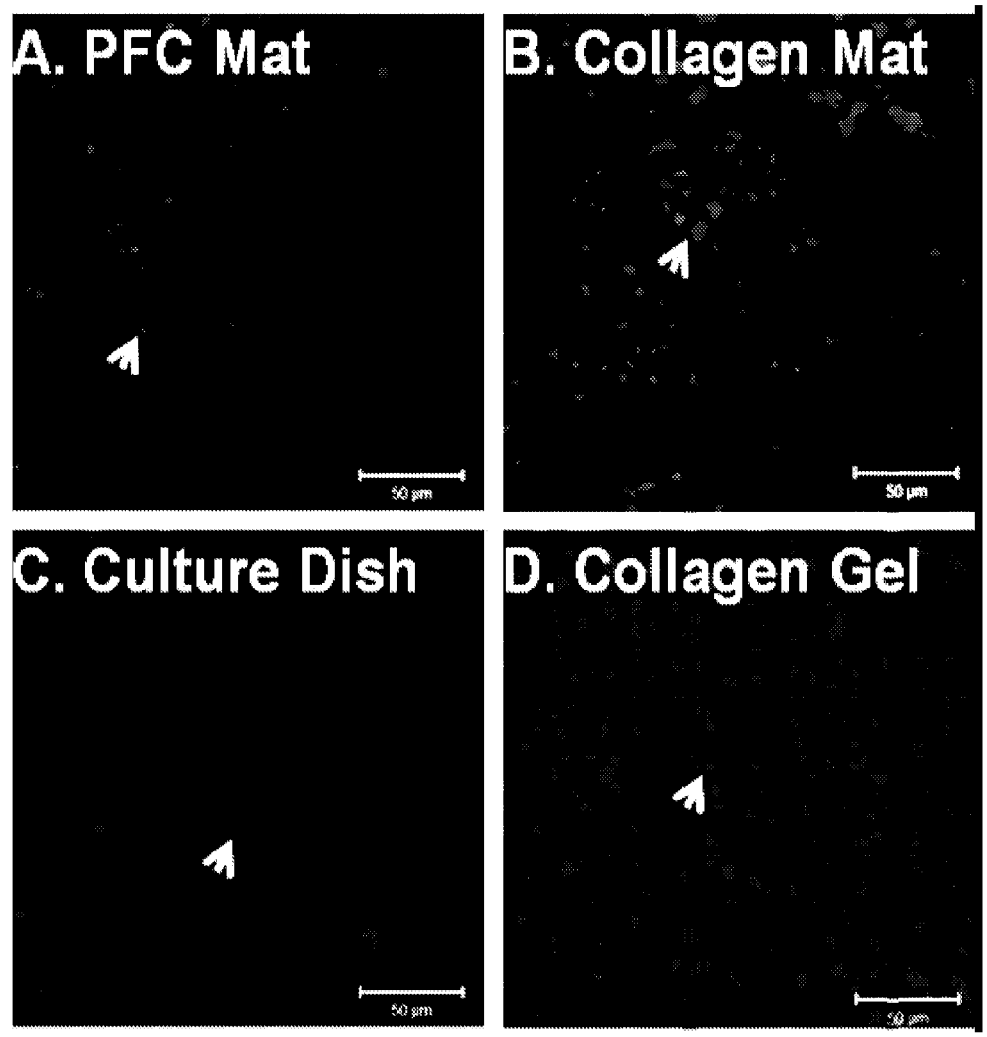
FIG. 8 displays confocal images illustrating platelet adhesion on different substrates. Platelet rich plasma (PRP) was plated with 1.08×107 platelets/dish in 48-well plate. The images were acquired after 15 min of incubation on various substrate surfaces at 37° C. A: PFC mat, B: collagen mat, C: culture dish, D: collagen gel. There are more adhered platelets and formation of microthrombi on the collagen gel and collagen mat as compared to the culture dish and the PFC mat. Platelets were visualized by rhodamine-phalloidin staining for F-actin protein (Magnification 40×; Scale bar: 50 µm).
Figure 9:
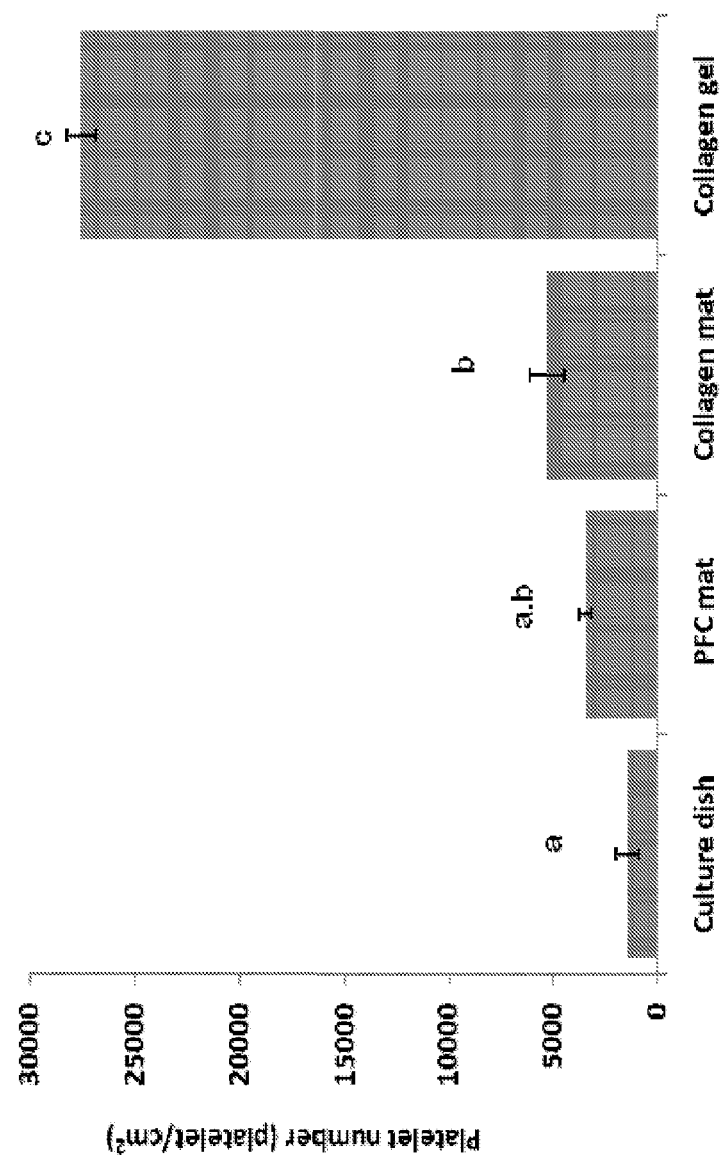
FIG. 9 illustrates numbers of adhered platelets on different substrates. Adherent platelets were counted from representative photomicrographs taken from culture dish, PFC mat, collagen mat, and collagen gel after 15 min incubation at 37° C. Data were expressed as means±SEM (n=3). Bars having a single superscript letter are not significantly different, whereas bars having two different superscript letters are significantly different (p<0.05).
Figure 10A:
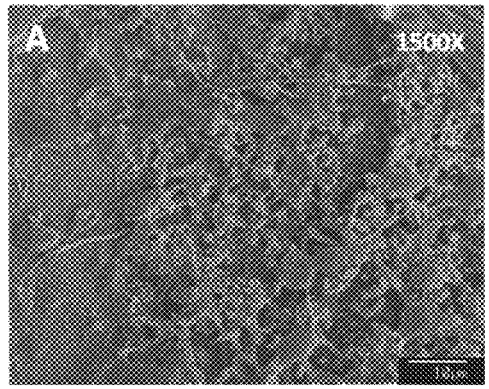
FIGS. 10A to 10F display scanning electron micrographs.
Figure 10D:
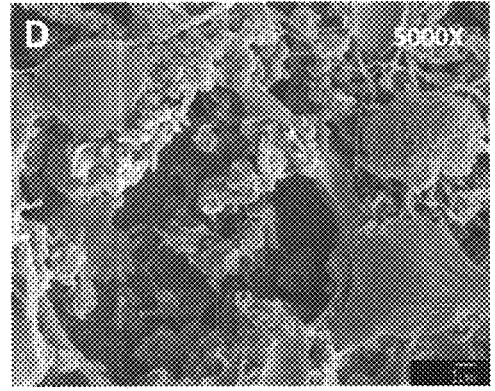
Figure 10B:
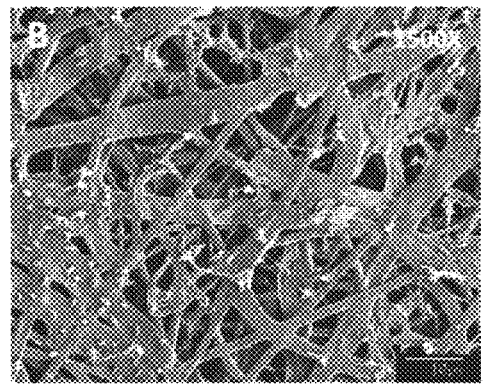
Figure 10E:
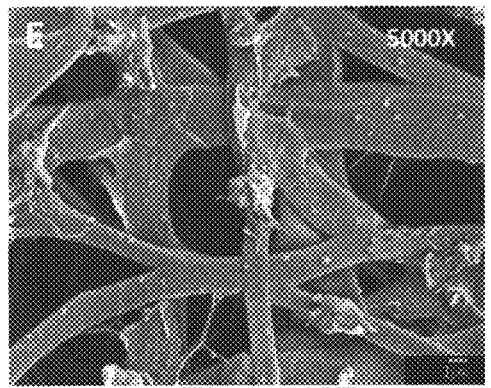
Figure 10C:
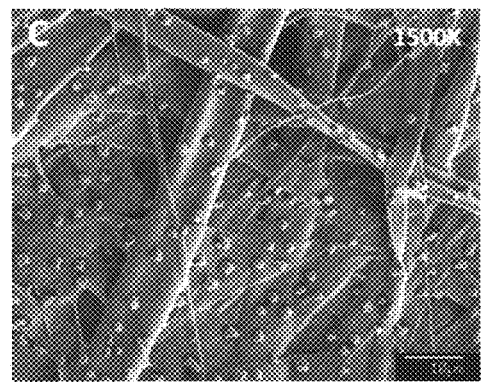
Figure 10F:
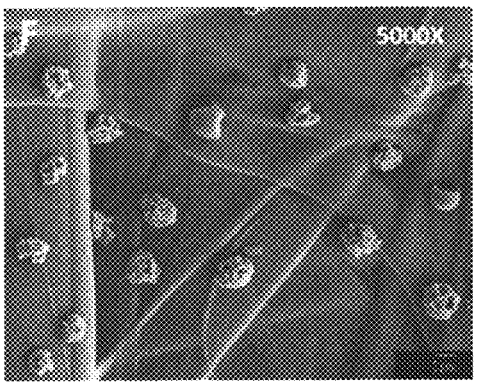

Platelet Adhesion to PFC Mats—Quantifying Adhered Platelets on Various Substrates Several studies were completed using platelets to assess the thrombogenic nature of the PFC mats alone or of mats cultured with cells. Confocal images of platelets stained with rhodamine-phalloidin demonstrated a low level of adhesion of platelet on polysterene culture dishes (FIG. 8). Single platelets or small clumps comprised of 2-3 platelets were present on PFC mats. In sharp contrast, platelets and platelet aggregates adhered extensively to the collagen gel (positive control) where images revealed increased platelets numbers as well as increased sizes of aggregates (FIG. 8). Fewer platelets and fewer platelet clumps were observed on PFC mats as compared to electrospun collagen nanofiber mats as compared to collagen controls. The numbers of adherent platelets on various substrates were determined by using cell counter in Image J software (FIG. 9). Platelet numbers on collagen mat, and collagen gel were respectively 1.5 and 7.9 fold higher (p<0.05) than on the PFC mats.

Example 10

Platelet Adhesion to PFC Mats—Morphological Identification of Platelets Activation Platelet morphology was examined using SEM to evaluate the degree of platelet activation (FIG. 10). The results demonstrate extensive activation and fused degranulated platelets for platelets on collagen gels (FIGS. 10A and 10D). Platelets were more activated on electrospun collagen mats than PFC mats. (FIGS. 10B and 10E) Platelets on PFC mats appeared less activated with distinctly spherical features (FIGS. 10C and 10F) as compared to the appearance of platelets on collagen electrospun mat on the collagen gel.

Example 11

Platelet Adhesion to Materials Containing HUVECs

Figure 11:
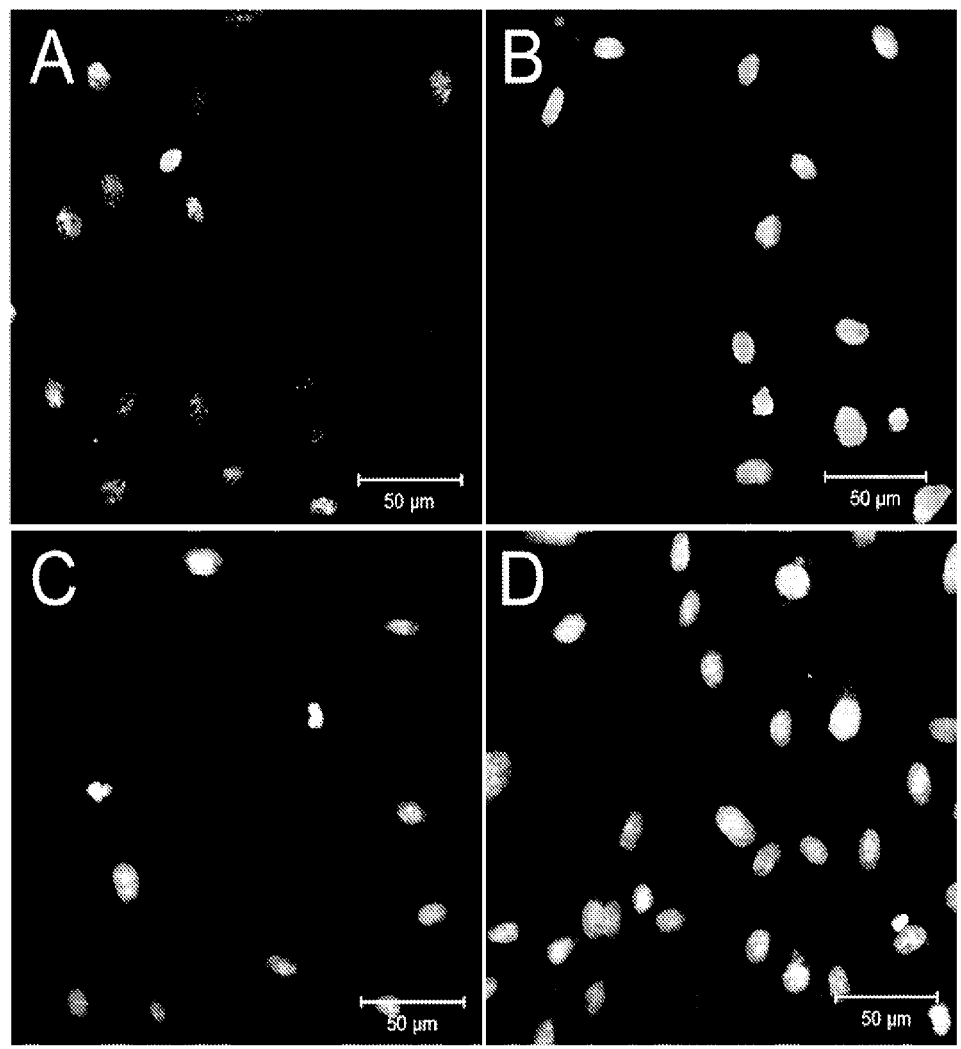
FIG. 11 displays confocal images illustrating the association and interaction of platelets with HUVECs on different substrate. PRP were plated at 1.08×107 platelets/dish in a 48-well plate. The images were acquired after 15 min of incubation of platelets on various substrate surfaces at 37° C. A: PFC mat, B: collagen mat, C: culture dish, D: collagen gel. Formation of microthrombi on the collagen gel and increased size of platelet aggregates was observed on the collagen gel and collagen mat as compared to the culture dish and PFC mat. F-actin of cells and platelets were stained using rhodamine-phalloidin and nuclei of cells were stained using sytox green (Magnification 40×; Scale bar: 50 µm).

In a second experiment platelets were applied to mats cultured for 24 hours with HUVECs (50,000 cells/well in a 48-well plate) (FIG. 11). More adherent platelets on collagen electrospun mat and formation of microthrombi in larger size on collagen gel were seen, in contrast to single platelets or clumps of 2-3 platelets on culture dishes and PFC mats (FIG. 11). For all materials the presence of endothelial cells significantly reduced the number of adherent platelets demonstrating the nonthrombogenic nature of the endothelial cell glycocalyx. A 60% reduction in total adherent platelets mat was observed (FIG. 12) on the PFC mat as compared to the culture dish (p<0.05). The number of platelets decreased 2.9-fold on PFC mat compared to the electrospun collagen mat (p<0.05), and 2.2 fold compared to the collagen gel (p<0.05).

Figure 12:
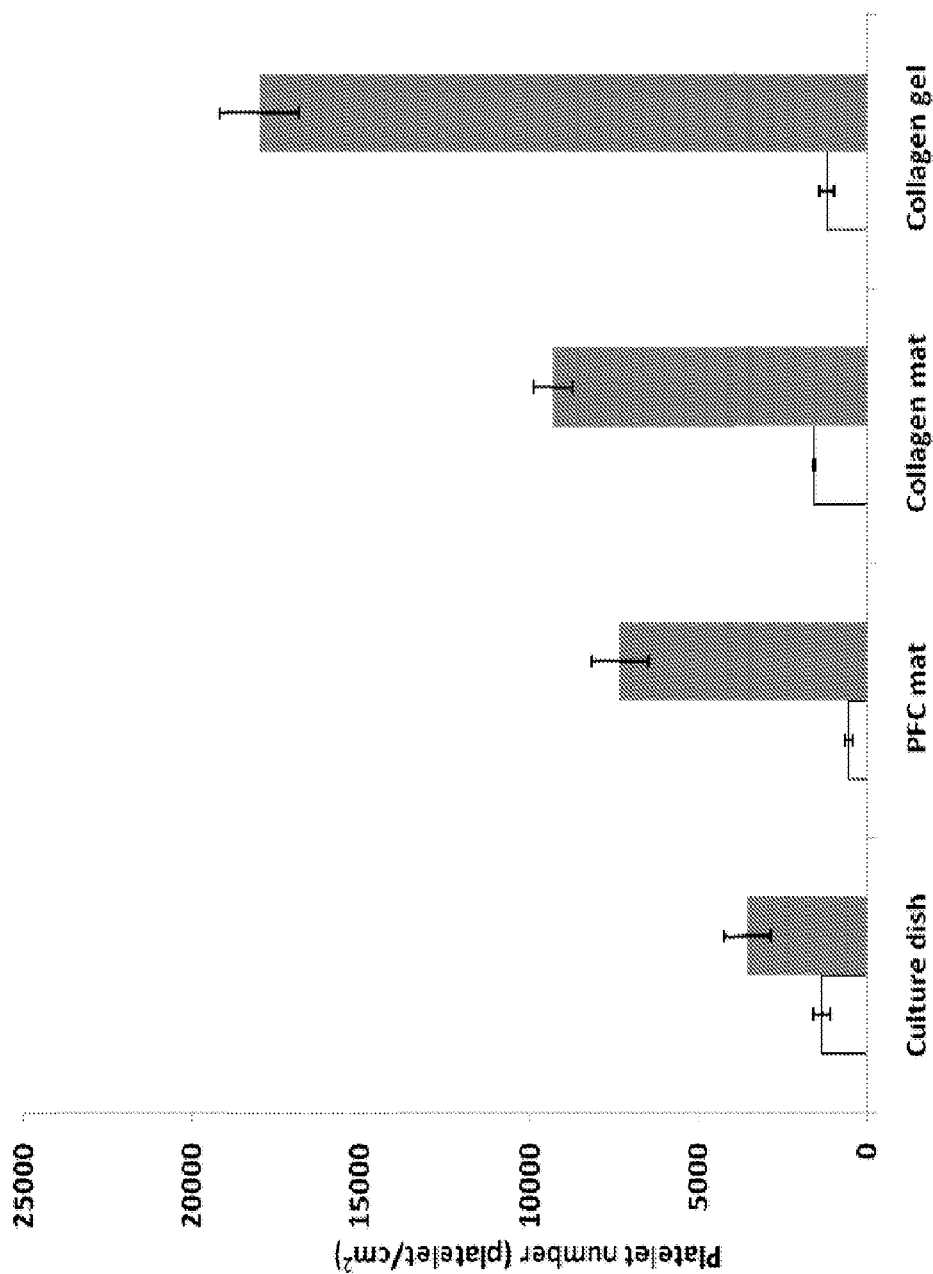
FIG. 12 illustrates platelet interaction with cells cultured on different substrates. Numbers of adhered platelets were counted from representative photomicrographs taken from culture dish, PFC mat, collagen mat, and collagen gel substrates after 15 min incubation at 37° C. White bars (☐) indicate areas of the material without endothelial cells, whereas grey bars (☐) indicate platelet counts for areas with cells. Data are expressed as mean±standard error of the mean (n=3).
Figure 13A:
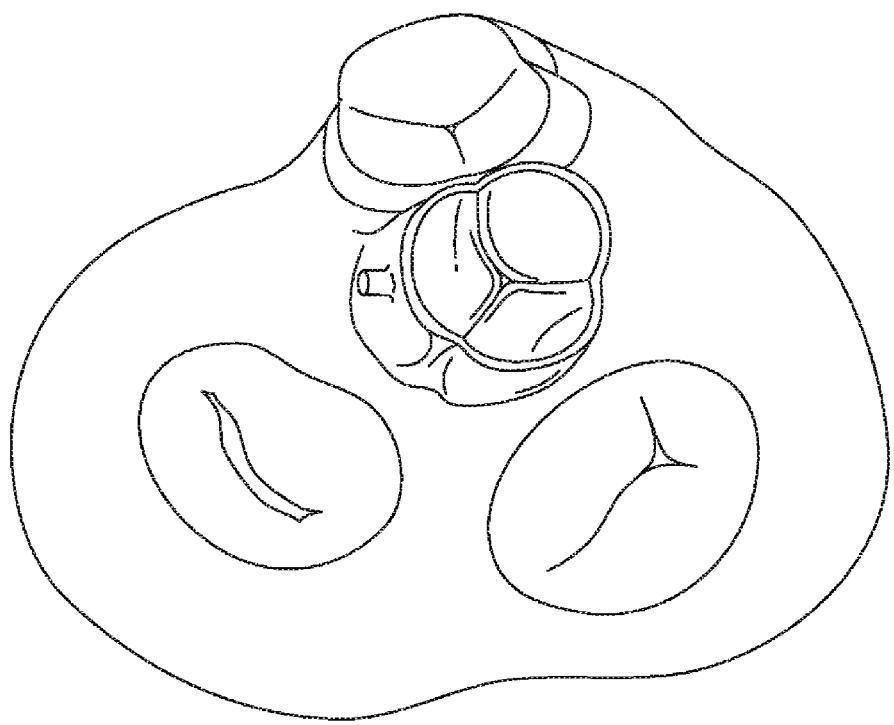
FIGS. 13A, 13B illustrate a heart valve and a stent, respectively, in accordance with the present invention.
Figure 13B:
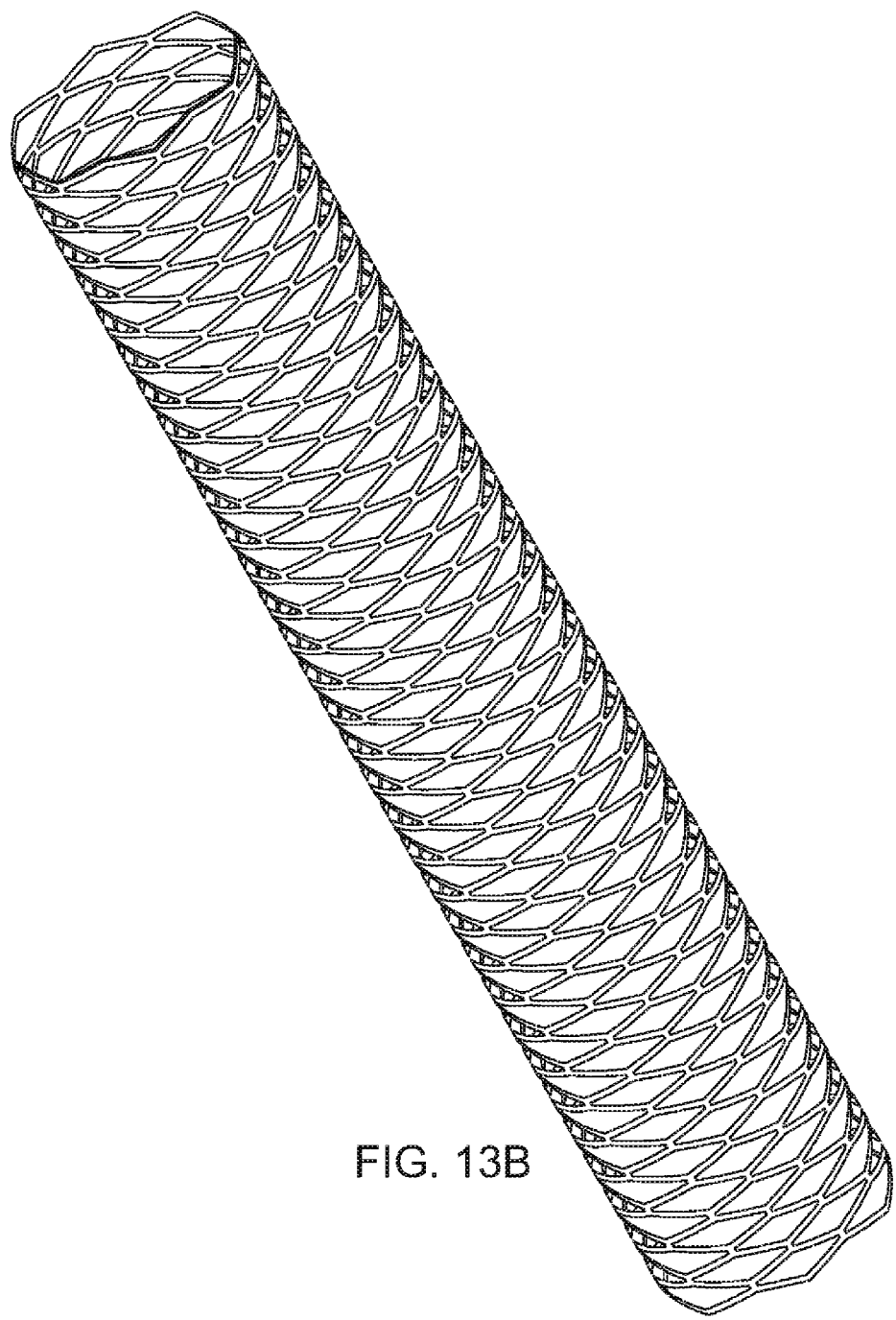

When areas of mats without endothelial cells were examined, while not statistically significant, a 27% reduction of platelet number on the PFC mat was observed as compared to the electrospun collagen. (FIG. 12).

A number of patent and non-patent publications are cited in this application in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

Furthermore, the transitional terms "comprising", "consisting essentially of" and "consisting of", when used in the appended claims, in original and amended form, define claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified materials (s). The term "consisting essentially of" limits the scope of a claim to the specified elements, steps or material(s) and those that do not material affect the basic and novel characteristic (s) of the claimed invention. All biomaterials and methods for preparing and utilizing the same that embody the present invention can, in alternate embodiments, be more specifically defined by any of the transitional terms "comprising", "consisting essentially of" and "consisting of".

REFERENCES

Alberts, B., A. Johnson, et al. (2002). Molecular biology of the cell, Garland Science Taylor & Francis Group.

Apte, S. S. (2011). "Current developments in the tissue engineering of autologous heart valves: moving towards clinical use." Future cardiology 7(1): 77-97.

Beun, L. H., X. J. Beaudoux, et al. (2011). "Self-Assembly of Silk-Collagen-like Triblock Copolymers Resembles a Supramolecular Living Polymerization." ACS Nano 6(1): 133-140.

Billiar, K. L. and M. S. Sacks (2000). "Biaxial Mechanical Properties of the Native and Glutaraldehyde-Treated Aortic Valve Cusp: Part II—A Structural Constitutive Model." Journal of Biomechanical Engineering 122(4): 327-335.

Bondar, B., S. Fuchs, et al. (2008). "Functionality of endothelial cells on silk fibroin nets: Comparative study of micro- and nanometric fibre size." Biomaterials 29(5): 561-572.

Breuer, C. K. (2004). "Application of tissue-engineering principles toward the development of a semilunar heart valve substitute." Tissue engineering 10(11-12): 1725-1736.

Butcher, J. T., G. J. Mahler, et al. (2011). "Aortic valve disease and treatment: The need for naturally engineered solutions." Advanced Drug Delivery Reviews 63(4-5): 242-268.

Cebotari, S. (2011). "Use of fresh decellularized allografts for pulmonary valve replacement may reduce the reoperation rate in children and young adults: early report." Circulation (New York, N.Y.) 124(11 suppl): S115-123.

Chen, W.-Q., H. Priewalder, et al. (2010). "Silk cocoon of Bombyx mori: Proteins and posttranslational modifications—heavy phosphorylation and evidence for lysine-mediated cross links." PROTEOMICS 10(3): 369-379.

Chobanian, A. V., G. L. Bakris, et al. (2003). "Seventh Report of the Joint National Committee on Prevention, Detection, Evaluation, and Treatment of High Blood Pressure." Hypertension 42(6): 1206-1252.

Cilurzo, F., C. G. M. Gennari, et al. (2011). "An investigation into silk fibroin conformation in composite materials intended for drug delivery." International Journal of Pharmaceutics 414(1-2): 218-224.

De Cock, L. J. (2010). "Layer-by-layer incorporation of growth factors in decellularized aortic heart valve leaflets." Biomacromolecules 11(4): 1002-1008.

De Cupere, V. M., J. Van Wetter, et al. (2003). "Nanoscale Organization of Collagen and Mixed Collagen—Pluronic Adsorbed Layers." Langmuir 19(17): 6957-6967.

Deng, C. (2011). "Application of decellularized scaffold combined with loaded nanoparticles for heart valve tissue engineering in vitro." Journal of Huazhong University of Science and Technology. Medical sciences 31(1): 88-93.

Dijkman, P. E., A. Driessen-Mol, et al. (2012). "Decellularized homologous tissue-engineered heart valves as off-the-shelf alternatives to xeno- and homografts." Biomaterials(0).

Dohmen, P. M., A. Lembcke, et al. (2011). "Ten Years of Clinical Results With a Tissue-Engineered Pulmonary Valve." The Annals of Thoracic Surgery 92(4): 1308-1314.

Edwards, M. B., E. R. Draper, et al. (2005). "Mechanical testing of human cardiac tissue: some implications for MRI safety." J Cardiovasc Magn Reson 7(5): 835-840.

Gu, X. and K. S. Masters (2010). "Regulation of valvular interstitial cell calcification by adhesive peptide sequences." Journal of Biomedical Materials Research Part A 93A(4): 1620-1630.

Hayashi, T. and S. Mukamel (2007). "Vibrational-Exciton Couplings for the Amide I, II, III, and A Modes of Peptides." The Journal of Physical Chemistry B 111(37): 11032-11046.

Hinton, R. B. and K. E. Yutzey (2011). "Heart Valve Structure and Function in Development and Disease." Annual Review of Physiology 73(1): 29-46.

Hopkins, R. A. (2005). "Tissue engineering of heart valves: decellularized valve scaffolds." Circulation (New York, N.Y.) 111(21): 2712-2714.

Horan, R. L., K. Antle, et al. (2005). "In vitro degradation of silk fibroin." Biomaterials 26(17): 3385-3393.

Hu, X., D. Kaplan, et al. (2006). "Determining Beta-Sheet Crystallinity in Fibrous Proteins by Thermal Analysis and Infrared Spectroscopy." Macromolecules 39(18): 6161-6170.

Jiang, C., X. Wang, et al. (2007). "Mechanical Properties of Robust Ultrathin Silk Fibroin Films." Advanced Functional Materials 17(13): 2229-2237.

Jordan, J. E., J. K. Williams, et al. (2012). "Bioengineered self-seeding heart valves." The Journal of thoracic and cardiovascular surgery 143(1): 201-208.

Kidane, A. G., G. Burriesci, et al. (2009). "A novel nanocomposite polymer for development of synthetic heart valve leaflets." Acta Biomaterialia 5(7): 2409-2417.

Kim, K., M. Yu, et al. (2003). "Control of degradation rate and hydrophilicity in electrospun non-woven poly(d,l-lactide) nanofiber scaffolds for biomedical applications." Biomaterials 24(27): 4977-4985.

Lee, K.-W., D. B. Stolz, et al. (2011). "Substantial expression of mature elastin in arterial constructs." Proceedings of the National Academy of Sciences 108(7): 2705-2710.

Liu, T., W. K. Teng, et al. (2010). "Photochemical crosslinked electrospun collagen nanofibers: Synthesis, characterization and neural stem cell interactions." Journal of Biomedical Materials Research Part A 95A(1): 276-282.

Lombardi, S. J. and D. L. Kaplan (1990). "The Amino Acid Composition of Major Ampullate Gland Silk (Dragline) of Nephila Clavipes (Araneae, Tetragnathidae)." Journal of Arachnology 18(3): 297-306.

Malafaya, P. B., G. A. Silva, et al. (2007). "Natural-origin polymers as carriers and scaffolds for biomolecules and cell delivery in tissue engineering applications." Advanced Drug Delivery Reviews 59(4-5): 207-233.

Mendelboum Raviv, S., K. Szekeres-Csiki, et al. (2011). "Coating conditions matter to collagen matrix formation regarding von Willebrand factor and platelet binding." Thrombosis Research(0).

Minoura, N., M. Tsukada, et al. (1990). "Fine structure and oxygen permeability of silk fibroin membrane treated with methanol." Polymer 31(2): 265-269.

Mirensky, T. L. and C. K. Breuer (2008). "The Development of Tissue-Engineered Grafts for Reconstructive Cardiothoracic Surgical Applications." Pediatr Res 63(5): 559-568.

Mol, A. (2004). "Review article: Tissue engineering of semilunar heart valves: current status and future developments." The Journal of heart valve disease 13(2): 272-280.

Motlagh, D., J. Yang, et al. (2006). "Hemocompatibility evaluation of poly(glycerol-sebacate) in vitro for vascular tissue engineering." Biomaterials 27(24): 4315-4324.

Newton, D., R. Mahajan, et al. (2009). "Regulation of material properties in electrospun scaffolds: Role of cross-linking and fiber tertiary structure." Acta Biomaterialia 5(1): 518-529.

Nkomo, V. T., J. M. Gardin, et al. (2006). "Burden of valvular heart diseases: a population-based study." The Lancet 368(9540): 1005-1011.

Okhawilai, M. (2010). "Preparation of Thai silk fibroin/gelatin electrospun fiber mats for controlled release applications." International journal of biological macromolecules 46(5): 544-550.

Pomerantseva, I., N. Krebs, et al. (2009). "Degradation behavior of poly(glycerol sebacate)." Journal of Biomedical Materials Research Part A 91A(4): 1038-1047.

Rockwood, D. N., R. C. Preda, et al. (2011). "Materials fabrication from Bombyx mori silk fibroin." Nat. Protocols 6(10): 1612-1631.

Ruzmetov, M., J. J. Shah, et al. (2012). "Decellularized versus standard cryopreserved valve allografts for right ventricular outflow tract reconstruction: A single-institution comparison." The Journal of thoracic and cardiovascular surgery 143(3): 543-549.

Sacks, M. S., F. J. Schoen, et al. (2009). "Bioengineering Challenges for Heart Valve Tissue Engineering." Annual Review of Biomedical Engineering 11(1): 289-313.

Sant, S., C. M. Hwang, et al. (2011). "Hybrid PGS-PCL microfibrous scaffolds with improved mechanical and biological properties." Journal of Tissue Engineering and Regenerative Medicine 5(4): 283-291.

Sant, S. and A. Khademhosseini (2010). Fabrication and characterization of tough elastomeric fibrous scaffolds for tissue engineering applications. Engineering in Medicine and Biology Society (EMBC), 2010 Annual International Conference of the IEEE.

Schopka, S. (2009). "Recellularization of biological heart valves with human vascular cells: in vitro hemocompatibility assessment." Journal of biomedical materials research. Part B, Applied biomaterials 88(1): 130-138.
Schroeder, W. A., L. M. Kay, et al. (1955). "The Amino Acid Composition of Bombyx mori Silk Fibroin and of Tussah Silk Fibroin." Journal of the American Chemical Society 77(14): 3908-3913.
Sell, S. A., M. J. McClure, et al. (2009). "Electrospinning of collagen/biopolymers for regenerative medicine and cardiovascular tissue engineering." Advanced Drug Delivery Reviews 61(12): 1007-1019.
Sell, S. A., P. S. Wolfe, et al. (2010). "The Use of Natural Polymers in Tissue Engineering: A Focus on Electrospun Extracellular Matrix Analogues." Polymers 2(4): 522-553.
Shekaran, A. and A. J. Garcia (2011). "Nanoscale engineering of extracellular matrix-mimetic bioadhesive surfaces and implants for tissue engineering." Biochimica et Biophysica Acta (BBA)—General Subjects 1810(3): 350-360.
Simon, P., M. T. Kasimir, et al. (2003). "Early failure of the tissue engineered porcine heart valve SYNERGRAFT® in pediatric patients." European Journal of Cardio-Thoracic Surgery 23(6): 1002-1006.
Simone, E. A., T. D. Dziubla, et al. (2009). "Filamentous Polymer Nanocarriers of Tunable Stiffness that Encapsulate the Therapeutic Enzyme Catalase." Biomacromolecules 10(6): 1324-1330.
Soliman, S., S. Sant, et al. (2011). "Controlling the porosity of fibrous scaffolds by modulating the fiber diameter and packing density." Journal of Biomedical Materials Research Part A 96A(3): 566-574.
Sung, H.-W., C.-N. Chen, et al. (2000). "In vitro surface characterization of a biological patch fixed with a naturally occurring crosslinking agent." Biomaterials 21(13): 1353-1362.
Tedder, M. E. (2009). "Stabilized collagen scaffolds for heart valve tissue engineering." Tissue engineering. Part A 15(6): 1257-1268.
Trowbridge, E. A., P. V. Lawford, et al. (1989). "Pericardial heterografts: a comparative study of suture pull-out and tissue strength." Journal of Biomedical Engineering 11(4): 311-314.
Um, I. C., H. Kweon, et al. (2001). "Structural characteristics and properties of the regenerated silk fibroin prepared from formic acid." International journal of biological macromolecules 29(2): 91-97.
Vesely, I. and R. Noseworthy (1992). "Micromechanics of the fibrosa and the ventricularis in aortic valve leaflets." Journal of Biomechanics 25(1): 101-113.
Wan, L.-S. and Z.-K. Xu (2009). "Polymer surfaces structured with random or aligned electrospun nanofibers to promote the adhesion of blood platelets." Journal of Biomedical Materials Research Part A 89A(1): 168-175.
Wang, Y., G. A. Ameer, et al. (2002). "A tough biodegradable elastomer." Nat Biotech 20(6): 602-606.
Yacoub, M. H. and L. H. Cohn (2004). "Novel Approaches to Cardiac Valve Repair." Circulation 109(9): 1064-1072.
Yacoub, M. H. and J. J. M. Takkenberg (2005). "Will heart valve tissue engineering change the world?" Nat Clin Pract Cardiovasc Med 2(2): 60-61.
Yamada, K. M., D. W. Kennedy, et al. (1980). "Characterization of fibronectin interactions with glycosaminoglycans and identification of active proteolytic fragments." Journal of Biological Chemistry 255(13): 6055-6063.
Yi, F. and D. A. LaVan (2008). "Poly(glycerol sebacate) Nanofiber Scaffolds by Core/Shell Electrospinning." Macromolecular Bioscience 8(9): 803-806.
Yoganathan, A. P., Z. He, et al. (2004). "FLUID MECHANICS OF HEART VALVES." Annual Review of Biomedical Engineering 6(1): 331-362.
Zhou, C.-Z., et al. (2001) "Silk Fibroin: Structural implications of a remarkable amino acid sequence." Proteins: Structure, Function, and Bioinformatics 44(2): p. 119-122.
Zhou, J., C. Cao, et al. (2010). "In vitro and in vivo degradation behavior of aqueous-derived electrospun silk fibroin scaffolds." Polymer Degradation and Stability 95(9): 1679-1685.
Zhu, J., A. Negri, et al. (2010). "Closed headpiece of integrin alphaIIbbeta3 and its complex with an alphaIIbbeta3-specific antagonist that does not induce opening." Blood (2010 Aug. 2): 2010 December 2012; 2116(2023):5050-2019.
Zoccola, M., A. Aluigi, et al. (2008). "Study on Cast Membranes and Electrospun Nanofibers Made from Keratin/Fibroin Blends." Biomacromolecules 9(10): 2819-2825.
Zong, X., S. Ran, et al. (2003). "Structure and Morphology Changes during in Vitro Degradation of Electrospun Poly(glycolide-co-lactide) Nanofiber Membrane." Biomacromolecules 4(2): 416-423.
Zou, L., S. Cao, et al. (2012). "Fibronectin induces endothelial cell migration through beta1-integrin and Src dependent phosphorylation of fibroblast growth factor receptor-1 at tyrosines 653/654 and 766." Journal of Biological Chemistry.

What is claimed is:

1. A porous electrospun graft material configured to replace biological tissue, the electrospun graft material comprising a collagen, a fibroin, and a hemocompatible synthetic elastomer,
  wherein the hemocompatible synthetic elastomer is a polyglycerol derivative ester comprising a polycarboxylic acid, and
  wherein collagen comprises 45 wt. % of the total composition weight, fibroin comprises 45 wt. % of the total composition weight, and the polyglycerol derivative ester comprising a polycarboxylic acid comprises 10 wt. % of the total composition weight.

2. The porous electrospun graft material according to claim 1, wherein the biological tissue is heart tissue.

3. The porous electrospun graft material according to claim 1, wherein the porous electrospun graft material has the shape of a heart valve.

4. The porous electrospun graft material according to claim 1, wherein the porous electrospun graft material has the shape of an aortic heart valve.

5. The porous electrospun graft material according to claim 1, wherein the porous electrospun graft material has the shape of a stent.

6. The porous electrospun graft material according to claim 1, wherein the porous electrospun graft material has a percentage weight loss of no more than 0.3% per week over a 30 week period incubated at 37° C. in phosphate buffered saline (PBS) containing 0.1% sodium azide, with percentage weight loss calculated according to the formula weight loss (%)=$W_f/W_i \times 100\%$, where $W_i$ is the initial weight and $W_f$ is the weight loss.

7. The porous electrospun graft material according to claim 1, wherein the porous electrospun graft material is structurally and mechanically similar to native tissue.

8. The porous electrospun graft material according to claim 1, wherein the porous electrospun graft material is structurally and mechanically similar to native heart valve tissue.

9. The porous electrospun graft material according to claim 1, wherein the porous electrospun graft material is configured to promote cell adherence and proliferation.

10. The porous electrospun graft material according to claim 1, wherein the porous electrospun graft material is resorbable.

11. The porous electrospun graft material according to claim 1, wherein the porous electrospun graft material comprises a porous network of interconnected fibers effective to facilitate nutrient transport and cell signaling.

12. The porous electrospun graft material according to claim 1, wherein the porous electrospun graft material comprises a sheet material.

13. The porous electrospun graft material according to claim 1, wherein the porous electrospun graft material is sufficiently porous to facilitate cell adhesion, nutrient transport and signal transmission.

14. The porous electrospun graft material according to claim 1, wherein the porous electrospun graft material comprises a fibrous structure.

15. The porous electrospun graft material according to claim 14, wherein the fibers of the fibrous structure have a diameter of 2712 to 3192 nm.

16. The porous electrospun graft material according to claim 14, wherein the fibers of the fibrous structure have a diameter of 2900 to 3000 nm.

17. The porous electrospun graft material according to claim 1, wherein the porous electrospun graft material comprises a porous network of interconnected fibers, wherein the porous network is 100 to 300 µm thick.

18. The porous electrospun graft material according to claim 1, wherein the porous electrospun graft material has a porosity of 67% to 80%, with the porosity calculated as $$\varepsilon = \frac{V_{liq}}{V_{liq} + V_{MAT}},$$

where $V_{liq}$ is volume of intruded water and $V_{MAT}$ is the volume of the electrospun graft material.

19. The porous electrospun graft material according to claim 1, wherein the porous electrospun graft material has an elastic modulus from 3.98 to 4.24 Mpa, with the modulus calculated using a 500 N load cell to perform uniaxial tensile tests after hydration of the porous electrospun graft material in 100 ml $DDH_2O$ for 10 minutes at an elongation rate of 10 mm/min.

20. The porous electrospun graft material according to claim 1, wherein the porous electrospun graft material has a stress value of 1.40 to 1.50 Mpa, with the stress value calculated using a 500 N load cell to perform uniaxial tensile tests after hydration of the porous electrospun graft material in 100 ml $DDH_2O$ for 10 minutes at an elongation rate of 10 mm/min.

21. The porous electrospun graft material according to claim 1, wherein the porous electrospun graft material has a strain value of 0.40 to 0.42 mm/mm, with the strain value calculated using a 500 N load cell to perform uniaxial tensile tests after hydration of the porous electrospun graft material in 100 ml $DDH_2O$ for 10 minutes at an elongation rate of 10 mm/min.

22. The porous electrospun graft material according to claim 1, wherein the collagen is type I collagen.

23. The porous electrospun graft material according to claim 1, wherein the fibroin is silk fibroin.

24. The porous electrospun graft material according to claim 1, wherein the hemocompatible synthetic elastomer is poly (glycerol sebacate).

25. The porous electrospun graft material according to claim 1, further comprising an electronegative carbohydrate.

26. The porous electrospun graft material of claim 25, wherein the electronegative carbohydrate comprises a glycosaminoglycan, a growth factor, a cell signaling molecule, or a combination thereof.

27. A graft for heart valve replacement, comprising the porous electrospun graft material of claim 1.

28. The graft of claim 27, wherein the poly glycerol derivative is poly (glycerol sebacate).

29. A porous electrospun graft material configured to replace biological tissue, wherein the porous electrospun graft material comprises collagen: fibroin: poly (glycerol sebacate) at 4.5:4.5:1 weight ratio.

* * * * *